US012331291B2

(12) United States Patent
Li et al.

(10) Patent No.: US 12,331,291 B2
(45) Date of Patent: Jun. 17, 2025

(54) SPLIT COMPLEMENTARY BASE EDITING SYSTEMS BASED ON BIMOLECULAR DEAMINASES AND USES THEREOF

(71) Applicant: SUN YAT-SEN UNIVERSITY, Guangdong (CN)

(72) Inventors: Jianfeng Li, Guangdong (CN); Xiangyu Xiong, Guangdong (CN); Kehui Liu, Guangdong (CN); Xionglei He, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 0 days.

(21) Appl. No.: 18/777,597

(22) Filed: Jul. 19, 2024

(65) Prior Publication Data

US 2024/0368590 A1 Nov. 7, 2024

Related U.S. Application Data

(63) Continuation of application No. PCT/CN2022/106402, filed on Jul. 19, 2022.

(30) Foreign Application Priority Data

May 10, 2022 (CN) .......................... 202210503831.5

(51) Int. Cl.
| | |
|---|---|
| *C12N 15/11* | (2006.01) |
| *C12N 9/22* | (2006.01) |
| *C12N 9/78* | (2006.01) |
| *C12N 15/81* | (2006.01) |
| *C12N 15/82* | (2006.01) |
| *C12N 15/85* | (2006.01) |

(52) U.S. Cl.
CPC .............. *C12N 15/111* (2013.01); *C12N 9/22* (2013.01); *C12N 9/78* (2013.01); *C12N 15/81* (2013.01); *C12N 15/82* (2013.01); *C12N 15/85* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2019/0292553 A1 | 9/2019 | Gao et al. | |
| 2020/0340002 A1 | 10/2020 | Gao et al. | |
| 2021/0130805 A1 | 5/2021 | Gaudelli et al. | |
| 2021/0355508 A1* | 11/2021 | Chang | C12N 9/22 |
| 2022/0098593 A1 | 3/2022 | Gaudelli et al. | |
| 2022/0136012 A1 | 5/2022 | Gaudelli et al. | |
| 2022/0348894 A1 | 11/2022 | Bowen et al. | |

FOREIGN PATENT DOCUMENTS

| | | |
|---|---|---|
| CN | 107722125 A | 2/2018 |
| CN | 109312335 A | 2/2019 |
| CN | 110835629 A | 2/2020 |
| CN | 110835632 A | 2/2020 |
| CN | 110835634 A | 2/2020 |
| CN | 111172133 A | 5/2020 |
| CN | 111373041 A | 7/2020 |
| CN | 111718420 A | 9/2020 |
| CN | 111748578 A | 10/2020 |
| CN | 111801345 A | 10/2020 |
| CN | 112239756 A | 1/2021 |
| CN | 112266418 A | 1/2021 |
| CN | 112266420 A | 1/2021 |
| CN | 112654702 A | 4/2021 |
| CN | 112746083 A | 5/2021 |
| CN | 112979821 A | 6/2021 |
| CN | 113667017 A | 11/2021 |
| CN | 114058604 A | 2/2022 |
| CN | 114480391 A | 5/2022 |
| CN | 114686456 A | 7/2022 |
| CN | 114835821 A | 8/2022 |
| CN | 111518794 B | 5/2023 |
| KR | 20220039564 A | 3/2022 |
| WO | 2019120310 A1 | 6/2019 |
| WO | 2020168051 A1 | 8/2020 |
| WO | 2020214842 A1 | 10/2020 |

(Continued)

OTHER PUBLICATIONS

Xiangyu Xiong et al., Split complementation of base editors to minimize off-target edits, Nature Plants, Oct. 16, 2023.
Jianhui Wu et al., SNP-based pool genotyping and haplotype analysis accelerate fine-mapping of the wheat genomic region containing stripe rust resistance gene Yr26, Theoretical and Applied Genetics, Apr. 17, 2018, pp. 1481-1496, vol. 131, No. 7.
Melissa J. Landrum et al., ClinVar: public archive of interpretations of clinically relevant variants, Nucleic Acids Research, Nov. 17, 2015, pp. D862-D868, vol. 44, No. D1.
Andrew V. Anzalone et al., Genome editing with CRISPR-Cas nucleases, base editors, transposases and prime editors, Nature Biotechnology, Jul. 2020, pp. 824-844, vol. 38, No. 7.
Alexis C. Komor et al., Programmable editing of a target base in genomic DNA without double-stranded DNA cleavage, Nature, 2016, pp. 420-424, vol. 533, No. 7603.

(Continued)

*Primary Examiner* — Anne M. Gussow
*Assistant Examiner* — Kyle T Rega

(57) ABSTRACT

Disclosed are split complementary base editing systems based on bimolecular deaminases and uses thereof. A split complementary base editing system mainly includes base editing fusion proteins A and B that are from splitting at a deaminase domain embedded inside a Cas9 nickase (nCas9), and a guide RNA (gRNA). The present disclosures of split complementary cytosine base editing systems can greatly reduce Cas9-dependent and Cas9-independent off-target effects in the genome while maintaining robust on-target cytosine base editing. The present disclosures also provide the split complementary adenine base editing systems. The split complementary cytosine (adenine) base editing systems are widely applicable to various eukaryotic organisms, and can be used in crop genetic breeding, animal breed improvement, and even clinical treatment of human genetic diseases.

3 Claims, 26 Drawing Sheets

Specification includes a Sequence Listing.

(56) References Cited

FOREIGN PATENT DOCUMENTS

| WO | 2021042047 A1 | 3/2021 |
| WO | 2021042062 A2 | 3/2021 |
| WO | 2021150646 A1 | 7/2021 |
| WO | 2021158921 A2 | 8/2021 |
| WO | 2021175288 A1 | 9/2021 |
| WO | 2021175289 A1 | 9/2021 |
| WO | 2022060185 A1 | 3/2022 |

OTHER PUBLICATIONS

Shuai Jin et al., Cytosine, but not adenine, base editors induce genome-wide off-target mutations in rice, Science, Feb. 28, 2019, pp. 292-295, vol. 364, No. 6437.

Erwei Zuo et al., Cytosine base editor generates substantial off-target single-nucleotide variants in mouse embryos, Science, Feb. 28, 2019, pp. 289-292, vol. 364, No. 6437.

Jeannette Steinert et al., Highly efficient heritable plant genome engineering using Cas9 orthologues from *Streptococcus thermophilus* and *Staphylococcus aureus*, The Plant Journal, Nov. 18, 2015, pp. 1295-1305, vol. 84, No. 6.

Jian-Feng Li et al., Multiplex and homologous recombination-mediated genome editing in *Arabidopsis* and Nicotiana benthamiana using guide RNA and Cas9, Nature Biotechnology, Aug. 2013, pp. 688-691, vol. 31, No. 8.

Zhenxiang Li et al., Targeted Transcriptional Activation in Plants Using a Potent Dead Cas9-Derived Synthetic Gene Activator, Current Protocols in Molecular Biology, 2019, pp. 1-23, vol. 127, No. e89.

Enis Afgan et al., The Galaxy platform for accessible, reproducible and collaborative biomedical analyses: 2018 update, Nucleic Acids Research, 2018, pp. W537-W544, vol. 46, No. W1.

Kendell Clement et al., CRISPResso2 provides accurate and rapid genome editing sequence analysis, Nature Biotechnology, Feb. 26, 2019, pp. 224-226, vol. 37, No. 3.

Gue-Ho Hwang et al., Web-based design and analysis tools for CRISPR base editing, BMC Bioinformatics, Dec. 27, 2018, pp. 1-7, vol. 19, No. 1.

Shuai Jin et al., Rationally Designed APOBEC3B Cytosine Base Editors with Improved Specificity, Molecular Cell, Sep. 3, 2020, pp. 728-740, vol. 79, No. 5.

Xiangyu Xiong et al., A cytosine base editor toolkit with varying activity windows and target scopes for versatile gene manipulation in plants, Nucleic Acids Research, Mar. 14, 2022, pp. 3565-3580, vol. 50, No. 6.

Kehui Liu et al., Mapping single-cell-resolution cell phylogeny reveals cell population dynamics during organ development, Nature Methods, Dec. 2021, pp. 1503-1514, vol. 18, No. 12.

Piaopiao Chen et al., The nonessentiality of essential genes in yeast provides therapeutic insights into a human disease, Genome Research, Jul. 20, 2016, pp. 1355-1362, vol. 26, No. 10.

Junjie Tan et al., Engineering of high-precision base editors for site-specific single nucleotide replacement, Nature Communications, 2019, pp. 1-10, vol. 10, No. 1.

Le Cong et al., Multiplex Genome Engineering Using CRISPR/Cas Systems, Science, Oct. 11, 2013, pp. 819-823, vol. 339, No. 6121.

Jordan L. Doman et al., Evaluation and Minimization of Cas9-Independent Off-Target DNA Editing by Cytosine Base Editors, Nature Biotechnology, 2020, pp. 1-27.

Xin Xu et al., Recent advances and applications of base editing systems, Chinese Journal of Biotechnology, Jul. 25, 2021, pp. 2307-2321, vol. 37, No. 7.

Jingzhou Chen et al., Advances in Base Editing and Research Progress in Its Application in Animal Breeding, Chinese Journal of Animal Science, 2022, pp. 53-59, vol. 58, No. 6.

First Office Action of counterpart Chinese Patent Application No. 202210503831.5 issued on Aug. 29, 2022.

Notice of Allowance of counterpart Chinese Patent Application No. 202210503831.5 issued on Dec. 12, 2022.

* cited by examiner

| Target gene site | Base editor | Total number of transgenic Arabidopsis thaliana | Total C to T editing efficiency | Indel ratio |
| --- | --- | --- | --- | --- |
| AtALS | Split-AID10 | 192 | 4.4% (8/192) | 0% (0/192) |
| AtTM166 | | 192 | 10.9% (21/192) | 0% (0/192) |

FIG. 5A

| Target gene site | Base editor | Total number of transgenic Arabidopsis thaliana | A to G editing efficiency | Indel ratio |
|---|---|---|---|---|
| AtABI3 | Split-ABE8e | 54 | 35.2% (19/54) | 0% (0/54) |
| AtPDS3 | Split-ABE8e | 192 | 11.5% (22/192) | 0% (0/192) |
| AtBAK1 | Split-ABE8e | 192 | 3.1% (6/192) | 0% (0/192) |

FIG. 9B

| Target gene site | Base editor | Total number of transgenic rice | A to G editing efficiency | Indel ratio |
| --- | --- | --- | --- | --- |
| OsACC | Split-ABE8e | 47 | 55.3% (26/47) | 0% (0/47) |
| OsDEP1 | Split-ABE8e | 49 | 55.1% (27/49) | 0% (0/49) |
| OsNRT1.1B | Split-ABE8e | 52 | 53.8% (28/52) | 0% (0/52) |

FIG. 9C

SPLIT COMPLEMENTARY BASE EDITING SYSTEMS BASED ON BIMOLECULAR DEAMINASES AND USES THEREOF

CROSS-REFERENCE TO RELATED APPLICATIONS

The present application is a continuation application of PCT application No. PCT/CN2022/106402 filed on Jul. 19, 2022, which claims the benefit of Chinese Patent Application No. 202210503831.5 filed on May 10, 2022. The contents of all of the aforementioned applications are incorporated by reference herein in their entirety.

REFERENCE TO SEQUENCE LISTING

This application includes a Sequence Listing filed electronically as an XML file named "Sequence listing_SCH-24050-USPT.xml", created on Jul. 10, 2024, with a size of 228,917 bytes. The Sequence Listing is incorporated herein by reference.

TECHNICAL FIELD

The present application relates to split complementary base editing systems based on bimolecular deaminases and uses thereof, and belongs to the technical field of genetic engineering.

BACKGROUND

Numerous crop agronomic traits and human genetic diseases are determined by single nucleotide polymorphisms (SNPs) in genomes[1,2]. The base editing technology derived from the CRISPR/Cas9 system has characteristics such as no induction of DNA double-strand breaks and accurate single-base substitutions at target sites, thus greatly improving the accuracy and safety of genome editing. Therefore, the base editing technology is widely used in fields such as gene function research, crop genetic improvement, and clinical treatment of human genetic diseases[3]. A base editing system mainly includes a base editor (BE) and a single-guide RNA (gRNA). BE3 most commonly used by researchers is produced by fusing cytidine deaminase rAPOBEC1 derived from rats and a uracil glycosylase inhibitor (UGI) derived from a phage with Cas9 nickase (nCas9)[4]. Under the guidance of sgRNA, BE3 binds to a target gene locus, the fused cytidine deaminase rAPOBEC1 catalyzes cytosine (C) bases into uracil (U) bases at a specific site in a target sequence, and under the action of endogenous repair mechanisms, uracil (U) bases are mutated into thymine (T) bases, thereby allowing base substitutions from C to T[4].

However, in recent years, various international independent studies in organisms such as rice and mice have shown that the traditional base editing systems (such as BE3) may induce a large number of random off-target mutations at genome-wide level independent of gRNA (or Cas9)[5, 6], which brings unpredictable safety risks in the practical use of base editing systems and especially brings a great uncertainty for clinical applications. Therefore, the development of efficient, universal, and safe base editing systems with low off-target effects is of great benefits to basic scientific research, crop genetic improvement, and even clinical treatment of human genetic diseases.

SUMMARY

An objective of the present application is to provide split complementary base editing systems with eliminated off-target effects and uses thereof. These base editing systems, which are based on complementary bimolecular deaminases, can greatly reduce the genome-wide off-target effects existing in the traditional base editing systems while still retaining robust on-target editing activity, and thus have a promising application prospect.

In order to allow the above objective, the present application adopts the following technical solutions: A split complementary base editing systems is provided, including at least one selected from the group consisting of the following (1) to (5):

(1) a base editing fusion protein A, a base editing fusion protein B, and a gRNA;
(2) an expression construct including nucleotide sequences encoding the base editing fusion protein A and the base editing fusion protein B respectively, and the gRNA;
(3) the base editing fusion protein A, the base editing fusion protein B, and an expression construct including the nucleotide sequence encoding the gRNA;
(4) the expression construct including the nucleotide sequences encoding the base editing fusion protein A and the base editing fusion protein B respectively, and the expression construct including the nucleotide sequence encoding the gRNA; and
(5) an expression construct including the nucleotide sequences encoding the base editing fusion protein A and the base editing fusion protein B respectively and the nucleotide sequence encoding the gRNA, where the base editing fusion protein A includes a first nCas9 polypeptide fragment, a flexible peptide linker, and a first nucleobase deaminase polypeptide fragment sequentially from N-terminus to C-terminus; the base editing fusion protein B includes a second nucleobase deaminase polypeptide fragment, the flexible peptide linker, and a second nCas9 polypeptide fragment sequentially from N-terminus to C-terminus; and the first nucleobase deaminase polypeptide fragment and the second nucleobase deaminase polypeptide fragment are derived from the same nucleobase deaminase.

It should be noted that the "expression construct" refers to a vector suitable for expressing a nucleotide sequence of interest in organisms, such as a recombinant vector. The "expression" means that a product with a function can be produced. For example, the expression of a nucleotide sequence can refer to transcription of the nucleotide sequence, such as transcription to produce massage RNA (mRNA) or functional RNA, and/or translation of RNA into a precursor or mature protein. The "expression construct" in the present application may be selected from the group consisting of a linear nucleic acid fragment, a circular plasmid, a viral vector, and a translatable RNA (such as mRNA). The "expression construct" in the present application may include a regulatory sequence and a nucleotide sequence of interest that are from the same source, but are in different natural arrangement modes, and may also include a regulatory sequence and a nucleotide sequence of interest that are from different sources.

The inventors of the present application have found that, in base editing systems of the present application, the gRNA can produce a ribonucleoprotein complex (RNP) with the base editing fusion protein A and the base editing fusion protein B, and guide the RNP to target a target DNA sequence, resulting in a nucleotide substitution from one or more cytosine (C) bases to one or more thymine (T) bases or one or more adenine (A) bases to one or more guanine (G) bases in the target sequence. Moreover, the first nucleobase deaminase polypeptide fragment and the second nucleobase deaminase polypeptide fragment both do not include a complete deaminase sequence and do not have any deamination activities, which is the key to reducing off-target effects.

The inventors of the present application have found that, in the base editing system of the present application, the first and second nucleobase deaminase polypeptide fragments are usually complementary, and can be fused into a nucleobase deaminase with the complete deamination activity.

As a preferred embodiment of the base editing system in the present application, an amino acid sequence of the first nCas9 polypeptide fragment is shown in SEQ ID NO: 1, and an amino acid sequence of the second nCas9 polypeptide fragment is shown in SEQ ID NO: 2.

As a preferred embodiment of the base editing system in the present application, the flexible peptide linker includes a linker peptide with 32 amino acids (aa) of an amino acid sequence shown in SEQ ID NO: 3. Studies have shown that the flexible peptide linker further includes XTEN, PR, GGGGS (SEQ ID NO: 33), PRGGSGG (SEQ ID NO: 34), ARGGSGG (SEQ ID NO: 35), GS, GAP, (GGGGS)×3 (SEQ ID NO: 180), GGS, and (GGS)×7 (SEQ ID NO: 181). The flexible peptide linker may also be a non-functional amino acid sequence that includes 1 to 50 or more amino acids and does not have a secondary or higher-level structure.

As a preferred embodiment of the base editing system in the present application, at least one nuclear localization signal peptide (NLS) is fused to an N-terminus or C-terminus of each of the base editing fusion protein A and the base editing fusion protein B. Studies have shown that the NLS can often interact with a nuclear vector to allow a target protein to be transported into a nucleus. In general, NLS is composed of one or more short sequences of positively-charged lysine or arginine exposed on the surface of a protein, but other types of NLS are also known. Non-limiting examples of NLS include an amino acid sequence such as PKKKRKV (SEQ ID NO: 36) or KRPAATKK-AGQAKKKK (SEQ ID NO: 37) derived from a *Xenopus laevis* nucleoplasmin. In some specific embodiments, the N-terminus of the base editing fusion protein A includes one copy of NLS (an amino acid sequence is PKKKRKV, as shown in SEQ ID NO: 36), and the C-terminus of the base editing fusion protein B includes one copy of NLS (an amino acid sequence is KRPAATKKAGQAKKKK, as shown in SEQ ID NO: 37) or 2 copies of NLS (amino acid sequences are PKKKRKV (SEQ ID NO: 36) and KRPAATKK-AGQAKKKK (SEQ ID NO: 37), respectively).

As a preferred embodiment of the base editing system in the present application, the base editing system is a cytosine base editing system; the nucleobase deaminase is a cytidine deaminase; and using this system, one or more C bases in a target sequence can be substituted with one or more T bases under the guidance of the gRNA.

As a preferred embodiment of the base editing system in the present application, the cytidine deaminase is selected from the group consisting of APOBEC3A (A3A), APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4), and AICDA (AID), and engineered cytidine deaminase variants with single amino acid mutation or a combination of amino acid mutations into APOBEC3A (A3A), APOBEC3B (A3B), APOBEC3C (A3C), APOBEC3D (A3D), APOBEC3F (A3F), APOBEC3G (A3G), APOBEC3H (A3H), APOBEC1 (A1), APOBEC3 (A3), APOBEC2 (A2), APOBEC4 (A4), or AICDA (AID).

As a preferred embodiment of the base editing system in the present application, the cytidine deaminase is selected from the group consisting of a hyperactive human AID variant AID10 (the Chinese patent: 202010285948.1), rat-derived rA1, human-derived hA3A, and human-derived hA3B.

As a preferred embodiment of the base editing system in the present application, a first nucleobase deaminase polypeptide fragment of a cytosine base editing fusion protein A includes any one amino acid sequence shown in SEQ ID NOS: 4-8, and a second nucleobase deaminase polypeptide fragment of a cytosine base editing fusion protein B includes any one amino acid sequence shown in SEQ ID NOS: 9-13.

As a preferred embodiment of the base editing system in the present application, at least one UGI is fused to a C-terminus of the cytosine base editing fusion protein B, and the UGI's amino acid sequence is shown in SEQ ID NO: 14.

As a preferred embodiment of the base editing system in the present application, the cytosine base editing system includes any combination of the base editing fusion protein A coupled with the base editing fusion protein B selected from the group consisting of the following (a) to (c):
(a) the base editing fusion protein A having an amino acid sequence shown in SEQ ID NO: 15 (Split-AID10-N), and the base editing fusion protein B having an amino acid sequence shown in SEQ ID NO: 16 (Split-AID10-C);
(b) the base editing fusion protein A having an amino acid sequence shown in SEQ ID NO: 17 (Split-AID10-N5), and the base editing fusion protein B having an amino acid sequence shown in SEQ ID NO: 18 (Split-AID10-C4);
(c) the base editing fusion protein A having an amino acid sequence shown in SEQ ID NO: 19 (Split-BE3-N), and the base editing fusion protein B having an amino acid sequence shown in SEQ ID NO: 20 (Split-BE3-C);
(d) the base editing fusion protein A having an amino acid sequence shown in SEQ ID NO: 21 (Split-A3A-N), and the base editing fusion protein B having an amino acid sequence shown in SEQ ID NO: 22 (Split-A3A-C); and
(c) the base editing fusion protein A having an amino acid sequence shown in SEQ ID NO: 23 (Split-A3B-N), and the base editing fusion protein B having an amino acid sequence shown in SEQ ID NO: 24 (Split-A3B-C).

In a specific embodiment provided in the present application, the base editing system is a cytosine base editing system "Split-AID10" based on complementary bimolecular cytidine deaminase fragments derived from the AID10. In the cytosine base editing system "Split-AID10", the base editing fusion protein A is produced by fusing an NLS polypeptide fragment, a first nCas9 polypeptide fragment (having an amino acid sequence shown in SEQ ID NO: 1), a 32 aa linker peptide (having an amino acid sequence shown in SEQ ID NO: 3), and a first nucleobase polypeptide fragment AID10-N (having an amino acid sequence shown in SEQ ID NO: 4) sequentially from N-terminus to C-terminus, has an amino acid sequence shown in SEQ ID NO: 15, and is called "Split-AID10-N"; and the base editing fusion protein B is produced by fusing a second nucleobase polypeptide fragment AID10-C (having an amino acid sequence shown in SEQ ID NO: 9), a 32 aa linker peptide, a second nCas9 polypeptide fragment (having an amino acid sequence shown in SEQ ID NO: 2), a UGI (having an amino acid sequence shown in SEQ ID NO: 14), and a NLS sequentially from N-terminus to C-terminus, has an amino acid sequence shown in SEQ ID NO: 16, and is called "Split-AID10-C" (as shown in FIG. 2).

In a specific embodiment provided in the present application, the base editing system is a cytosine base editing system "Split-AID10-N5-C4" based on complementary bimolecular cytidine deaminase fragments derived from the AID10. In the cytosine base editing system "Split-AID10-N5-C4", the base editing fusion protein A is produced by fusing a NLS polypeptide fragment, a first nCas9 polypeptide fragment, a 32aa linker peptide, and a first nucleobase polypeptide fragment AID10-N5 (having an amino acid sequence shown in SEQ ID NO: 5) sequentially from N-terminus to C-terminus, has an amino acid sequence shown in SEQ ID NO: 17, and is called "Split-AID10-N5"; and the base editing fusion protein B is produced by fusing a second nucleobase polypeptide fragment AID10-C4 (having an amino acid sequence shown in SEQ ID NO: 10), a 32aa linker peptide, a second nCas9 polypeptide fragment, a UGI, and a NLS sequentially from N-terminus to C-terminus, has an amino acid sequence shown in SEQ ID NO: 18, and is called "Split-AID10-C4" (as shown in FIG. 2).

In a specific embodiment provided in the present application, the base editing system is a cytosine base editing system "Split-BE3" based on complementary bimolecular cytidine deaminase fragments derived from the rA1. In the cytosine base editing system "Split-BE3", the base editing fusion protein A is produced by fusing a NLS polypeptide fragment, a first nCas9 polypeptide fragment, a 32aa linker peptide, and a first nucleobase polypeptide fragment BE3-N (having an amino acid sequence shown in SEQ ID NO: 6) sequentially from N-terminus to C-terminus, has an amino acid sequence shown in SEQ ID NO: 19, and is called "Split-BE3-N"; and the base editing fusion protein B is produced by fusing a second nucleobase polypeptide fragment BE3-C (having an amino acid sequence shown in SEQ ID NO: 11), a 32aa linker peptide, a second nCas9 polypeptide fragment, a UGI, and a NLS sequentially from N-terminus to C-terminus, has an amino acid sequence shown in SEQ ID NO: 20, and is called "Split-BE3-C".

In a specific embodiment provided in the present application, the base editing system is a cytosine base editing system "Split-A3A" based on complementary bimolecular cytidine deaminase fragments derived from the hA3A. In the cytosine base editing system "Split-A3A", the base editing fusion protein A is produced by fusing an NLS polypeptide fragment, a first nCas9 polypeptide fragment, a 32aa linker peptide, and a first nucleobase polypeptide fragment A3A-N (having an amino acid sequence shown in SEQ ID NO: 7) sequentially from N-terminus to C-terminus, has an amino acid sequence shown in SEQ ID NO: 21, and is called "Split-A3A-N"; and the base editing fusion protein B is produced by fusing a second nucleobase polypeptide fragment A3A-C (having an amino acid sequence shown in SEQ ID NO: 12), a 32aa linker peptide, a second nCas9 polypeptide fragment, a UGI, and an NLS sequentially from N-terminus to C-terminus, has an amino acid sequence shown in SEQ ID NO: 22, and is called "Split-A3A-C".

In a specific embodiment provided in the present application, the base editing system is a cytosine base editing system "Split-A3B" based on complementary bimolecular cytidine deaminase fragments derived from the hA3B. In the cytosine base editing system "Split-A3B", the base editing fusion protein A is produced by fusing a NLS polypeptide fragment, a first nCas9 polypeptide fragment, a 32aa linker peptide, and a first nucleobase polypeptide fragment A3B-N (having an amino acid sequence shown in SEQ ID NO: 8) sequentially from N-terminus to C-terminus, has an amino acid sequence shown in SEQ ID NO: 23, and is called "Split-A3B-N"; and the base editing fusion protein B is produced by fusing a second nucleobase polypeptide fragment A3B-C (having an amino acid sequence shown in SEQ ID NO: 13), a 32aa linker peptide, a second nCas9 polypeptide fragment, a UGI, and a NLS sequentially from N-terminus to C-terminus, has an amino acid sequence shown in SEQ ID NO: 24, and is called "Split-A3B-C".

As a preferred embodiment of the base editing system in the present application, the base editing system is an adenine base editing system; the nucleobase deaminase is an adenosine deaminase; and using this system, one or more A bases in a target sequence can be substituted with one or more G bases under the guidance of the gRNA.

As a preferred embodiment of the base editing system in the present application, the adenosine deaminase is a DNA-dependent adenosine deaminase, and preferably, the adenosine deaminase is a single-stranded DNA-dependent adenosine deaminase.

As a preferred embodiment of the base editing system in the present application, the adenosine deaminase includes variants of the *Escherichia coli* tRNA adenosine deaminase TadA; preferably, the variant is selected from the group consisting of TadA-7.10, TadA-8s, and TadA-8e; and more preferably, the variant is TadA-8e (the international patent: PCT/US2021/016827).

As a preferred embodiment of the base editing system in the present application, a first nucleobase deaminase polypeptide fragment of an adenine base editing fusion protein A includes any one amino acid sequence shown in SEQ ID NOS: 25-26, and a second nucleobase deaminase polypeptide fragment of an adenine base editing fusion protein B includes any one amino acid sequence shown in SEQ ID NOS: 27-28.

As a preferred embodiment of the base editing system in the present application, the adenine base editing system includes any combination of the base editing fusion protein A coupled with the base editing fusion protein B selected from the group consisting of the following (f) to (g):

(f) the base editing fusion protein A having an amino acid sequence shown in SEQ ID NO: 29 (Split-ABE8e-N), and the base editing fusion protein B with an amino acid sequence shown in SEQ ID NO: 30 (Split-ABE8e-C); and (g) the base editing fusion protein A having an amino acid sequence shown in SEQ ID NO: 31 (Split-ABE8e-N7), and the base editing fusion protein B having an amino acid sequence shown in SEQ ID NO: 32 (Split-ABE8e-C2).

In a specific embodiment provided in the present application, the base editing system is an adenine base editing system "Split-ABE8e" based on complementary bimolecular adenosine deaminase fragments derived from the TadA-8c. In the adenine base editing system "Split-ABE8e", the base editing fusion protein A is produced by fusing a NLS polypeptide fragment, a first nCas9 polypeptide fragment, a 32aa linker peptide, and a first nucleobase polypeptide fragment ABE8e-N (having an amino acid sequence shown in SEQ ID NO: 25) sequentially from N-terminus to C-terminus, has an amino acid sequence shown in SEQ ID NO: 29, and is called "Split-ABE8e-N"; and the base editing fusion protein B is produced by fusing a second nucleobase polypeptide fragment ABE8e-C (having an amino acid sequence shown in SEQ ID NO: 27), a 32aa linker peptide, a second nCas9 polypeptide fragment, and two copies of NLS sequentially from N-terminus to C-terminus, has an amino acid sequence shown in SEQ ID NO: 30, and is called "Split-ABE8e-C".

In a specific embodiment provided in the present application, the base editing system is an adenine base editing system "Split-ABE8e-N7-C2" based on complementary bimolecular adenosine deaminase fragments derived from the TadA-8c. In the adenine base editing system "Split-ABE8e-N7-C2", the base editing fusion protein A is produced by fusing a NLS polypeptide fragment, a first nCas9 polypeptide fragment, a 32aa linker peptide, and a first nucleobase polypeptide fragment ABE8e-N7 (having an amino acid sequence shown in SEQ ID NO: 26) sequentially from N-terminus to C-terminus, has an amino acid sequence shown in SEQ ID NO: 31, and is called "Split-ABE8e-N7"; and the base editing fusion protein B is produced by fusing a second nucleobase polypeptide fragment ABE8e-C2 (having an amino acid sequence shown in SEQ ID NO: 28), a 32aa linker peptide, a second nCas9 polypeptide fragment, and two copies of NLS sequentially from N-terminus to C-terminus, has an amino acid sequence shown in SEQ ID NO: 32, and is called "Split-ABE8e-C2".

As a preferred embodiment of the base editing system in the present application, the nucleotide sequences encoding the base editing fusion protein A and the base editing fusion protein B and/or the nucleotide sequence encoding the gRNA are/is operably linked to an expression regulatory element.

As a preferred embodiment of the base editing system in the present application, the expression regulatory element is a promoter; and the promoter is selected from the group consisting of a viral 35S promoter, a maize Ubi-1 promoter, a rice Ubi promoter, a CMV promoter, a yeast TDH3 promoter, a yeast GAL1 promoter, an *Arabidopsis thaliana* egg cell-specific EC1.2en+EC1.1 chimeric promoter, a rice U6 promoter, an *Arabidopsis thaliana* U6 promoter, and a human U6 promoter.

Studies have shown that examples of the promoter that may be used in the present application include, but are not limited to, polymerase (Pol) I, Pol II, or Pol III promoters. The Pol I promoter includes a chicken RNA Pol I promoter. The Pol II promoter includes, but is not limited to, a Rous sarcoma virus-long terminal repeat (RSV-LTR) promoter and a simian virus 40 (SV40) immediate-early promoter. The Pol III promoter includes the U6 and H1 promoters. An inducible promoter such as a metallothionein promoter may be adopted. When used in plants, the promoter may be selected from the group consisting of a cauliflower mosaic virus (CaMV) 35S promoter, a maize Ubi-1 promoter, a wheat U6 promoter, a rice U3 promoter, a maize U3 promoter, a rice actin promoter, an *Arabidopsis thaliana* egg cell-specific EC1.2en+EC1.1 chimeric promoter, and an *Arabidopsis thaliana* U6 promoter. When used in yeasts, the promoter may be selected from the group consisting of a yeast ADH1 promoter, a yeast TDH3 promoter, a yeast GAL1 promoter, and a yeast SNR52 promoter. When used in mammals such as human cells, the promoter may be selected from the group consisting of a CMV promoter and a human U3 or U6 promoter.

The present application also provides a use of the base editing system described above in production of genetically-modified organisms, where the base editing system is introduced into organism cells, whereby a BE targets a target sequence in a cell genome through the gRNA to make at least one C base substituted with at least one T base or at least one A base substituted with at least one G base in the target sequence.

As a preferred embodiment of the use in the present application, the organisms are eukaryotic organisms, and the eukaryotic organisms are fungi, animals, or plants.

As a preferred embodiment of the use in the present application, fungi includes yeasts; Animals are selected from the group consisting of humans, mice, rats, monkeys, dogs, pigs, sheep, cattle, and cats; and plants are selected from the group consisting of monocots and dicots, including, but not limited to, *Arabidopsis thaliana*, rice, wheat, maize, soybean, sunflower, sorghum, rape, alfalfa, cotton, barley, millet, sugarcane, tomato, tobacco, cassava, and potato.

The method of the present application is particularly suitable for production of genetically-modified plants, such as crops. For producing genetically-modified plants in the present application, the base editing system may be introduced into plants by various methods well known to those skilled in the art. The methods that may be used to introduce the base editing system in the present application into plants include, but are not limited to: a gene gun method, a polyethylene glycol (PEG)-mediated protoplast transformation method, an *Agrobacterium tumefaciens*-mediated transformation method, a plant virus-mediated transformation method, a pollen tube pathway method, and an ovary injection method.

In some preferred specific embodiments provided in the present application, the genetically-modified plants produced by using the split complementary base editing system has excellent agronomic traits. As shown in FIG. 5B, when the split complementary base editing system "Split-AID10" was used, and its gRNA was targeted to an endogenous gene ALS of *Arabidopsis thaliana*, a single-base substitution of $G_{13}>A_{13}$ occured at the endogenous target site in transgenic *Arabidopsis*, whereby an amino acid substitution from alanine to threonine (A122T) occured at position 122 in an amino acid sequence corresponding to the coding gene. The subsequent herbicide spraying assays showed that transgenic *Arabidopsis thaliana* plants having the A122T amino acid substitution are resistant to imidazolinone herbicides, while all *Arabidopsis thaliana* plants without the A122T amino acid substitution went death, indicating that the usage of the split complementary base editing system Split-AID10 provides excellent herbicide resistance for transgenic *Arabidopsis*.

Compared with the prior art, the present application has the following beneficial effects:

(1) Compared with the traditional cytosine base editing systems (such as the BE3 system), the split complementary cytosine base editing systems in the present application can reduce the genome-wide Cas9-dependent and Cas9-independent (random) off-target edits while still maintaining robust on-target activity.

(2) The split complementary adenine base editing systems provided in the present application also have universality in almost all representative eukaryotic organisms, and exhibits a prominent adenine base editing activity in monocots such as rice, dicots such as *Arabidopsis thaliana*, fungi such as yeasts, and mammals such as human HEK293T cells.

(3) The development and application of the split complementary base editing systems in the present application provide a safe and powerful technical support for scientific research of biological genes and genetic breeding of crops and especially for clinical treatment of human genetic diseases.

BRIEF DESCRIPTION OF THE DRAWINGS

FIG. 9B and FIG. 9C are statistical graphs of Split-ABE8e editing outcomes of three endogenous genes in transgenic Arabidopsis (FIG. 9B) and transgenic rice plants (FIG. 9C);

DETAILED DESCRIPTION OF THE EMBODIMENTS

To well explain the objective, technical solutions, and advantages of the present application, the present application will be further explained below with reference to specific embodiments. The terms and laboratory procedures related to protein and nucleic acid chemistry, molecular biology, cell and tissue cultivation, microbiology, and immunology herein arc widely-used terms and routine procedures in respective fields. For example, the standard recombinant DNA and molecular cloning techniques used in the present application are well known to those skilled in the art and are comprehensively described in the published literature. In the following embodiments, the experimental methods are conventional methods, and the test materials are available through conventional commercial purchases, unless otherwise specified.

Figure 1:
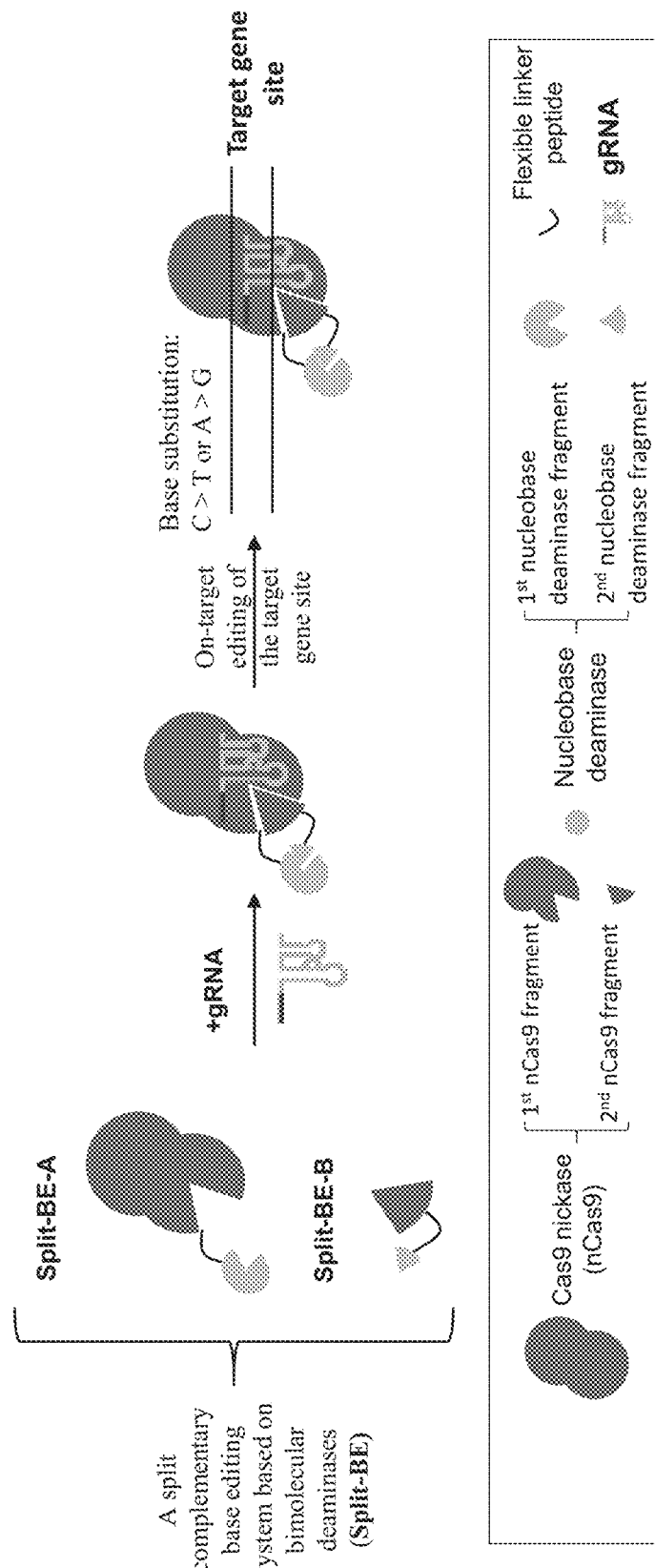
FIG. 1 shows the working principle of the split complementary base editing system.

As shown in FIG. 1, the split complementary base editing system provided in the present application mainly includes the following three parts: a base editing fusion protein A, a base editing fusion protein B, and a gRNA. The base editing fusion protein A and the base editing fusion protein B together constitute a complete BE with complementary bimolecular deaminases. The base editing fusion protein A is produced by fusing the first nCas9 polypeptide fragment with the first deaminase polypeptide fragment through a flexible peptide linker. The base editing fusion protein B is produced by fusing the second deaminase polypeptide fragment with the second nCas9 polypeptide fragment through a flexible peptide linker. The first and second nCas9 polypeptide fragments can be seamlessly fused into an intact nCas9 protein.

The first and second deaminase polypeptide fragments are derived from the same nucleobase deaminase, and any part of the first and second deaminase polypeptide fragments does not include the intact deaminase domain and also does not have the deaminase activity. In some preferred embodiments, in the cytosine base editing system Split-AID10 (FIG. 2, FIG. 3A to FIG. 3C, FIG. 4A, FIG. 4B, FIG. 5A, FIG. 5B, FIG. 6A, FIG. 6B, and FIG. 7A to FIG. 7D), Split-BE3 (FIG. 6A, FIG. 6B, and FIG. 7A to FIG. 7D), Split-A3A (FIG. 8A to FIG. 8D), Split-A3B (FIG. 8A to FIG. 8D), and the adenine base editing system Split-ABE8e (FIG. 9A to FIG. 9C and FIG. 10A to FIG. 10D), the first and second deaminase polypeptide fragments can also be seamlessly fused into an intact nucleobase deaminase.

In some less preferred embodiments, in the cytosine base editing system Split-AID10-N5-C4 (FIG. 2) and the adenine base editing system Split-ABE8e-N7-C2 (FIG. 9A to FIG. 9C), the first and second deaminase polypeptide fragments partially overlap with each other, and the fusion protein produced by fusing the first and second deaminase polypeptide fragments has a longer amino acid sequence than the original nucleobase deaminase.

The working model is as follows: When the gRNA is co-expressed with the base editing fusion proteins A and B, the gRNA guides the assembly of the base editing fusion proteins A and B into an intact BE, and the three together constitute a RNP. Then RNP binds to a target gene locus under the guidance of the same gRNA, resulting in nucleotide substitutions from one or more C bases to T bases (cytosine base editing system) or nucleotide substitutions from one or more A bases to G bases (adenine base editing system) of target gene sequence.

The embodiments provided in the present application prove that, while maintaining a robust DNA on-targeting efficiency, the above preferred solutions such as the cytosine base editing system Split-AID10 exhibits near-background level of genome-wide off-target edits, which are significantly lower than those caused by traditional BEs such as BE3 (also referred to as "N-BE3" in the present application), in plants such as rice, fungi such as yeasts, and mammalian cells such as HEK293T cells. While maintaining a robust DNA on-targeting efficiency, the above preferred cytosine base editing system Split-BE3 also exhibits near-background level of genome-wide off-target edits, which is significantly lower than those caused by BE3, in representative eukaryotic organisms such as yeasts and human HEK293T cells. The above preferred adenine base editing system Split-ABE8e also has wide species adaptability, and can allow efficient adenine base editing for endogenous target sites in eukaryotic organisms such as unicellular eukaryotic yeasts, higher plants such as *Arabidopsis thaliana* and rice, and even human HEK293T lines.

Example 1 Evaluation of on-target and off-target editing efficiencies by split complementary cytosine base editing systems in rice as a monocotyledon model plant.

1. Experimental Materials: Wild-Type Rice Variety, *Oryza sativa* L. Ssp. *japonica* ZHI1.

2. Construction of Transient Expression Vectors of BEs in Rice Protoplasts

An expression vector pHBT-rAPOBEC1-nCas9-UGI for N-BE3 (or BE3) was independently constructed in the laboratory, where the promoter is the maize ZmUbi-1 promoter and the terminator was the nopaline synthase (NOS) terminator.

The Split-AID10 expression systems are composed of a Split-AID10-N expression vector and a Split-AID10-C expression vector. A polynucleotide sequence encoding the polypeptide fragment having an amino acid sequence shown in SEQ ID NO: 15 (Split-AID10-N) was commercially synthesized by Sangon Biotech Co., Ltd., simply degested by restriction endonucleases, and then fused to the above pHBT vector to obtain an expression vector pHBT-Split-AID10-N. A construction process of the pHBT-Split-AID10-C vector was basically the same as the construction process of the pHBT-Split-AID10-N, and the pHBT-Split-AID10-C vector carried a polynucleotide sequence encoding the polypeptide fragment having an amino acid sequence shown in SEQ ID NO: 16 (Split-AID10-C).

The Split-AID10-N5-C4 expression systems are composed of the expression vector pHBT-Split-AID10-N5 and the expression vector pHBT-Split-AID10-C4. The construction methods are the same as those of the Split-AID10, and the amino acid sequence of Split-AID10-N5 is shown in SEQ ID NO: 17 and the amino acid sequence of Split-AID10-C4 is shown in SEQ ID NO: 18.

Construction of the nSaCas9 expression vector: The polynucleotide sequence encoding plant codon-optimized SaCas9 was gifted from professor Puchta Holger, Germany (in a published paper[7]). Using the site-directed mutagenesis kit (Mut Express II Fast Mutagenesis Kit V2, #C214-01) purchased from Nanjing Vazyme Biotech Co., Ltd., a D10A amino acid substitution into SaCas9 sequence mentioned above was carried out to obtain the polynucleotide sequence encoding nSaCas9 (D10A). Finally, the expression vector pHBT-nSaCas9 was constructed through simple cut and ligate cloning methods.

3. Construction of Transient Expression Vectors for gRNAs in Rice

With reference to the methods described in published papers[8, 9], the following eight gRNA expression vectors were constructed based on pUC119-OsU6apro-sgRNA[9]; PUC119-OsAAT1-sgRNA, pUC119-OsCDC48-sgRNA, pUC119-OsNAL1-sgRNA, pUC119-OsPDS1-sgRNA, pUC119-OsCDC48-Sa-gRNA, pUC119-OsNRT1.1B-Sa-gRNA, pUC119-OsDEP1-Sa-gRNA, and pUC119-OsAAT1-Sa-gRNA. Target sequence information of gRNAs is shown in Table 1.

TABLE 1

| Cas9 type | Target gene | Target sequence (5'-3') |
|---|---|---|
| SpCas9 | OsAAT1 | CAAGGATCCCAGCCCCGTGAAGG (SEQ ID NO: 38) |
| | OsNAL1 | ACCGTCACGACTGTAGTTAGGGG (SEQ ID NO: 39) |
| | OsCDC48 | TAGCACCCATGACAATGACATGG (SEQ ID NO: 40) |
| | OsPDS | GTTGGTCTTTGCTCCTGCAGAGG (SEQ ID NO: 41) |
| | OsSWEET11 | TGTACACCACCAAAAGTGGAGGG (SEQ ID NO: 42) |
| | OsSWEET13 | GGAGTTGTGGTGCTTTATATAGG (SEQ ID NO: 43) |
| | OsSWEET14 | GCTTAGCACCTGGTTGGAGGGGG (SEQ ID NO: 44) |
| | OsSLR1 | CCCCTCGGACCTCTCCTCCTGGG (SEQ ID NO: 45) |
| | OsACC | CATAGCACTCAATGCGGTCTGGG (SEQ ID NO: 46) |
| | OsDEP1 | AGACAAGCTTGGCCCTCTTTGGG (SEQ ID NO: 47) |
| | OsNRT1.1B | ACTAGATATCTAAACCATTAAGG (SEQ ID NO: 48) |
| | AtALS | TCTCCATTGATGCACCTCCAGGG (SEQ ID NO: 49) |
| | AteTM166 | TCCCCATTTAGCGTCATCAATGG (SEQ ID NO: 50) |
| | AtFLS2 | GGAATCACCTGCGATAGTACCGG (SEQ ID NO: 51) |
| | AtABI3 | TGCACGAGAAGTGGCACACTCGG (SEQ ID NO: 52) |
| | AtBAK1 | ACGGGTGGATACGCGTTGAGAGG (SEQ ID NO: 53) |
| | AtPDS3 | CCTCCAGATAGCTGCATGGAAGG (SEQ ID NO: 54) |
| SaCas9 | OsCDC48 | CTCGTTCCCATGTCATTGTCATGGGT (SEQ ID NO: 55) |
| | OsDEP1 | TGGTCACTCAGCCTGCAGTACTGAAT (SEQ ID NO: 56) |
| | OsNRT1.1B | GATCATCGACAGGTCGGCGGCGGAGT (SEQ ID NO: 57) |
| | OsAAT1 | AGGTGACGGTCGCGTACAACAAGGAT (SEQ ID NO: 58) |

4. Protoplast Isolation and Transfection in Rice

Isolation of Rice Protoplasts:

(1) 8 d to 10 d-old rice seedlings were prepared through soil culture or aseptic tissue culture under the following conditions: a 12 h light (32° C.)/12 h dark (28° C.) cycle, light: 200 µmol·m$^{-2}$·s$^{-1}$, and 70% humidity.

(2) 15 mL of an enzyme solution (1.5% cellulase R10, 0.4% pectinase R10, 0.4 M mannitol, 20 mM MES pH 5.7, 20 mM KCl, 10 mM CaCl$_2$), and 0.1% BSA) was prepared, filtered through a filter membrane with 0.45 μm pore size using a syringe, and added to a petri dish with a diameter of 10 cm.

(3) About 200 healthy and light-green rice seedlings were selected, and leaf sheaths were collected and cut by a blade into 0.5 mm to 1 mm-long stem segments.

(4) The stem segments were placed in the enzyme solution and scattered with an inoculation loop to avoid adhesion to make each stem segment completely immersed in the enzyme solution, and then the petri dish was placed on a horizontal shaker at 50 rpm to 60 rpm to allow digestion in the dark for 3 h.

(5) After the digestion step was completed, 10 mL of a W5 (154 mM NaCl, 125 mM $CaCl_2$), 5 mM KCl, and 2 mM MES pH 5.7) solution was added to the petri dish, the petri dish was shaken with an appropriate strength to make protoplasts released into the solution to obtain a light-green enzymatic hydrolysate solution, the light-green enzymatic hydrolysate solution was filtered through a nylon membrane with 45 μm pore size to obtain a filtrate, and the filtrate was collected in a round-bottom centrifuge tube.

(6) The filtrate was centrifuged in a horizontal centrifuge at 150 g for 5 min to obtain supernatant and light-green protoplast pellets, and the supernatant was removed as much as possible by a vacuum pump.

(7) 10 mL of the W5 solution was slowly added to the round-bottom centrifuge tube, and the round-bottom centrifuge tube was gently shaken to resuspend protoplasts and then allowed to stand on ice for 0.5 h to 1 h.

(8) The W5 solution was removed as much as possible without touching the protoplast pellet after horizontal centrifugation at 150 g for 3 min. Protoplasts at $2\times10^6$ $ml^{-1}$ were re-suspended in MMG solution (0.4 M mannitol, 15 mM $MgCl_2$, and 4 mM MES, pH5.7) kept at room temperature. The protoplast concentration was determined under the microscope with a hemocytometer.

DNA Transfection in Rice Protoplasts:

30 μL (66 μg) plasmid DNA, 300 μL rice protoplasts and 330 μL PEG (40% PEG4000 (v/v), 0.2 M mannitol, and 0.1 M $CaCl_2$)) buffer were added successively to the bottom of a 2 mL round-bottom tube, and then mixed quickly but gently; the mixture was incubated for 15 min in the dark; 1.2 mL W5 solution was added to the mixture, and the reaction was stopped by gently inverting the tube until it was completely mixed; the mixture obtained was centrifuged horizontally at 200 g for 5 min and the supernatant was carefully removed; 150 μL W5 solution was added and protoplasts were resuspended gently; the suspended protoplasts were transferred into 1 mL WI solution and incubated at room temperature for 48 h; After horizontal centrifugation at 250 g for 5 min and removal of supernatant, the transfected pale-yellow rice protoplasts would be gathered at the bottom of the tube; and the tube was quickly frozen in liquid nitrogen and stored at −80° C.

5. Deep Sequencing and Base Substitution Analysis in Rice Protoplasts (1) A DNAquick Plant System (#4992710) purchased from TIANGEN BIOTECH (BEIJING) CO., LTD. was used to extract genomic DNA from rice protoplasts.

(2) Specific primers with barcodes were designed to conduct a first round PCR to obtain fragments about 200 bp upstream and downstream of a target sequence, and based on products of the first round PCR, a second round PCR was conducted with universal primers. Primers are shown in Table 2.

(3) Products of the second round PCR were mixed in equal molar, purified, and sent to Beijing Novogene Co., Ltd. for amplicon sequencing. Paired-end 150 bp (PE150) sequencing was conducted on the illumina NovaSeq platform.

(4) Sequencing data was demultiplexed according to barcodes on a public data analysis platform (usegalaxy.org/)[10], and finally the base editing efficiencies of target sites were analyzed on the CRISPResso2[11] or BE-Analyzer[12] website. The base substitution rates on target sites were presented by Excel.

TABLE 2

Primer information

| Primer name | Primer sequence (5'-3') | Application |
| --- | --- | --- |
| D501-2nd-F | AATGATACGGCGACCACCGAGATCTACACTATAGCCTACACTCTT TCCCTACACGACGCTCTTCCGA (SEQ ID NO: 59) | Deep sequencing and |
| D701-2nd-R | CAAGCAGAAGACGGCATACGAGATCGAGTAATGTGACTGGAGTT CAGACGTGTGCTCTTCCGAT (SEQ ID NO: 60) | DNA library construction |
| OsAAT1-1st-F | GGAGTTCAGACGTGTGCTCTTCCGATCTGTCAAATCCACCACCAA TCCAATCC (SEQ ID NO: 61) | Amplifying the OsAAT1 target region for the |
| OsAAT1-1st-R | TTTCCCTACACGACGCTCTTCCGATCTNNNNNNNGCTCGACCTGAT CGGTGCTC (SEQ ID NO: 62) | orthogonal R-loop assay in rice |
| OsCDC48-1st-F | TTTCCCTACACGACGCTCTTCCGATCTNNNNNNNCCATGGAGAAGT TGAGAGGCG (SEQ ID NO: 63) | Amplifying the OsCDC48 target region for the |
| OsCDC48-1st-R | GGAGTTCAGACGTGTGCTCTTCCGATCTCAGGAACACCAATGTC AATCTCCC (SEQ ID NO: 64) | orthogonal R-loop assay in rice |
| OsNRT1.1B-1st-F | TTTCCCTACACGACGCTCTTCCGATCTNNNNNNAAGGTAATAATC ATTGACGTGTTTGG (SEQ ID NO: 65) | Amplifying the OsNRT1.1B target region |
| OsNRT1.1B-1st-R | GGAGTTCAGACGTGTGCTCTTCCGATCTCAGAACATGATGGTGGT CGC (SEQ ID NO: 66) | for the orthogonal R-loop assay in rice |
| OsPDS-1st-F | TTTCCCTACACGACGCTCTTCCGATCTNNNNNNGCCTACTGAACG GTTTTCTTTCC (SEQ ID NO: 67) | Amplifying the OsPDS target region for the |
| OsPDS-1st-R | GGAGTTCAGACGTGTGCTCTTCCGATCTTGATCAGCAGCAATTTC ATCAGG (SEQ ID NO: 68) | orthogonal R-loop assay in rice |

TABLE 2-continued

Primer information

| Primer name | Primer sequence (5'-3') | Application |
|---|---|---|
| OsDEP1-1st-F | TTTCCCTACACGACGCTCTTCCGATCTNNNNNNTCTGCAACTGTGTCTTTTAACATGA (SEQ ID NO: 69) | Amplifying the OsDEP1 target region for the orthogonal R-loop assay in rice |
| OsDEP1-1st-R | GGAGTTCAGACGTGTGCTCTTCCGATCTCTACCTGTTGAAGTAAAATAGACTATGC (SEQ ID NO: 70) | |
| OsNAL1-1st-F | TTTCCCTACACGACGCTCTTCCGATCTNNNNNNTATGCCGCCCCATTATGGAT (SEQ ID NO: 71) | Amplifying the OsNAL1 target region for the orthogonal R-loop assay in rice |
| OsNAL1-1st-R | GGAGTTCAGACGTGTGCTCTTCCGATCTCCCTATGAGGCTATTGAGCGG (SEQ ID NO: 72) | |
| AtFLS2-1st-F | TTTCCCTACACGACGCTCTTCCGATCTNNNNNNAGAATGGTATTTCCAACGACCCT (SEQ ID NO: 73) | Amplifying the AtFLS2 target region for adenine base editing |
| AtFLS2-1st-R | GGAGTTCAGACGTGTGCTCTTCCGATCTGAAGTGAGATCAAGAACCTGGA (SEQ ID NO: 74) | |
| OsSWEEET11-F | TGATTGCACACGAACTACTCTG (SEQ ID NO: 75) | Detection of base editing outcomes at the OsSWEEET11 site in transgenic rice |
| OsSWEEET11-R | GCAATGGTGCAGACAACAACTA (SEQ ID NO: 76) | |
| OsSWEEET13-F | TCGATCTCTACTGACAATGCAC (SEQ ID NO: 77) | Detection of base editing outcomes at the OsSWEEET13 site in transgenic rice |
| OsSWEEET13-R | AGTACCATCCATATTGCCTTCG (SEQ ID NO: 78) | |
| OsSW13-OT1-F | ATGGTGACGAAATCGAACCG (SEQ ID NO: 79) | Detection of base editing outcomes at the off-target site 1 related to the OsSWEEET13 site in transgenic rice |
| OsSW13-OT1-R | ACGACCGATTTACCAACAGG (SEQ ID NO: 80) | |
| OsSW13-OT2-F | GTTATCTCGTGCAGATAGGCTG (SEQ ID NO: 81) | Detection of base editing outcomes at the off-target site 2 related to the OsSWEEET13 site in transgenic rice |
| OsSW13-OT2-R | CTCGAGCCGAGCCTATAACGA (SEQ ID NO: 82) | |
| OsSWEEET14-F | GCCCAACTCTAGATCCCTTAAC (SEQ ID NO: 83) | Detection of base editing outcomes at the OsSWEEET14 site in transgenic rice |
| OsSWEEET14-R | CCACTCACAATTGCATCCAAAA (SEQ ID NO: 84) | |
| OsSLR1-F | AGCTAGGTAGGTTTGGGGGAGG (SEQ ID NO: 85) | Detection of base editing outcomes at the OsSLR1 site in transgenic rice |
| OsSLR1-R | TGGAAGCATGGCGGG (SEQ ID NO: 86) | |
| OsACC-F | AGACTCAGACCATGATGCAAACT (SEQ ID NO: 87) | Detection of adenine base editing outcomes at the OsACC site in transgenic rice |
| OsACC-R | AAGCAACAAAAGCATCGTCATCA (SEQ ID NO: 88) | |
| OsDEP1-ABE-F | TCGTCTTCCTTTGACTTTACCGA (SEQ ID NO: 89) | Detection of adenine base editing outcomes at the OsDEP1 site in transgenic rice |
| OsDEP1-ABE-R | TAAAAGCACAGCACAGTGTCAAG (SEQ ID NO: 90) | |
| OsNRT1.1B-ABE-F | TAGCAAGCCAGGTTGTAGGAAAA (SEQ ID NO: 91) | Detection of adenine base editing outcomes at the OsNRT1,1B site in transgenic rice |
| OsNRT1.1B-ABE-R | TAGCAACTCCTACTCTGCTTTGG (SEQ ID NO: 92) | |
| AtALS-F | TTTCTCCTGAACCATGGCGG (SEQ ID NO: 93) | Detection of base editing outcomes at the AtALS site in transgenic *Arabidopsis* |
| AtALS-R | GACGAGGGACTTGTCCTGTG (SEQ ID NO: 94) | |
| AteTM166-F | AGTCTCCACATGAGACCTTTAGTG (SEQ ID NO: 95) | Detection of base editing outcomes at the AteTM166 site in transgenic *Arabidopsis* |
| AteTM166-R | CACCTTTATCCCACACCCCA (SEQ ID NO: 96) | |
| AtABI3-F | TTGATACGAGGGGTTAAAGTAAGAC (SEQ ID NO: 97) | Detection of base editing outcomes at the AtABI3 site in transgenic *Arabidopsis* |
| AtABI3-R | AAACGATATGTAAGCTCGACTC (SEQ ID NO: 98) | |

TABLE 2-continued

Primer information

| Primer name | Primer sequence (5'-3') | Application |
|---|---|---|
| AtPDS3-F | TCTTCAGTCTTGTGCTACACACC (SEQ ID NO: 99) | Detection of base editing outcomes at the AtPDS3 site in transgenic *Arabidopsis* |
| AtPDS3-R | ACATTCGGATAAGCACCGACTTC (SEQ ID NO: 100) | |
| AtBAK1-F | CCTTGCTCTCGGCGATAACT (SEQ ID NO: 101) | Detection of base editing outcomes at the AtBAK1 site in transgenic *Arabidopsis* |
| AtBAK1-R | AGAAAGGGGAAACCTTCGGC (SEQ ID NO: 102) | |
| ScAde1-1-F | TCGTCGGCAGCGTCAGATGTGTATAAGAGACAGGAGGTAGACGCTGGTACGTTGC (SEQ ID NO: 103) | Amplification of the Ade1-1 target region in *Saccharomyces cerevisiae* |
| ScAde1-1-R | GTCTCGTGGGCTCGGAGATGTGTATAAGAGACAGGTCTTACCTGGGGCGATGTCGA (SEQ ID NO: 104) | |
| ScAde1-3-F | TCGTCGGCAGCGTCAGATGTGTATAAGAGACAGCTCAAGAGTTCCCAGAACCAATC (SEQ ID NO: 105) | Amplification of the Ade1-3 target region in *Saccharomyces cerevisiae* |
| ScAde1-3-R | GTCTCGTGGGCTCGGAGATGTGTATAAGAGACAGAGTGTCTGCGATGATGATGCC (SEQ ID NO: 106) | |
| ScCan1-1-F | TCGTCGGCAGCGTCAGATGTGTATAAGAGACAGGCATTTGGTGCGGCCAATGG (SEQ ID NO: 107) | Amplification of the Can1-1 target region in *Saccharomyces cerevisiae* |
| ScCan1-1-R | GTCTCGTGGGCTCGGAGATGTGTATAAGAGACAGGGAAGCGACCCAGAACTCGA (SEQ ID NO: 108) | |
| ScCan1-5-F | TCGTCGGCAGCGTCAGATGTGTATAAGAGACAGTCGAGTTCTGGGTCGCTTCC (SEQ ID NO: 109) | Amplification of the Can1-5 target region in *Saccharomyces cerevisiae* |
| ScCan1-5-R | GTCTCGTGGGCTCGGAGATGTGTATAAGAGACAGCCTTGAAATGTGAAGGCAGCG (SEQ ID NO: 110) | |
| ScCan1-9-F | TCGTCGGCAGCGTCAGATGTGTATAAGAGACAGGAAGACGCCGACATAGAGGAGAAG (SEQ ID NO: 111) | Amplification of the Can1-9 target region in *Saccharomyces cerevisiae* |
| ScCan1-9-R | GTCTCGTGGGCTCGGAGATGTGTATAAGAGACAGCACCTATGCCATCCTCCATAGAGA (SEQ ID NO: 112) | |
| ScPolyC1-F | TCGTCGGCAGCGTCAGATGTGTATAAGAGACAGCTTCCGCTATTAGGGGACTG (SEQ ID NO: 113) | Amplification of the PolyC-1 target region in *Saccharomyces cerevisiae* |
| ScPolyC1-R | GTCTCGTGGGCTCGGAGATGTGTATAAGAGACAGCCGTGCGCGTAATCCTTCTC (SEQ ID NO: 114) | |
| ScPolyC2-F | TCGTCGGCAGCGTCAGATGTGTATAAGAGACAGCAGTCAGCAATATGCTCCACCA (SEQ ID NO: 115) | Amplification of the PolyC-2 target region in *Saccharomyces cerevisiae* |
| ScPolyC32-R | GTCTCGTGGGCTCGGAGATGTGTATAAGAGACAGCTGGGGTGGACCGTACATATTG (SEQ ID NO: 116) | |
| ScPolyC3-F | TCGTCGGCAGCGTCAGATGTGTATAAGAGACAGATTATCATCGCCACTTGGCATTG (SEQ ID NO: 117) | Amplification of the PolyC-3 target region in *Saccharomyces cerevisiae* |
| ScPolyC3-R | GTCTCGTGGGCTCGGAGATGTGTATAAGAGACAGCAATTGAATCGTGCCAACCTGAC (SEQ ID NO: 118) | |
| ScPolyC4-F | TCGTCGGCAGCGTCAGATGTGTATAAGAGACAGAAGCGGTGCACCTTACAACAGTGC (SEQ ID NO: 119) | Amplification of the PolyC-4 target region in *Saccharomyces cerevisiae* |
| ScPolyC4-R | GTCTCGTGGGCTCGGAGATGTGTATAAGAGACAGCGGTATGAGTTGAGGAGGAGACTC (SEQ ID NO: 120) | |
| ScPolyC5-F | TCGTCGGCAGCGTCAGATGTGTATAAGAGACAGCCGCATGCTAACCAGTTCGT (SEQ ID NO: 121) | Amplification of the PolyC-5 target region in *Saccharomyces cerevisiae* |
| ScPolyC5-R | GTCTCGTGGGCTCGGAGATGTGTATAAGAGACAGGCGGATAGTACCTTCTGCCG (SEQ ID NO: 122) | |
| ScPolyC6-F | TCGTCGGCAGCGTCAGATGTGTATAAGAGACAGGAAGACGCCGACATAGAGGAGAAG (SEQ ID NO: 123) | Amplification of the PolyC-6 target region in *Saccharomyces cerevisiae* |
| ScPolyC6-R | GTCTCGTGGGCTCGGAGATGTGTATAAGAGACAGCACCTATGCCATCCTCCATAGAGA (SEQ ID NO: 124) | |
| Hs-Site7-F | TCGTCGGCAGCGTCAGATGTGTATAAGAGACAGCTTGTCTGTCCAAGGAGAATGAGGTC (SEQ ID NO: 125) | Amplification of the Site-7 target region in HEK293T cells |
| Hs-Site7-R | GTCTCGTGGGCTCGGAGATGTGTATAAGAGACAGAGAACCCGCTGCTAGAGACTCCA (SEQ ID NO: 126) | |
| Site7-OT-F | TCGTCGGCAGCGTCAGATGTGTATAAGAGACAGCGGCTGCTCTCACATGCTCTAG (SEQ ID NO: 127) | Amplification of the Cas9-dependent off-target site Site7-OT region in HEK293T cells |
| Site7-OT-R | GTCTCGTGGGCTCGGAGATGTGTATAAGAGACAGGGCATGGTTTGCCTCGTCCAGG (SEQ ID NO: 128) | |

TABLE 2-continued

Primer information

| Primer name | Primer sequence (5'-3') | Application |
|---|---|---|
| Hs-site 14-F | TCGTCGGCAGCGTCAGATGTGTATAAGAGACAGGGGCTATCAAA CCTCATGATTGGC (SEQ ID NO: 129) | Amplification of the Site-14 target region in HEK293T cells |
| Hs-site 14-R | GTCTCGTGGGCTCGGAGATGTGTATAAGAGACAGACACACAGAC ACTGCAGAGAATAACA (SEQ ID NO: 130) | |
| Hs-site 17-F | TCGTCGGCAGCGTCAGATGTGTATAAGAGACAGGCTGCTGGAAT ACCGAGGAC (SEQ ID NO: 131) | Amplification of the Site-17 target region in HEK293T cells |
| Hs-site 17-R | GTCTCGTGGGCTCGGAGATGTGTATAAGAGACAGGCAACTCTCTT TTCTCGGGA (SEQ ID NO: 132) | |
| Hs-site21-F | TCGTCGGCAGCGTCAGATGTGTATAAGAGACAGGGGTCCAAAGC AGGATGACA (SEQ ID NO: 133) | Amplification of the Site-21 target region in HEK293T cells |
| Hs-site21-R | GTCTCGTGGGCTCGGAGATGTGTATAAGAGACAGCCTTTCAACCC GAACGGAGA (SEQ ID NO: 134) | |
| Site21-OT-F | TCGTCGGCAGCGTCAGATGTGTATAAGAGACAGCCAGGCTCTTA CTGAGAAGGCC (SEQ ID NO: 135) | Amplification of the Cas9-dependent off-target site Site21-OT region in HEK293T cells |
| Site21-OT-F | GTCTCGTGGGCTCGGAGATGTGTATAAGAGACAGTCCTGCTCACC TGCTGCTCTG (SEQ ID NO: 136) | |
| Hs-site23-F | TCGTCGGCAGCGTCAGATGTGTATAAGAGACAGCAGGCAGGCAG GCTCTCCGA (SEQ ID NO: 137) | Amplification of the Site-23 target region in HEK293T cells |
| Hs-site23-R | GTCTCGTGGGCTCGGAGATGTGTATAAGAGACAGCAGAGTGCTG CTTGCTGCTGG (SEQ ID NO: 138) | |
| Site23-OT-F | TCGTCGGCAGCGTCAGATGTGTATAAGAGACAGGGACTGCCTTG CTCTCACCAG (SEQ ID NO: 139) | Amplification of the Cas9-dependent off-target site Site23-OT region in HEK293T cells |
| Site23-OT-R | GTCTCGTGGGCTCGGAGATGTGTATAAGAGACAGGGCCCTGCCA CATGCCTCTG (SEQ ID NO: 140) | |
| Hs-site27-F | TCGTCGGCAGCGTCAGATGTGTATAAGAGACAGCAAACCTGACA AGGGGATTGCGG (SEQ ID NO: 141) | Amplification of the Site-27 target region in HEK293T cells |
| Hs-site27-R | GTCTCGTGGGCTCGGAGATGTGTATAAGAGACAGGTCACCAACT GGGTGTCCAACA (SEQ ID NO: 142) | |
| Site27-OT-F | TCGTCGGCAGCGTCAGATGTGTATAAGAGACAGGAAGAAGCTGT GAGAGTTCCCAAC (SEQ ID NO: 143) | Amplification of the Cas9-dependent off-target site Site27-OT region in HEK293T cells |
| Site27-OT-R | GTCTCGTGGGCTCGGAGATGTGTATAAGAGACAGGTCCCACACC AACCAATTCTCCA (SEQ ID NO: 144) | |
| HEK-Site1-F | CCAACTGGTAACCCACAAAGCC (SEQ ID NO: 145) | Amplification of the HEK Site1 target region in HEK293T cells |
| HEK-Site1-R | GATTACAGCCTGAGCCACCGTG (SEQ ID NO: 146) | |
| HEK-Site2-F | CCTCCATCTTCTCCGCAGACAG (SEQ ID NO: 147) | Amplification of the HEK Site2 target region in HEK293T cells |
| HEK-Site2-R | CCTCATGCCACCTGAGACACAT (SEQ ID NO: 148) | |
| Nextera_i5_adator | AATGATACGGCGACCACCGAGATCTACACNNNNNNNNNTCGTCGG CAGCGTCAGATGTGTA (SEQ ID NO: 149) | Adapter primers for the amplicon deep sequencing of the second round of DNA library construction |
| Nextera_i7_adator | CAAGCAGAAGACGGCATACGAGATNNNNNNNNGTCTCGTGGGC TCGGAGATGTGTATAAG (SEQ ID NO: 150) | |

6. High-Throughput Specificity Detection of BEs Via the Orthogonal R-Loop Assay

It refers to the method described in the published paper [13]. In this example, 8 rice target sites were selected, including 4 on-target sites targeted by gRNAs of SpCas9 (OsAAT1, OsCDC48, OsNAL1, and OsPDS1) and 4 off-target sites targeted by gRNAs of nSaCas9 (OsCDC48, OsNRT1.1B, OsDEP1, and OsAAT1). In order to simulate actual working conditions of BEs in cells, the above target sites were randomly grouped according to the corresponding relation between SpCas9 and SaCas9, and the following four combinations were obtained: Sp-OsAAT1 and Sa-OsCDC48, Sp-OsCDC48 and Sa-OsNRT1.1B, Sp-OsNAL1 and Sa-OsDEP1, and Sp-OsPDS1 and Sa-OsAAT1. During a test for each combination, each treatment group of rice protoplasts needed to be transfected with BE plasmids (in particular, for Split-AID10 and Split-AID10-N5-C4, a pHBT-Split-AID10-N(N5) plasmid and a pHBT-Split-AID10-C(C4) plasmid needed to be transfected at equal amounts, respectively), a SpCas9 gRNA plasmid (such as pUC119-OsAAT1-sgRNA), a nSaCas9 plasmid (pHBT-nSaCas9), and a nSaCas9 gRNA plasmid (such as pUC119-OsCDC48-Sa-gRNA) at equal amounts. For each treatment group in the test for each combination, deep sequencing and analysis were conducted for SpCas9 (on-target) and nSa-Cas9 target sites (off-target) simultaneously.

7. Construction of Binary Vectors for Rice Transformation and Transformation of Rice (1) The binary vector of BE3 is pH-nCas9-PBE (addgene: #98163), where the promoter was a ZmUbi-1 promoter and the terminator was an E9 terminator. Targeted editing at OsSWEET11/13/14 sites: An expression cassette OsU6apro-OsSWEET14-OsU6bpro-OsSWEET13-OsU6apro-OsSWEET11 of 3 gRNAs was commercially synthesized and fused to the above pH-nCas9-PBE vector through simple restriction digestion and ligation methods (target sequence information is listed in Table 1). Targeted editing at the OsSLR1 site: The expression cassette OsUdapro-OsSLR1 of a single gRNA was commercially synthesized and fused to the above pH-nCas9-PBE vector through simple restriction digestion and ligation methods (target sequence information is listed in Table 1).

(2) The binary vector of Split-AID10 was prepared as follows: Step 1: With the pHBT-Split-AID10-N vector as a template, a pH-Split-AID10-N vector was prepared through simple PCR, restriction digestion, and ligation reactions. Step 2: The OsUBQ2 promoter sequence was acquired through PCR from rice Zhonghua 11 genomic DNA, then overlapping PCR reactions were conducted with pHBT-Split-AID10-C and pH-nCas9-PBE vectors as templates to obtain the Split-AID10-C-E9 term polynucleotide sequence, and the OsUBQ2 promoter sequence and the Split-AID10-C-E9 term polynucleotide sequence were fused through simple PCR reactions to obtain an expression cassette of Split-AID10-N: the OsUBQ2 pro-Split-AID10-C-E9 term polynucleotide sequence. Step 3: The expression cassette of Split-AID10-N was inserted after the E9 terminator of the pH-Split-AID10-N vector through simple restriction digestion and ligation to obtain the pH-Split-AID10-N-C binary vector carrying two complete expression cassettes. Two binary vectors targeting target genes OsSWEET11, OsSWEET13 and OsSWEET14 or OsSLR1 were cloned into pH-PIGS-AID10 as described above.

(3) Transformation of rice: The binary vectors were transformed into competent cells of *Agrobacterium tumefaciens* strain EHA 105 through freeze-thaw transformation, and the genetic transformation of rice was subsequently entrusted to Wuhan BioRun Co., Ltd.

8. Experimental Results

Figure 2:
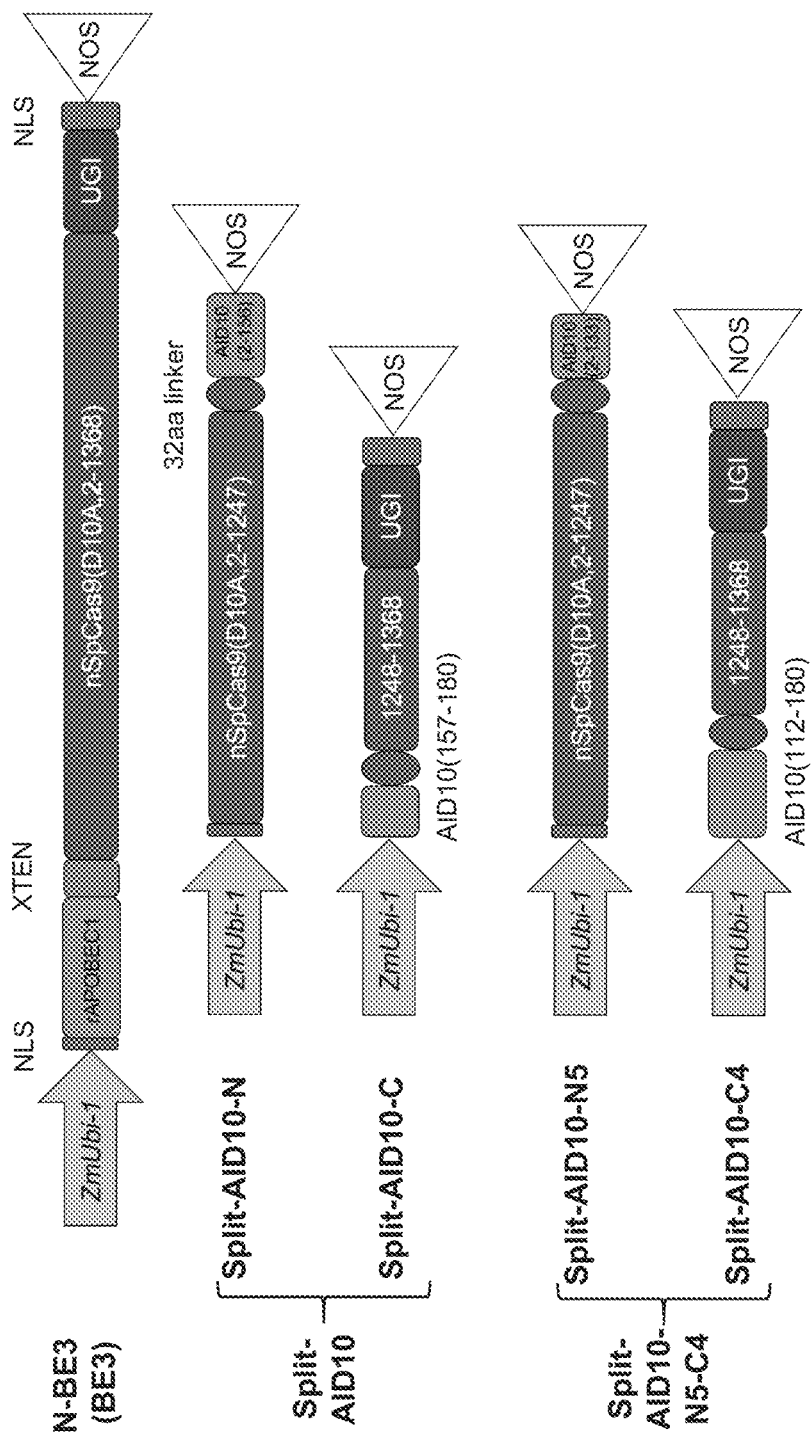
FIG. 2 is a schematic diagram of vectors for transient expression of BEs in rice protoplasts.
Figure 3A:
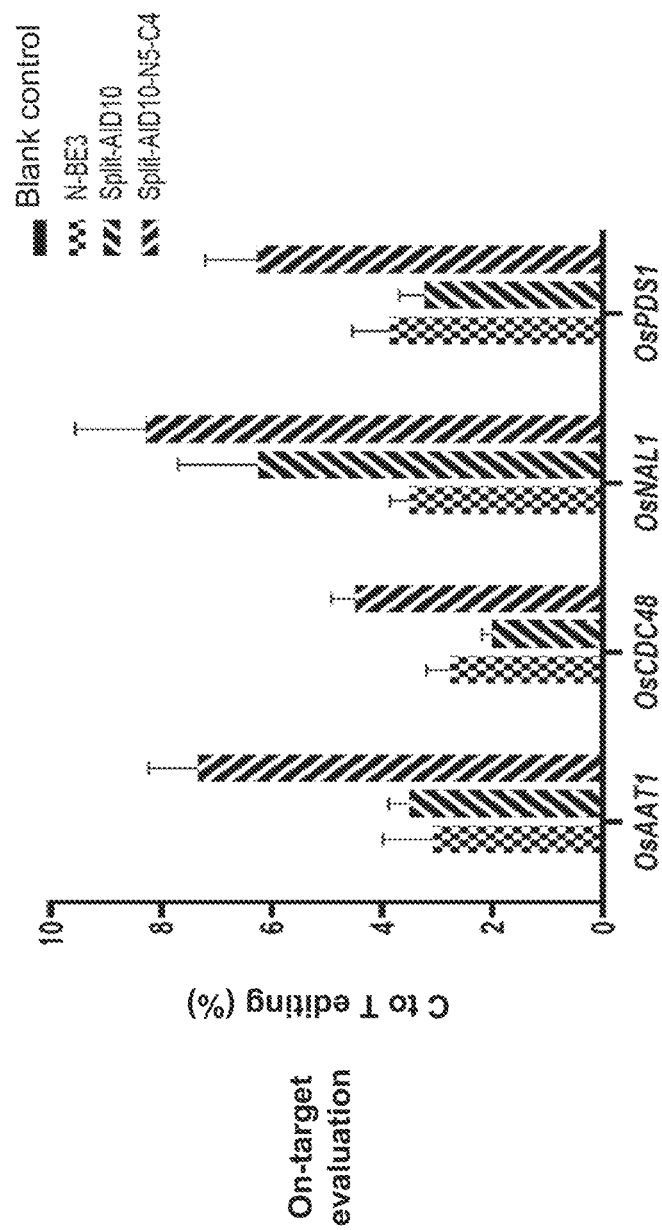
FIG. 3A is a statistical graph of on-target editing efficiencies of various BEs that are evaluated by the Orthogonal R-loop assay in rice protoplasts (n=3)
Figure 3B:
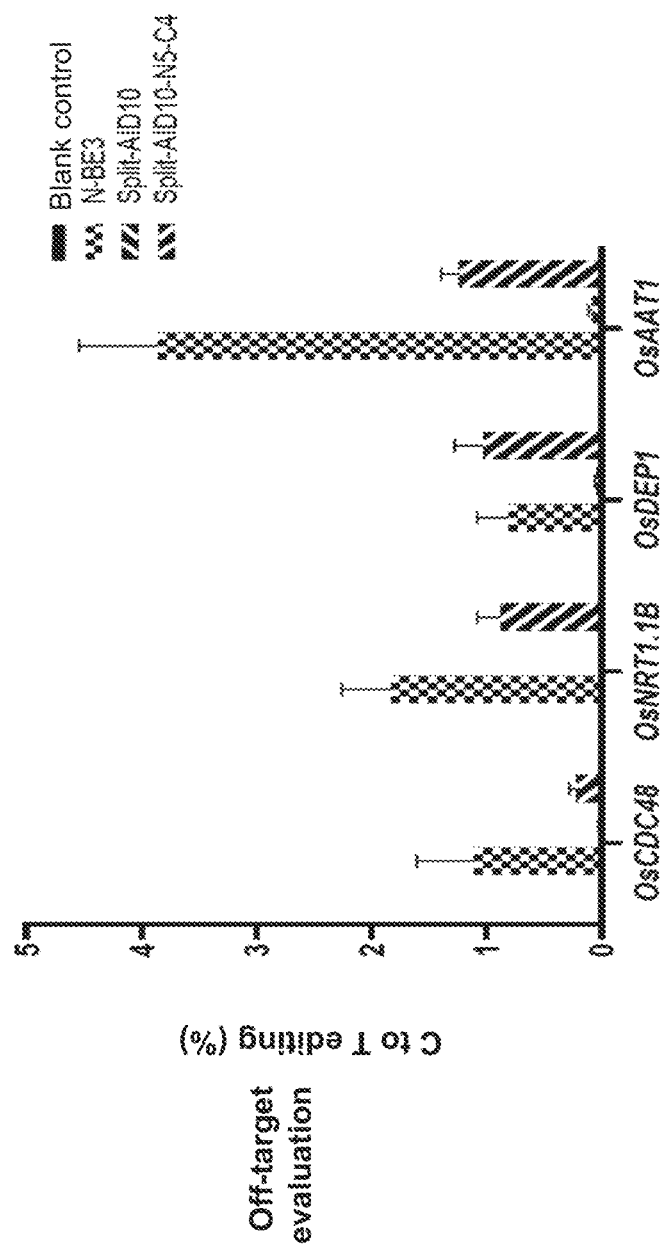
FIG. 3B is a statistical graph of off-target editing efficiencies of various BEs that are evaluated by the Orthogonal R-loop assay in rice protoplasts (n=3)
Figure 3C:
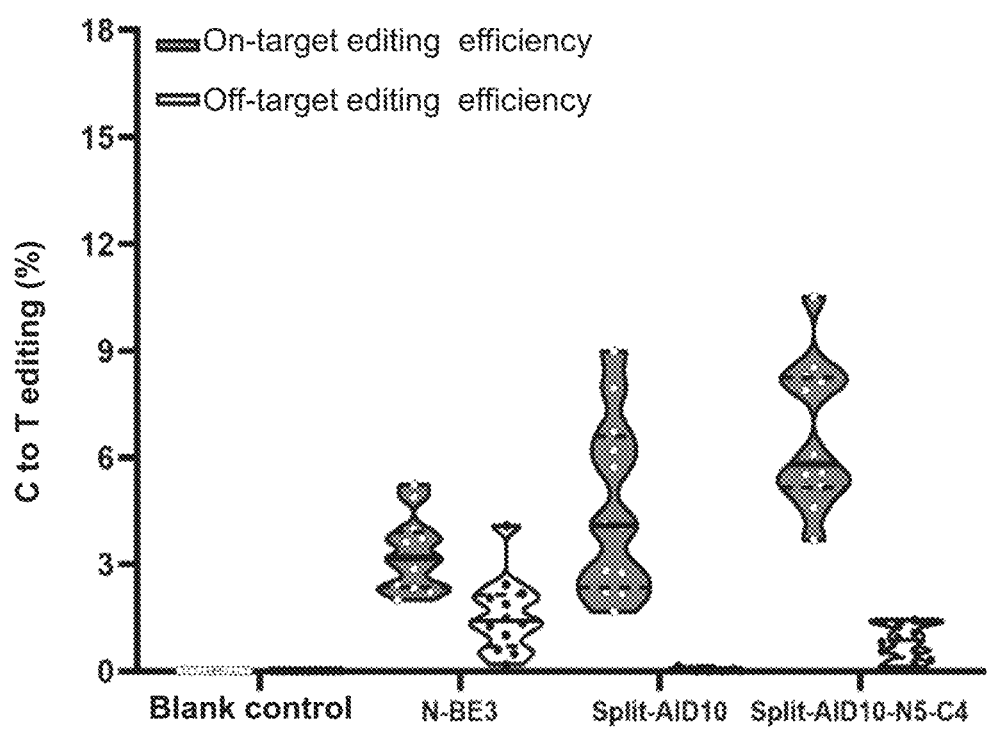
FIG. 3C is a comprehensive statistical graph of FIG. 3A and FIG. 3B (n=12)

The above method based on the orthogonal R-loop assay (FIG. 3A and FIG. 3B) was used to evaluate on-target and off-target editing efficiencies of the two split complementary cytosine base editing systems Split-AID10 and Split-AID10-N5C4 in rice protoplasts, with the traditional N-BE3 as a control (FIG. 2). In terms of on-target editing, deep sequencing analysis was conducted for genomic regions that four SpCas9 gRNA are targeting. Analysis results showed that Split-AID10 and Split-AID10-N5C4 both could allow the effective base editing at endogenous target sites in rice, and average C-to-T base substitution efficiencies were about 4.6% and 6.6%, respectively, which were greater than the 3.3% of the traditional N-BE3 (BE3) (FIG. 3A and FIG. 3C). In terms of off-target editing, deep sequencing analysis was conducted for four nSaCas9 gRNA target sites. Analysis results showed that average off-target editing efficiencies (0.05% and 0.8%) by Split-AID10 and Split-AID10-N5C4 at four sites were significantly lower than the average off-target editing efficiency by the traditional BE3 (1.6%). In particular, the average off-target editing efficiency of Split-AID10 was merely 0.05%, which was not significantly different with the mutation rate (0.02%) in the blank control (FIG. 3B and FIG. 3C).

Figure 4A:
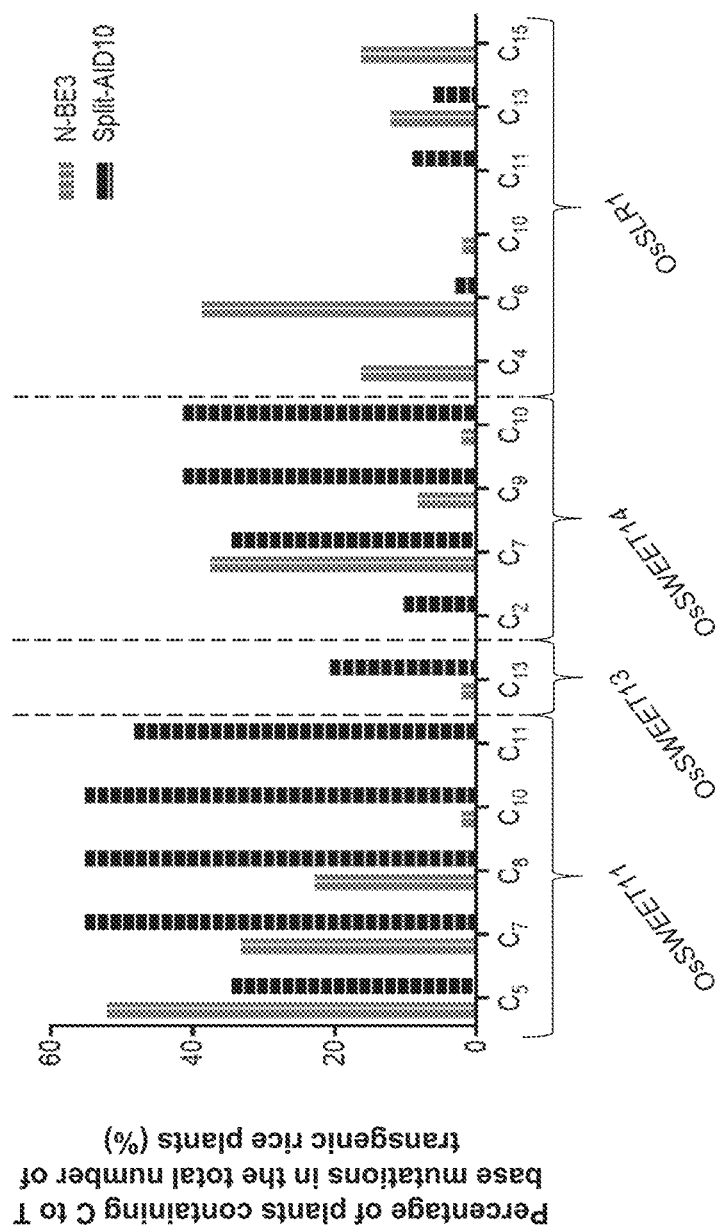
FIG. 4A shows a histogram of on-target editing efficiencies for four endogenous target sites in transgenic rice plants.
Figure 4B:
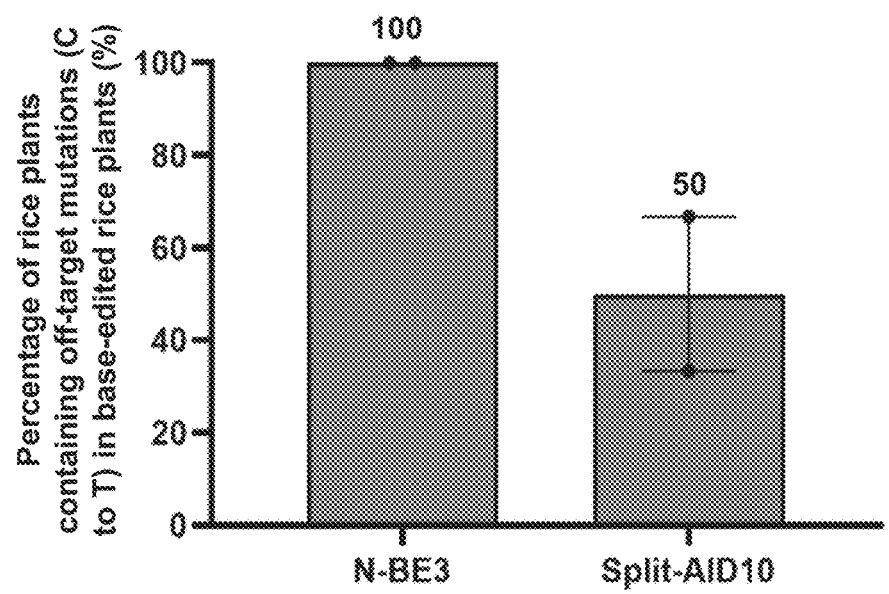
FIG. 4B shows a histogram (n=2) of Cas9-dependent off-target editing efficiencies and an off-target site information table for the comparison of Split-AID10 with two traditional BEs.

Then, the Split-AID10 that performed best in rice protoplasts was co-expressed with gRNAs in transgenic rice, and the traditional N-BE3 was regarded as a control. After obtainment of transgenic rice plants, specific primers were designed for different target gene loci to conduct PCR reactions, and the PCR products were sent to Tsingke Biotech Co., Ltd. for Sanger sequencing. Analysis results for the four target sites showed that Split-AID10 also allowed successful base editing in transgenic rice plants. The effective editing window is $C_5$ to $C_{13}$ on a target sequence (with 21-23 as protospacer adjacent motif (PAM)), and cytosine base substitution efficiencies at different positions ranged from 3% to 55.2% (FIG. 4A). Finally, possible Cas9-dependent off-target sites for all four on-target sites were predicted using the online analysis tool CRISPR-GE (http://skl.scau.edu.cn/). Based on the criterion that an off-target score is larger than 0.7, only two possible off-target sites were successfully predicted for the on-target site OsSWEET13 (FIG. 4B). Then, Sanger sequencing was conducted in terms of 2 off-target sites for 38 transgenic rice plants edited by BE3 or Split-AID10. As shown in FIG. 4B, the above-mentioned Cas9-dependent DNA off-target edits were found in only 50% on-target edited rice plants by Split-AID10, which were significantly less than 100% by BE3.

In summary, two split complementary cytosine base editing systems Split-AID10 and Split-AID10-N5C4 both allow effective base editing in rice. Compared with the traditional BEs such as BE3, Split-AID10 and Split-AID10-N5C4 can significantly reduce genome-wide random off-target effects of base editing (same as "Cas9-independent off-target effects") while maintaining robust on-target editing. Further, Split-AID10 also exhibits a prominent on-target editing efficiency in transgenic rice plants, and can reduce Cas9-dependent off-target edits.

Example 2 The complementary cytosine base editing system Split-AID10 could also be used to allow efficient base editing in transgenic *Arabidopsis thaliana* plants.

1. Experimental Material

Wild-type *Arabidopsis thaliana* used in this example was the Col-0 ecotype.

2. Genetic Transformation of *Arabidopsis thaliana*

The construction of binary vectors for *Arabidopsis* transformation used in this example referred to the methods described in the published article[14] and Example 1. The binary vectors were constructed for two different target sites, individually (target sequence information of gRNAs is listed in Table 1). The binary vectors each were transformed into cells of *Agrobacterium tumefaciens* strain GV3101 through the electric shock method, and then transformed into *Arabidopsis* by the floral dip method. Specifically, the correct *Agrobacterium tumefaciens* cells were inoculated into the kanamycin (50 mg/L)—containing liquid LB medium at a ratio of 1:100 and cultivated in a 28° C. shaker at 220 rpm for 2 d, the resulting bacterial solution was centrifuged at 5,000 g to obtain a bacterial pellet and a supernatant, the supernatant was discarded, and a 5% sucrose solution including 0.05% of Silwet L77 was added to the bacterial pellet for resuspension to obtain an *Agrobacterium tumefaciens* solution. Flowering *Arabidopsis thaliana* plants were taken and inverted to make inflorescences of flowering *Arabidopsis thaliana* plants completely immersed in the *Agrobacterium tumefaciens* solution, gently stirred for about 10 s, then taken out and placed in a moist and dark environment for 1 d, and then transferred to a normal growth environment until mature seeds were harvested.

3. Screening and Genotype Identification of Transgenic Seedlings

The mature seeds harvested above were sown in a sterile ½ MS solid medium including 50 mg/L of hygromycin B in a sterile environment and cultivated for about 10 d, rooted hygromycin-positive seedlings were transplanted to soil and further cultivated for half a month, and leaf genomes were extracted from the transgene-positive seedlings using the rapid plant genome DNA extraction system purchased from TIANGEN BIOTECH (BEIJING) CO., LTD. Primers specific to a target gene were designed to conduct PCR reactions, and PCR products were sent to Tsingke Biotech Co., Ltd. for Sanger sequencing.

4. Experimental Results

Figure 5B:
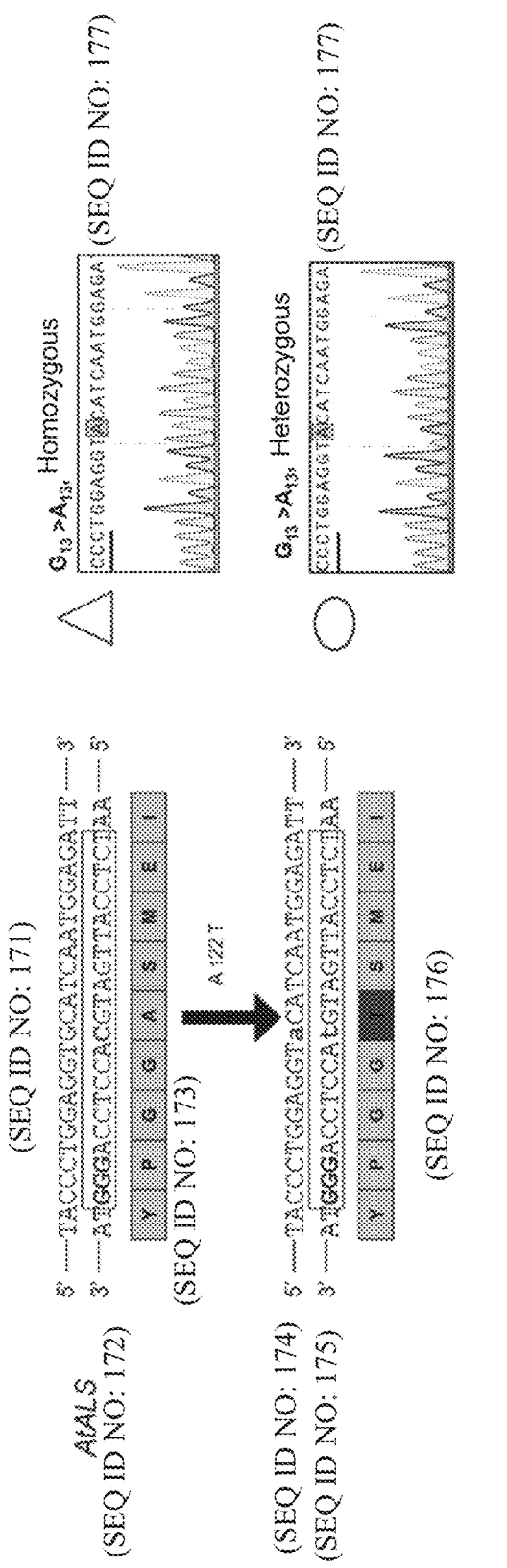
FIG. 5A shows the editing efficiencies among two endogenous sites using Split-AID10 in transgenic Arabidopsis, and FIG. 5B exhibits that the $G_{13}>A_{13}$ mutation in the AtALS target site caused by Split-AID10 led to an A122T amino acid substitution conferring imidazolinone herbicide resistance to Arabidopsis in the T1 generation.
Figure 5B:
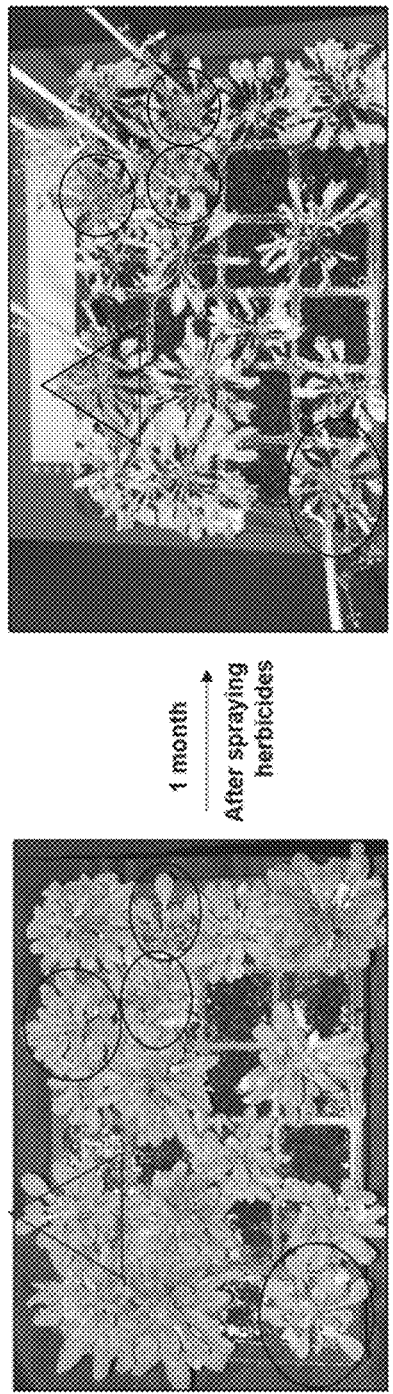

As shown in FIG. 5A, genotypes of transgenic *Arabidopsis thaliana* plants based on two independent endogenous target sites AtALS and AteTM166 were identified, and results showed that Split-AID10 could successfully allow efficient C-to-T base editing in transgenic *Arabidopsis* plants, with an average editing efficiency of 7.7%. As shown in FIG. 5B, in the T1 generation transgenic plants obtained by editing the AtALS site in *Arabidopsis* by Split-AID10, an expected base substitution from $G_{13}$ to $A_{13}$ occurred at the AtALS site, resulting in an amino acid substitution from alanine to threonine (A122T) at position 122 in the coding sequence of the endogenous ALS gene. All 2 month-old T1 generation transgenic *Arabidopsis* plants (with or without base editing) were sprayed with an imidazolinone herbicide (Shandong Cynda Chemical Co., Ltd.), and 1 month later, surviving plants all included the base substitution from $G_{13}$ to $A_{13}$ in the endogenous ALS gene, indicating that the targeted editing at the AtALS site in *Arabidopsis thaliana* by Split-AID10 confers transgenic *Arabidopsis* plants resistance to imidazolinone herbicides. This example proves that Split-AID10 can allow efficient C-to-T base editing in transgenic *Arabidopsis* plants and can provide excellent agronomic traits for *Arabidopsis thaliana* (such as herbicide resistance).

Example 3 The split complementary cytosine base editing systems Split-AID10 and Split-BE3 also exhibited robust on-target editing and an extremely low genome-wide random off-target effects in yeasts.

1. Experimental Material

In this example, the *Saccharomyces cerevisiae* BY4741 strain was adopted.

2. Construction of Expression Vectors for Base Editing in Yeasts

The expression vectors pGAL1-rAPOBEC1-nCas9-UGI (N-BE3), pGAL1-Split-AID10, and pGAL1-Split-BE3 for base editing were constructed with reference to the published article[15]. Amino acid sequences of Split-AID10-N and Split-AID10-C in the expression vector pGAL1-Split-AID10 were the same as described above. In the expression vector pGAL1-Split-BE3, an amino acid sequence of Split-BE3-N was shown in SEQ ID NO: 8 and an amino acid sequence of Split-BE3-C was shown in SEQ ID NO: 9. A yeast U6 promoter was directly obtained from the yeast genome through PCR amplification, and then intact gRNA expression cassettes were assembled through overlapping PCR reactions to construct a series of gRNA expression vectors pGAL1-yGFP-SNR35p-sgRNAs. The gRNA target information in yeasts is listed in Table 3.

TABLE 3

| gRNA target information in yeast cells | | |
|---|---|---|
| Target gene | Target sequence (5'-3') | |
| PolyC-1 | CCCCCCCCATGTTCCGAGATCGG | (SEQ ID NO: 151) |
| PolyC-2 | TCCCCCCCCTCAATTCCAGCAGG | (SEQ ID NO: 152) |
| PolyC-3 | ATCAGCCCCCCCCAAGGAAAGG | (SEQ ID NO: 153) |
| PolyC-4 | GAACAGCTGAACCCCCCCAATGG | (SEQ ID NO: 154) |
| PolyC-5 | CATTAAAGCAACCCCCCATAGGG | (SEQ ID NO: 155) |
| Can1-5 | TCCAATAACGGAATCCAACTGGG | (SEQ ID NO: 156) |
| Can1-9 | CACAAACACACCACAGACGTGGG | (SEQ ID NO: 157) |

3. Transformation and Expression in Yeast Cells

The transformation method of *Saccharomyces cerevisiae* referred to the published article[16]. The above-mentioned vectors each were transformed into the *Saccharomyces cerevisiae* strain BY4741 by the conventional lithium acetate LiOAC chemical transformation method, and the positive transformant was selected through an auxotrophy gene on the plasmid. Specifically, positive transformant clones carrying a target plasmid were picked from auxotroph plates, inoculated in the liquid defective medium, and cultivated in the 2% glucose carbon source-containing medium for 2 d until the 2% glucose carbon source-containing medium was saturated to obtain a first fungal solution, then the first fungal solution was inoculated in a 2% raffinose carbon source-containing medium at a dilution ratio of 1:1,000 and cultivated for 2 d until the 2% raffinose carbon source-containing medium was saturated to obtain a second fungal solution, the second fungal solution was inoculated in a 1% galactose carbon source-containing medium at a dilution ratio of 1:10,000 and cultivated for 2 d to 3 d until the 1% galactose carbon source-containing medium was saturated to obtain a third fungal solution, and an appropriate amount of the third fungal solution was collected for subsequent genome extraction.

4. Deep Sequencing of Target Sequences and Deep Sequencing of Whole Genomes for Yeast Cells (1) For the deep sequencing of target sequences, the genome extraction and target amplicon library construction were conducted with reference to the published article[17].

(2) For whole genome deep sequencing in yeast cells, an appropriate amount of the galactose-induced saturated fungal solution was taken and streaked on plates, and after clones grew, 10 to 20 monoclonal clones were picked and subjected to first-generation sequencing to determine whether the corresponding target site was edited. Clones in which the target site was edited were inoculated into 3 mL YPDA liquid medium and cultivated under shaking until the saturated fungal solution was obtained, then genomic DNA of yeast cells was extracted with a commercial kit (HiPure Yeast DNA Kit, #D3147, Guangzhou Magen Biotech Co., Ltd.), then the library construction was conducted with a commercial next-generation sequencing library-construction kit (VAHTS Universal DNA Library Prep Kit for Illumina, #ND607, Vazyme Biotech Co., Ltd.), and a constructed library was finally sent to the sequencing company for PE150 high-throughput sequencing, where a sequencing coverage depth for each clone was required to be more than 100× and about 1 G data were required for each genome.

5. Experimental Results

Figure 6A:
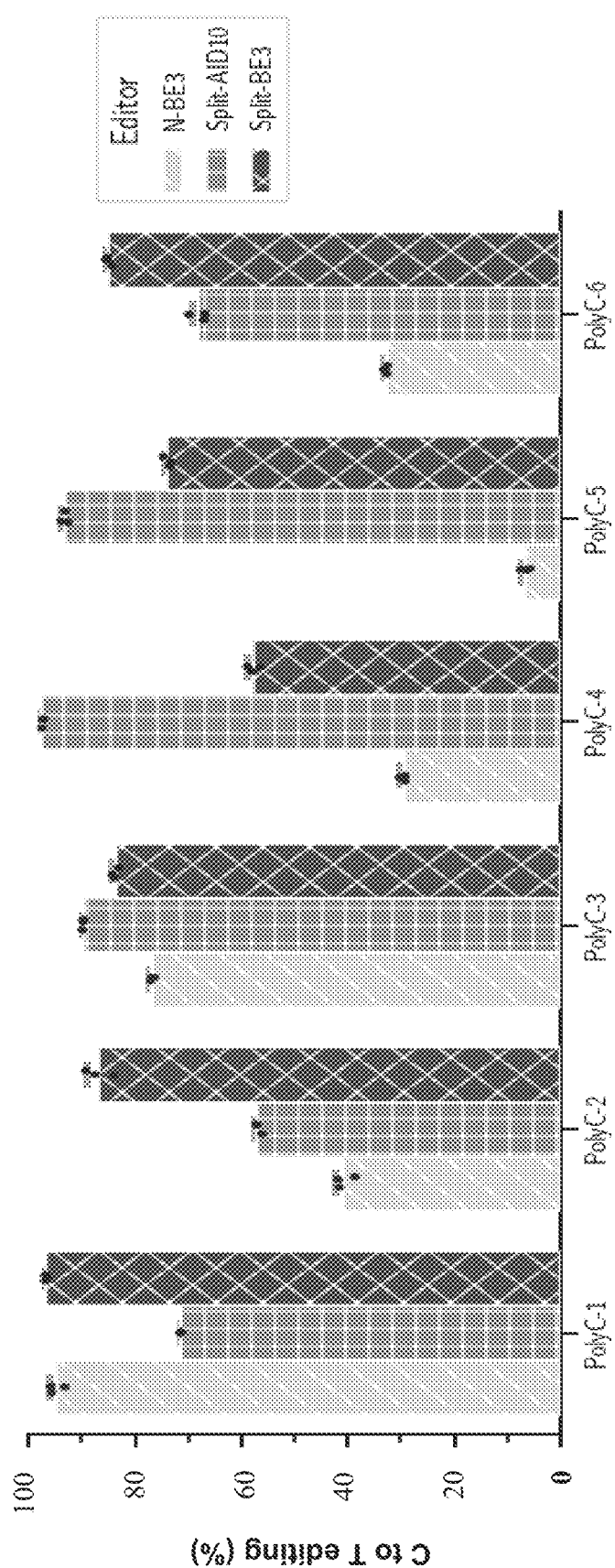
FIG. 6A is a statistical graph of editing efficiencies of six target sites in Saccharomyces cerevisiae (n=3)

As shown in FIG. 6A, analysis results of 6 endogenous target sites in the yeast genome showed that average editing efficiencies of N-BE3 were from 6.5% to 94.9%, and the effective editing window was from $C_3$ to $C_{10}$ in a target sequence; The average editing efficiencies of Split-AID10 were from 56.9% to 97.3%, and the effective editing window was from $C_5$ to $C_{15}$ in a target sequence; and average editing efficiencies of Split-BE3 were from 57.8% to 96.8%, and the effective editing window was $C_5$ to $C_{14}$ in a target sequence. In addition, compared with the commonly used N-BE3, editing windows of both Split-AID10 and Split-BE3 were shifted to the PAM-proximal region.

Figure 6B:
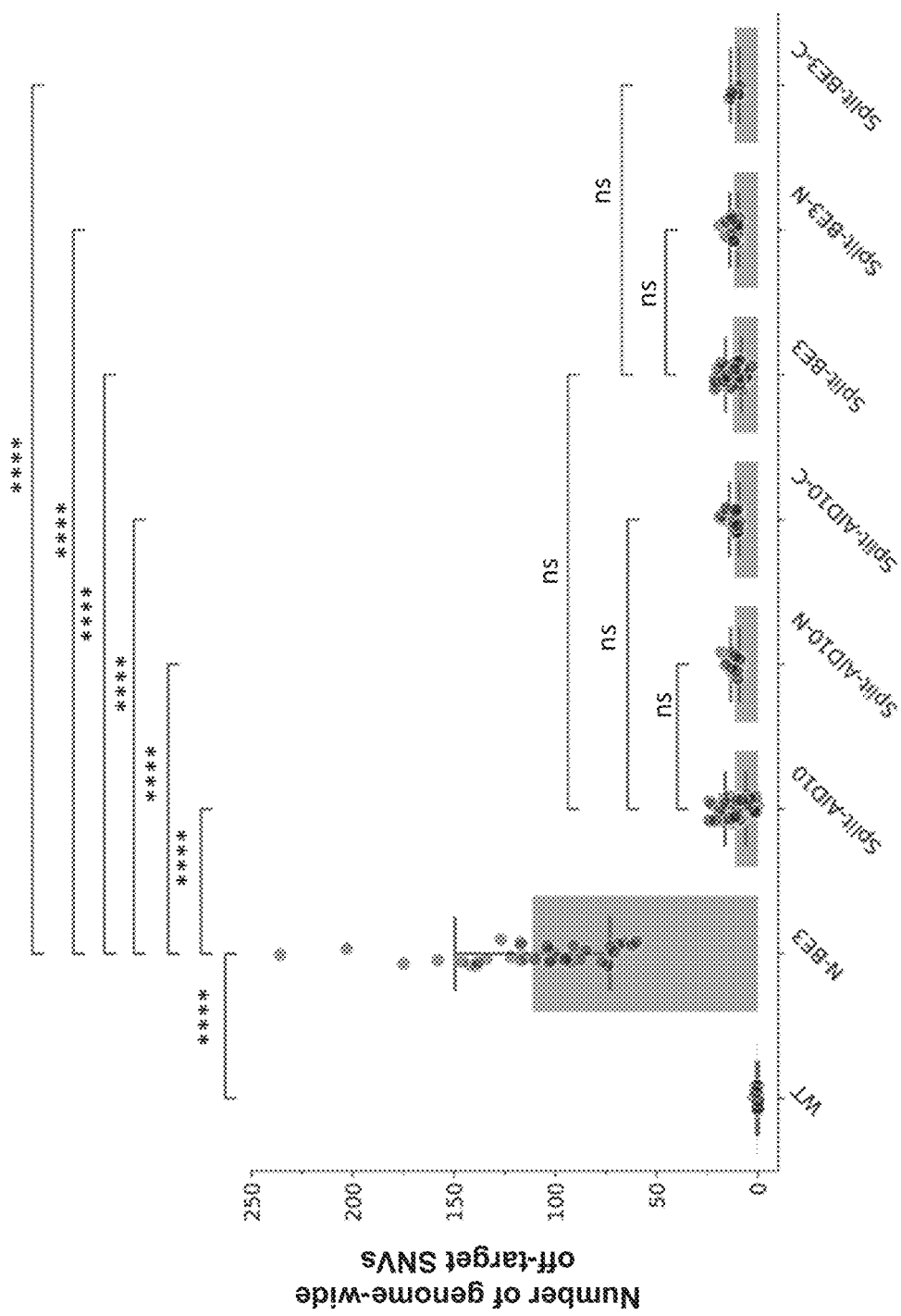
FIG. 6B shows the genome-wide evaluation of off-target edits at single-cell level in Saccharomyces cerevisiae, where each dot represents genome-wide off-target SNVs for one single-cell-derived yeast clone (ns: not significant; ****$p<0.0001$)
Figure 7A:
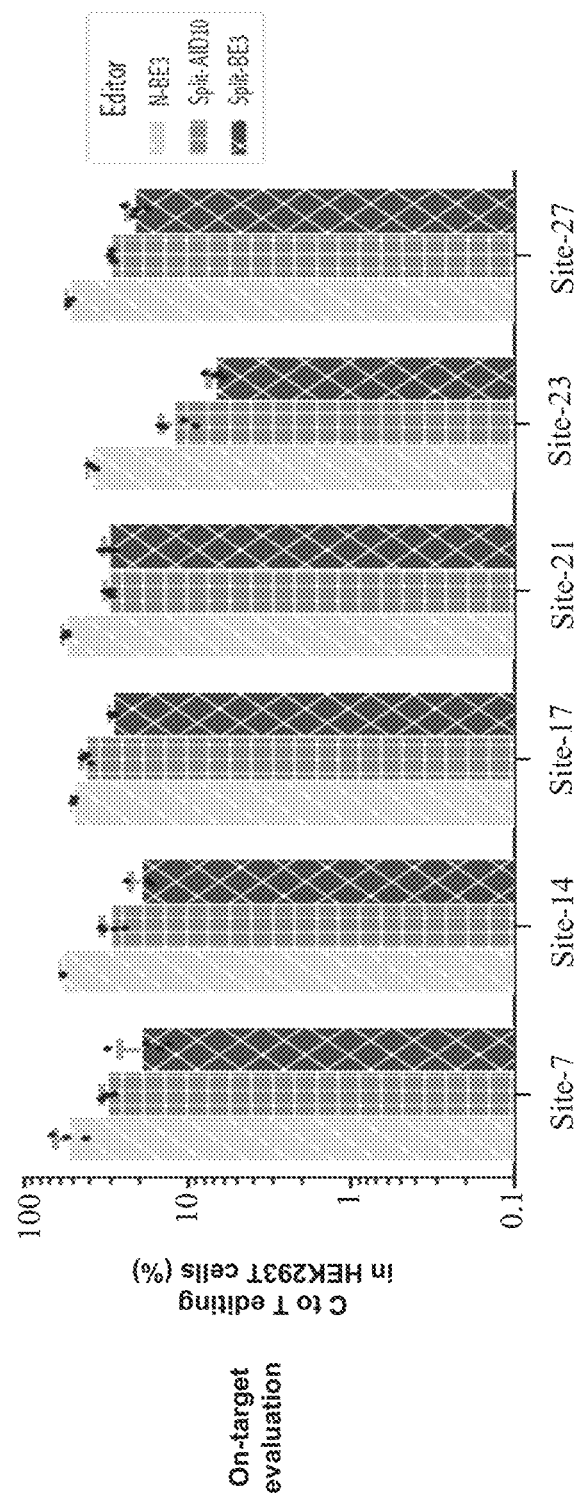
FIG. 7A is a statistical graph of on-target editing efficiencies of 6 target sites in HEK293T cells (n=3)
Figure 7B:
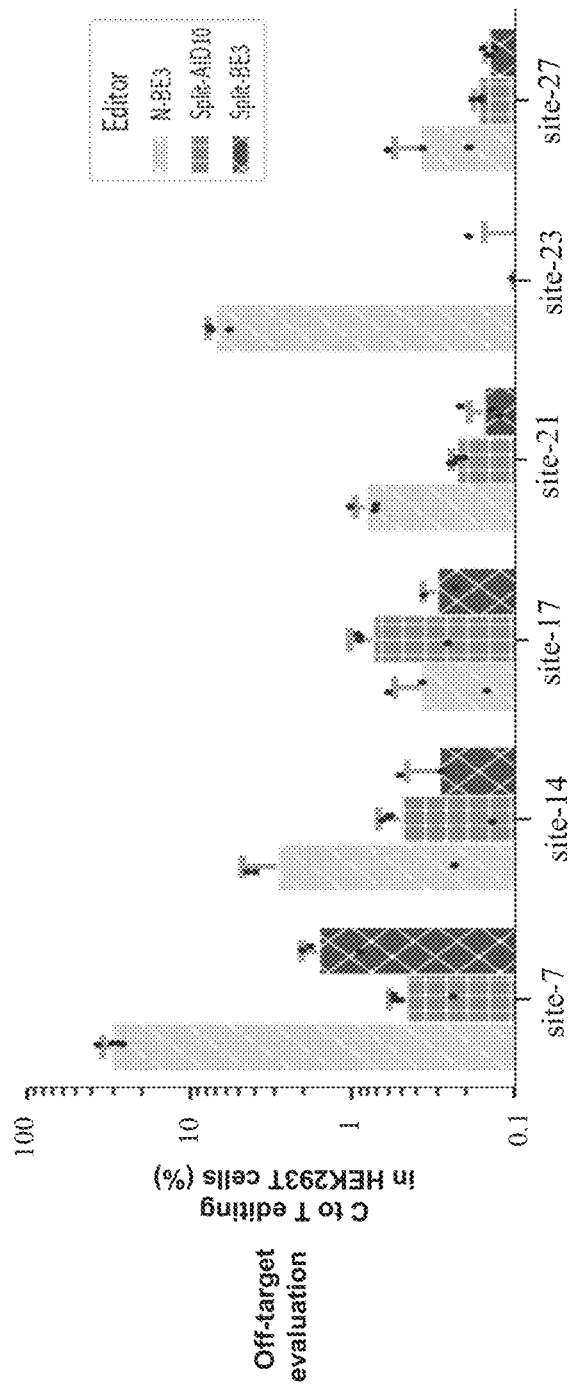
FIG. 7B is a statistical graph of off-target editing efficiencies of 6 target sites in HEK293T cells (n=3)
Figure 7C:
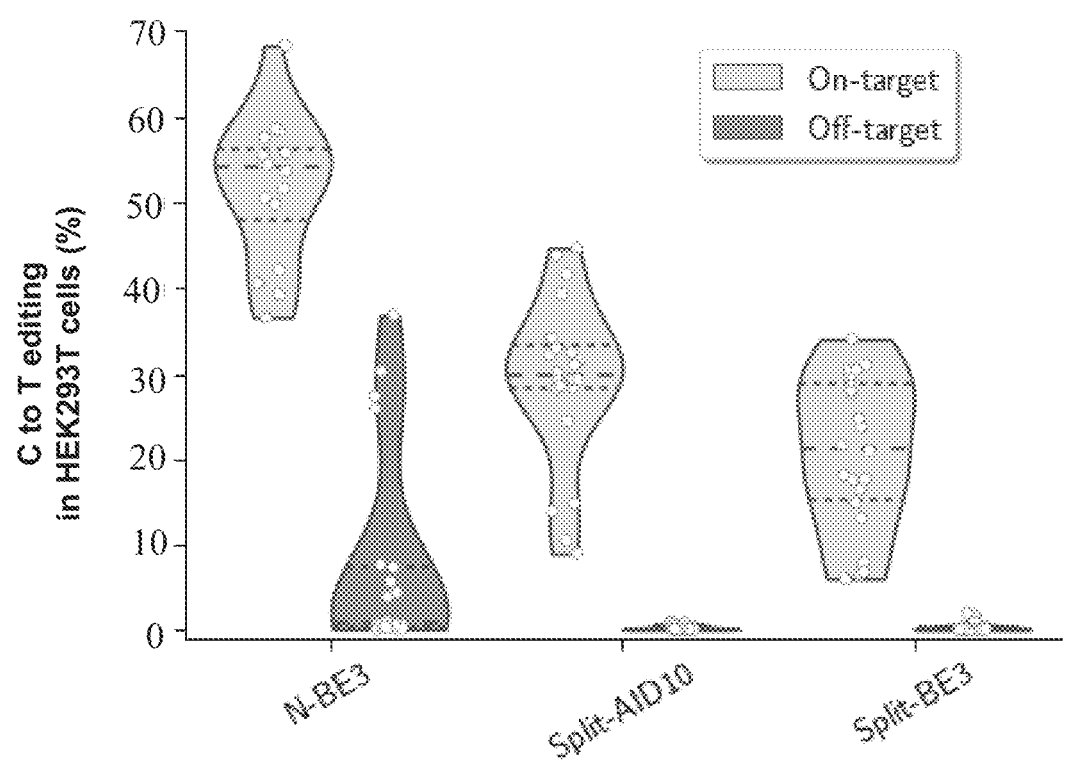
FIG. 7C is a statistical graph combining on-target editing efficiencies with off-target editing efficiencies for all target sites of FIG. 7A and FIG. 7B in HEK293T cells (n=18)
Figure 7D:
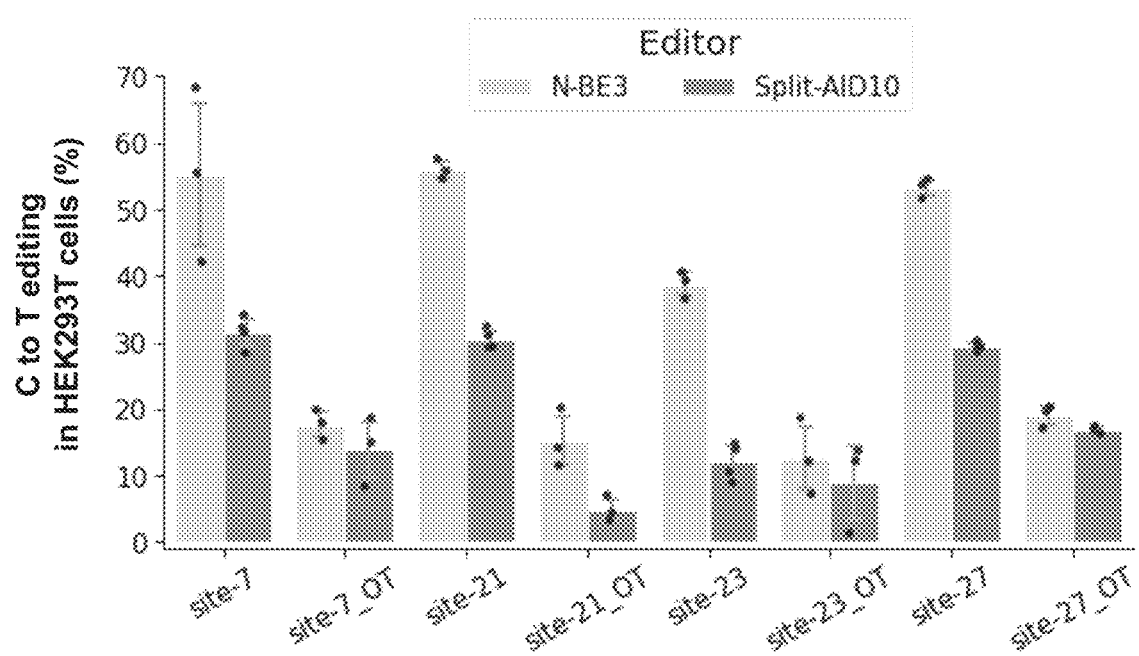
FIG. 7D is a statistical graph of editing efficiencies in 4 on-target sites and in Cas9-dependent off-target sites of the corresponding on-target site in HEK293T cells (n=3)
Figure 8A:
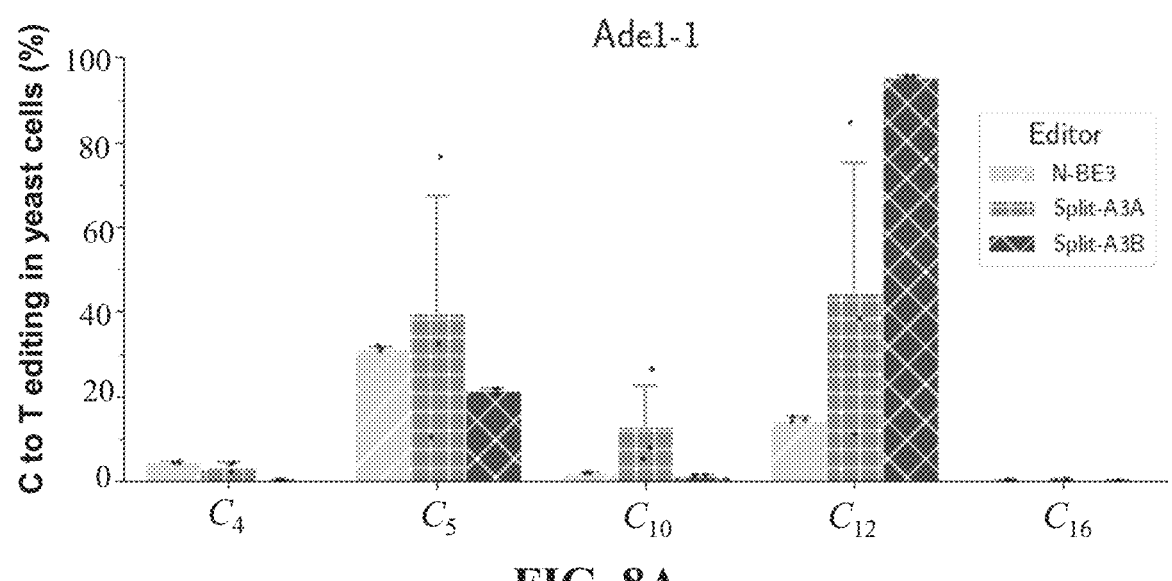
FIG. 8A is a statistical graph illustrating the editing efficiency for each C of an endogenous target site Ade1-1 in Saccharomyces cerevisiae (n=3)
Figure 8B:
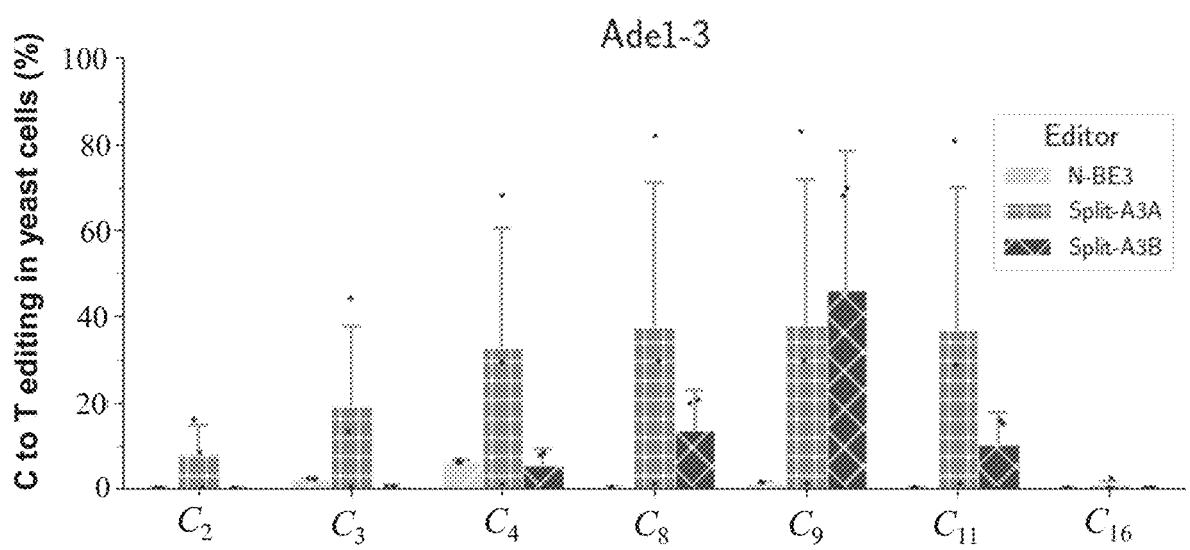
FIG. 8B is a statistical graph illustrating the editing efficiency for each C of an endogenous target site Ade1-3 in Saccharomyces cerevisiae (n=3)
Figure 8C:
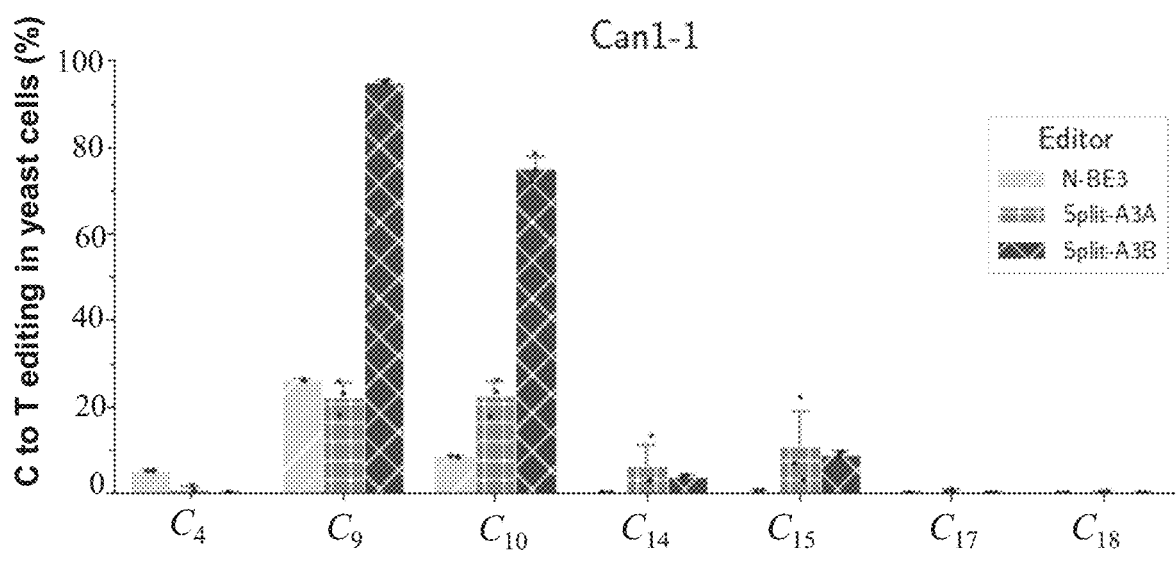
FIG. 8C is a statistical graph illustrating the editing efficiency for each C of an endogenous target site Can1-1 in Saccharomyces cerevisiae (n=3)
Figure 8D:
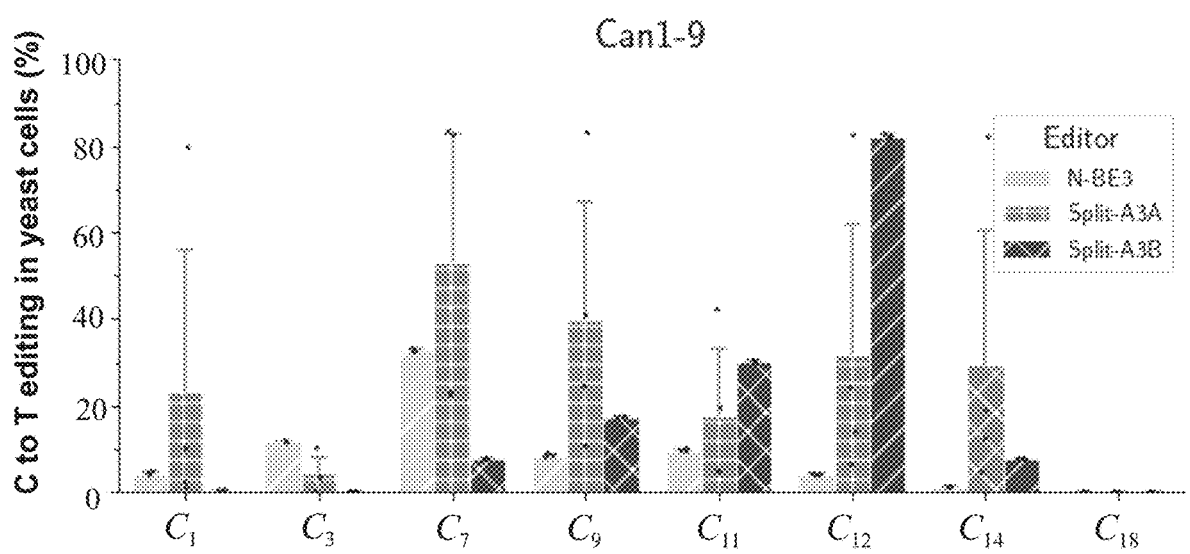
FIG. 8D is a statistical graph illustrating the editing efficiency for each C of an endogenous target site Can1-9 in Saccharomyces cerevisiae (n=3)

As shown in FIG. 6B, both Split-AID10 using the deaminase AID10 and Split-BE3 using the deaminase rAPOBEC1 could significantly reduce genome-wide off-target effects in yeast cells. Although the yeast genome had a very small size (only about 10 Mb), about 100 off-target edits could be detected at a genome-wide level on average in the N-BE3 group. However, Split-AID10 and Split-BE3 could greatly reduce off-target effects, and less than 10 off-target edits could be detected on average, which were comparable to levels of the control groups Split-AID10-N/Split-AID10-C and Split-BE3-N/Split-BE3-C and close to the background level.

This example proves that split complementary base editing systems have a high editing activity in yeast cells, can significantly reduce genome-wide off-target effects, and are very safe.

Example 4 Split complementary base editing systems Split-AID10 and Split-BE3 also exhibited robust on-target editing and extremely-low genome-wide random off-target effects in HEK293T cells.

1. Experimental Material

The human embryonic kidney cell line 293T (HEK293T) came from the American Type Culture Collection (ATCC).

2. Construction of Vectors for Base Editing in Human Cells

With reference to the published article[18], the core vector was constructed by integrating a CMV promoter and a human U6 promoter into the vector backbone pX330 (Addgene #42230), and then relevant expression vectors pCMV-rAPOBEC1-nCas9-UGI (N-BE3), pCMV-Split-AID10, and pCMV-Split-BE3 were constructed. Amino acid sequences Split-AID10-N and Split-AID10-C in the pCMV-Split-AID10 expression vector were the same as mentioned above, and amino acid sequences Split-BE3-N and Split-BE3-C in the pCMV-Split-BE3 expression vector were also the same as mentioned above. In this example, the gRNA expression vector was modified as follows: a red fluorescent protein mScarlet was inserted downstream of the CMV promoter to indicate the transfection efficiency, and an annealed gRNA oligo for the corresponding target site was inserted between U6 and gRNA Scaffold through BbsI digestion to complete the construction of a gRNA expression cassette. The gRNA target information in HEK293T cells is listed in Table 4 below.

TABLE 4 gRNA target sequence information in the human genome

| Cas9 type | Target gene | Target sequence (5'-3') |
|---|---|---|
| SpCas9 | Site-7 | CCCAGCTCCAGCCTCTGATGAGG (SEQ ID NO: 158) |
| | Site-14 | CCTCCGTATCACTCTCTGACTGG (SEQ ID NO: 159) |
| | Site-17 | GTCGTAGCCAGTCCGAACCCCGG (SEQ ID NO: 160) |
| | Site-21 | GTGGCACTGCGGCTGGAGGTGGG (SEQ ID NO: 161) |

TABLE 4-continued gRNA target sequence information in the human genome

| Cas9 type | Target gene | Target sequence (5'-3') |
|---|---|---|
| | Site-23 | GCCTCCCCAAAGCCTGGCCAGGG (SEQ ID NO: 162) |
| | Site-27 | GGGACTGATCCCTTAATGTGTGG (SEQ ID NO: 163) |
| SaCas9 | Site-7 | GCCCAGCTCCAGCCTCTGATGAGGGGT (SEQ ID NO: 164) |
| | Site-14 | GGCCTCCGTATCACTCTCTGACTGGGGT (SEQ ID NO: 165) |
| | Site-17 | GGTCGTAGCCAGTCCGAACCCCGGAGT (SEQ ID NO: 166) |
| | Site-21 | GTGGCACTGCGGCTGGAGGTGGGGGT (SEQ ID NO: 167) |
| | Site-23 | GGCCTCCCCAAAGCCTGGCCAGGGAGT (SEQ ID NO: 168) |
| | Site-27 | GTGGGACTGATCCCTTAATGTGTGGGGT (SEQ ID NO: 169) |

3. Cell Cultivation and Transfection

The HEK293T cells grew adherently. HEK293T cells were inoculated in a DMEM high-glucose medium with 10% fetal bovine serum and cultivated in an incubator at 37° C. and 5% $CO_2$. The day before BE plasmid transfection, an appropriate number of cells were added to the 48-well plate, and cells were transfected by the conventional liposome in the next day. After 48 h to 72 h of expression, the cells were collected and subjected to genome extraction.

4. Deep Sequencing and Analysis of Mutations at Target Sites in HEK293T Cells

In order to well evaluate the performance of split complementary base editing systems, in this example, 6 matching target sites were designed, and on-target and off-target effects of BEs were detected at the same time. A specific implementation was as follows: SaCas9 was used to search for appropriate target sites in the human genome, then overlapping target sequences meeting the requirements of SpCas9 PAM were selected, and the targeted editing efficiency evaluation and orthogonal R-Loop assay were conducted for the same site. In the orthogonal R-Loop assay, pX601 (Addgene #61591) was adopted as the expression vector. In order to improve the detection efficiency, the expression vector pX601 was appropriately modified, including usage of the SaCas9 nickase (nSaCas9) and the addition of a UGI functional domain. Target site information for the orthogonal R-loop assay is detailed in Table 4.

A two-step strategy was adopted for deep sequencing and library construction: (1) Target-specific primers were first designed for capture, and partial sequences of the Illumina Nextera adapter were added to the terminus of each primer. (2) Then, with PCR products obtained in the step 1 as templates, a complete library was amplified, including sample barcodes of 8 bases and the complete P5/P7 sequence. Finally, products of the two rounds of PCR products were subjected to a series of routine operations such as purification, concentration determination, and library homogenization, and sent to Genewiz Inc., sz for high-throughput sequencing.

The analysis of amplicon deep sequencing results mainly included the following two parts: library demutiplexing and editing efficiency calculation. The library demultiplexing was conducted with the official bcl2fastq software of Illumina. The original BCL data was demultiplexed into independent FASTQ-format files one by one according to a barcode table of pooled samples, including Read 1 and Read 2, then the CRISPResso2[11] analysis was conducted separately for each target to obtain a matrix of base substitutions near a target site, and finally the editing efficiency was calculated.

5. Cas9-Dependent Off-Target Edits Detection

In this example, the Cas9 protein-dependent off-target edits detection was also conducted for 4 on-target sites, and mismatches <6 in the protospacer were conducted with the prediction software Cas-OFFinder for each target sequence to find Cas9 protein-dependent off-target sites in the human genome. The predicted candidates were filtered by the PAM-proximal seed region and harbouring cytosines within the activity window. Particularly, the loci that have a 5-nucleotide fully-matched seed region for Cas9 binding were prioritized. The empirical Cas9 preferred targeting context was applied to further narrow down the sites for testing. Finally, specific capture primers were designed for subsequent amplicon library construction and sequencing.

6. Experimental Results

Experimental results are shown in FIG. 7A to FIG. 7D. It can be seen from FIG. 7A that Split-BE3 based on the cytidine deaminase rAPOBEC1 and Split-AID10 based on the cytidine deaminase AID10 can successfully allow base substitutions from C to T in target sequences in HEK293T cells, where the editing efficiency is about 50% comparable to that of N-BE3. It can be seen from FIG. 7B to FIG. 7D that Split-AID10 and Split-BE3 can not only reduce Cas9-dependent off-target effects, but also significantly reduce the Cas9-independent off-target edits. This example proves that the split complementary base editing systems have a high editing activity in HEK293T cells, can reduce the Cas9-dependent off-target edits and significantly reduce genome-wide off-target effects, exhibit excellent safety, and have a promising practical application prospect.

Example 5 Split-A3A and Split-A3B exhibited prominent base editing efficiencies in the eukaryotic organism.

1. Construction of Expression Vectors for Base Editing in Yeasts

With reference to the method in Example 3, expression vectors of Split-A3A are pGAL1-Split-A3A-N and pGAL1-Split-A3A-C, where the amino acid sequence of Split-A3A-N is shown in SEQ ID NO: 10 and the amino acid sequence of Split-A3A-C is shown in SEQ ID NO: 11; and expression vectors of Split-A3B are pGAL1-Split-A3B-N and pGAL1-Split-A3B-C, where the amino acid sequence of Split-A3B-N is shown in SEQ ID NO: 12 and the amino acid sequence of Split-A3B-C is shown in SEQ ID NO: 13.

2. Experimental Results

As shown in FIG. 8A to FIG. 8D, the Split-A3A based on the cytidine deaminase $A_3A$ and the Split-A3B based on the cytidine deaminase $A_3B$ successfully allow base substitutions from C to T in a target sequence in yeast cells. The editing window of Split-A3A is $C_1$ to $C_{15}$, and the editing efficiencies for C bases at different sites in the editing window are from 22.1% to 84.7%. The editing window of Split-A3B is $C_5$ to $C_{15}$, and editing efficiencies at different sites in the editing window are from 9.5% to 95.5%.

Example 6 The split complementary adenine base editing systems Split-ABE8e and Split-ABE8e-N7-C2 could allow efficient adenine base editing in plants.

1. Experimental Materials

In this example, the rice material was the same as in Example 1 and the *Arabidopsis* material was the same as in Example 2.

2. Construction of Transient Expression Vectors in *Arabidopsis* Protoplasts

Transient expression vectors for commonly used ABE7.10 and ABE8e in *Arabidopsis* were pHBT-ABE7.10 and pHBT-ABE8e, where the promoter was AtUBQ10 promoter and the terminator was NOS terminator. The above vectors all were constructed in our laboratory and had been disclosed through a published article[14]. Expression vectors of Split-ABE8e and Split-ABE8e-N7-C2 were constructed with reference to the construction methods of Split-AID10 and Split-AID10-N5-C4 in Example 1. The pHBT-Split-ABE8e-N and pHBT-Split-ABE8e-C vectors of Split-ABE8e and the pHBT-Split-ABE8e-N7 and pHBT-Split-ABE8e-C2 vectors of Split-ABE8e-N7-C2 were obtained on the basis of the pHBT-PIGS-ABE8e vector. The amino acid sequence of Split-ABE8e-N is shown in SEQ NO: 29, the amino acid sequence of Split-ABE8e-C is shown in SEQ NO: 30, the amino acid sequence of Split-ABE8e-N7 is shown in SEQ NO: 31, and the amino acid sequence of Split-ABE8e-C2 is shown in SEQ NO: 32. The transient expression vector for gRNAs in *Arabidopsis thaliana* was a pUC119-AtU6-26pro-AtFLS2-sgRNA expression vector constructed based on the pUC119-AtU6-26pro-sgRNA vector described in Li, Z. et al. 2019. Current protocols in molecular biology, https://doi.org/10.1002/cpmb.89 (target sequences are shown in Table 1).

3. Deep Sequencing and Base Substitution Analysis of Target Sequences in *Arabidopsis* Protoplasts The outcomes of deep sequencing and base substitution analysis were the same as those of Example 1.

4. Construction of Binary Vectors for Plant Transformation

With reference to the construction method of the binary vector of Spit-AID10 for rice in Example 1, the binary vector pH-Split-ABE8e-N-C of Split-ABE8e suitable for rice in this example was constructed, and on this basis, a commercially-synthesized nucleic acid fragment of a gRNA expression cassette AtU6-26pro-AtALS/AtPDS3/AtBAK1-sgRNA was fused to the pH-Split-ABE8e-N-C vector through simple restriction digestion and ligation to obtain the binary vector targeting AtALS or AtPDS3 or AtBAK1 for rice in this example (gRNA target sequence information is listed in Table 1).

With reference to the construction method of the binary vector of Spit-AID10 for *Arabidopsis* in Example 2, the binary vector pH-EC-Split-ABE8e-N-C of Split-ABE8e suitable for *Arabidopsis* in this example was constructed, and on this basis, a commercially-synthesized nucleic acid fragment of a gRNA expression cassette AtU6-26pro-OsACC/OsNRT1.1B/OsDEP1-sgRNA was fused to the pH-EC-Split-ABE8e-N-C vector through simple restriction digestion and ligation to obtain the binary vector targeting OsACC or OsNRT1.1B or OsDEP1 for *Arabidopsis* in this example (gRNA target sequence information is listed in Table 1).

5. Transformation of Plants

The method for genetic transformation of rice was the same as in Example 1, and the method for genetic transformation of *Arabidopsis* was the same as in Example 2.

6. Experimental Results

Figure 9A:
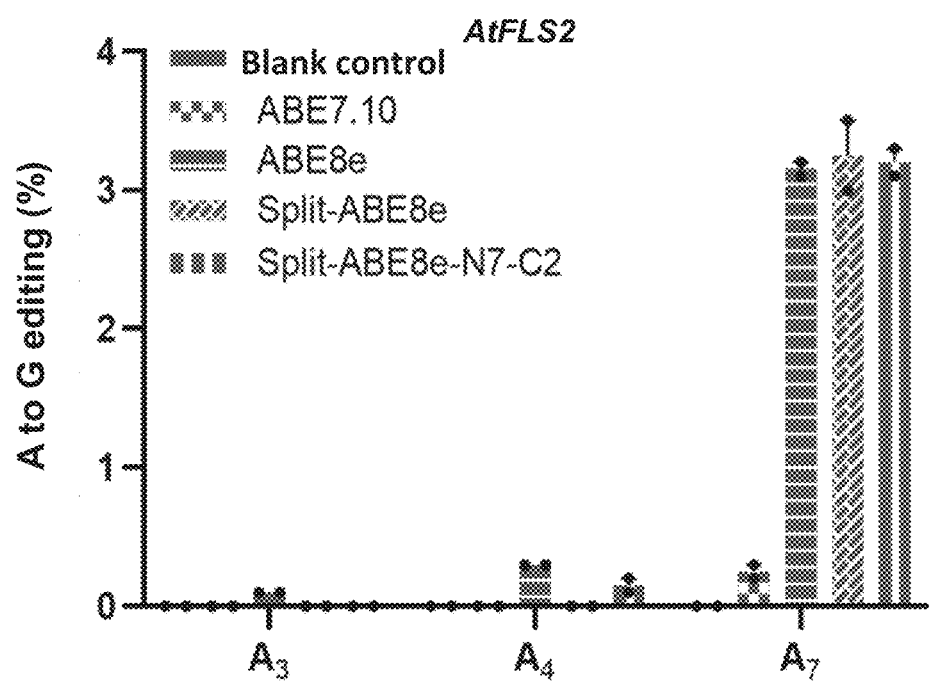
FIG. 9A is a statistical graph of editing efficiencies in the AtFLS2 site by using Split-ABE8e, Split-ABE8e-N7-C2 systems or two traditional adenine base editing systems in Arabidopsis protoplasts (n=2)

In order to quickly test split complementary adenine base editing systems Split-ABE8e and Split-ABE8e-N7-C2, the Split-ABE8e-N expression vector and the Split-ABE8e-C expression vector, two necessary components for expressing Split-ABE8e, were co-transfected with a gRNA expression vector targeting an AtFLS2 site into *Arabidopsis* protoplasts, and the Split-ABE8e-N7 expression vector and the Split-ABE8e-C2 expression vector, two necessary components for expressing Split-ABE8e-N7-C2, were co-transfected with the above gRNA expression vector into another group of protoplasts. Control groups of the traditional ABE7.10 and ABE8e were also set. 48 h later, genomic DNA was extracted from protoplasts and subjected to deep sequencing for the target site AtFLS2. As shown in FIG. 9A, the two novel adenine base editing systems Split-ABE8e and Split-ABE8e-N7-C2 both allowed effective base editing at the AtFLS2 site, where average editing efficiencies for the base A at position 7 of the target were 3.3% and 3.2%, respectively, which were similar to the 3.2% of the traditional ABE8e and both were higher than the 0.3% of the traditional ABE7.10.

In order to further confirm the effectiveness of the novel split complementary adenine base editing system, base editing efficiencies of split-ABE8e were evaluated in transgenic *Arabidopsis* and rice plants. As shown in FIG. 9B, the editing efficiencies at AtALS, AtPDS3, and AtBAK1 ranged from 3.1% to 35.2% (16.6% on average) by Split-ABE8e in transgenic *Arabidopsis*. As shown in FIG. 9C, in transgenic rice plants, the editing efficiencies at OsACC, OsDEP1, and OsNRT1.1B by Split-ABE8e ranged from 55.1% to 53.8% (54.7% on average).

The data provided in this example proves that split complementary adenine base editing systems Split-ABE8e and Split-ABE8e-N7-C2 can allow efficient adenine base editing in plants. In particular, Split-ABE8e can allow efficient adenine base editing in transgenic plants of both rice as a representative monocotyledon and *Arabidopsis* as a representative dicotyledon, revealing the extensive adaptability of split complementary adenine base editing systems in plants.

Example 7 Split-ABE8e could allow efficient adenine base editing in yeast cells and HEK293T cells.

1. Experimental Materials

The experimental material and method for the present example in yeasts were as shown in Example 3, and the experimental material and method for the present example in HEK293T cells were as shown in Example 4.

2. Expression vectors of Split-ABE8e in yeasts were pGAL1-Split-ABE8e-N and pGAL1-Split-ABE8e-C, and the control vectors were pGAL1-nSpCas9, pGAL1-N-ABE7.10, and pGAL1-N-ABE8e. Expression vectors of Split-ABE8e in HEK293T cells were pCMV-Split-ABE8e-N and pCMV-Split-ABE8e-C. Amino acid sequences of Split-ABE8e-N and Split-ABE8e-C included in the above yeast and human Split-ABE8e expression vectors were as described above. The gRNA expression vectors in yeasts and human cells were as described in Examples 3 and 4. The gRNA target sequence information is listed in Tables 3 and 4.

3. Experimental Results

Figure 10A:
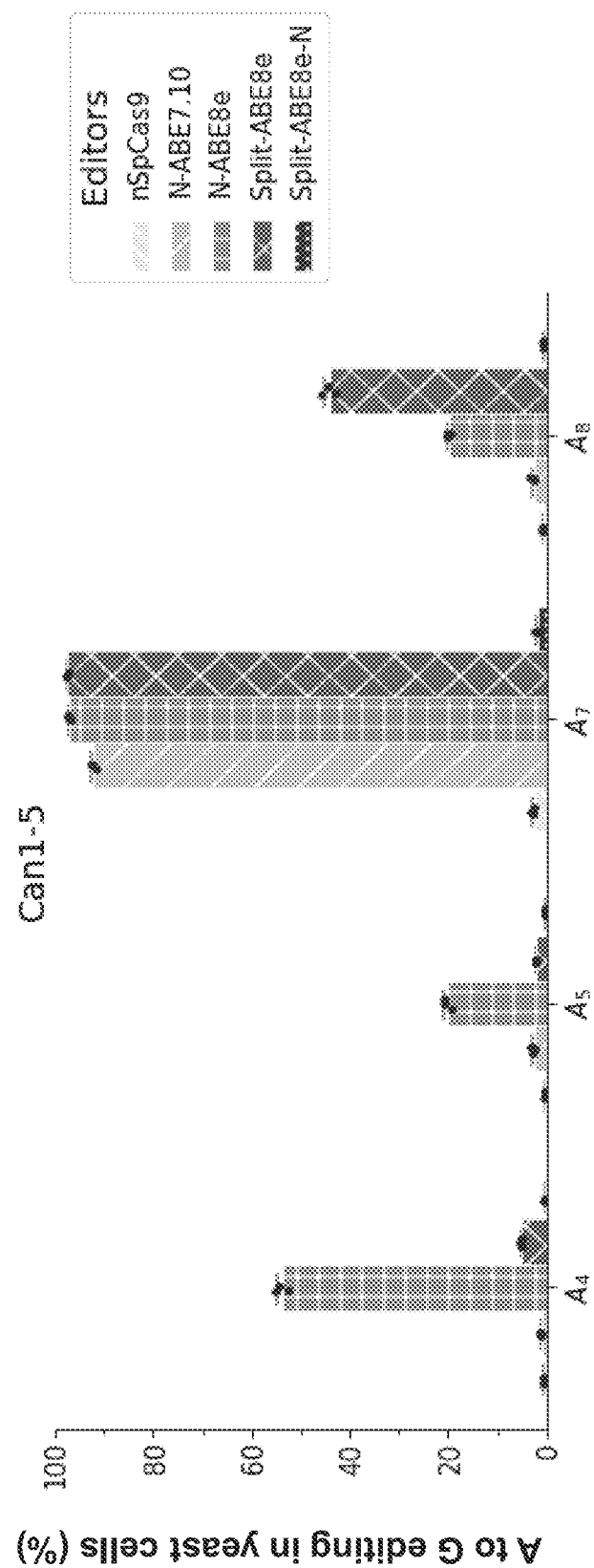
FIG. 10A and FIG. 10B are statistical graphs of editing efficiencies for each base A at Saccharomyces cerevisiae endogenous target sites Can1-5 and Can1-9, respectively (n=3)
Figure 10B:
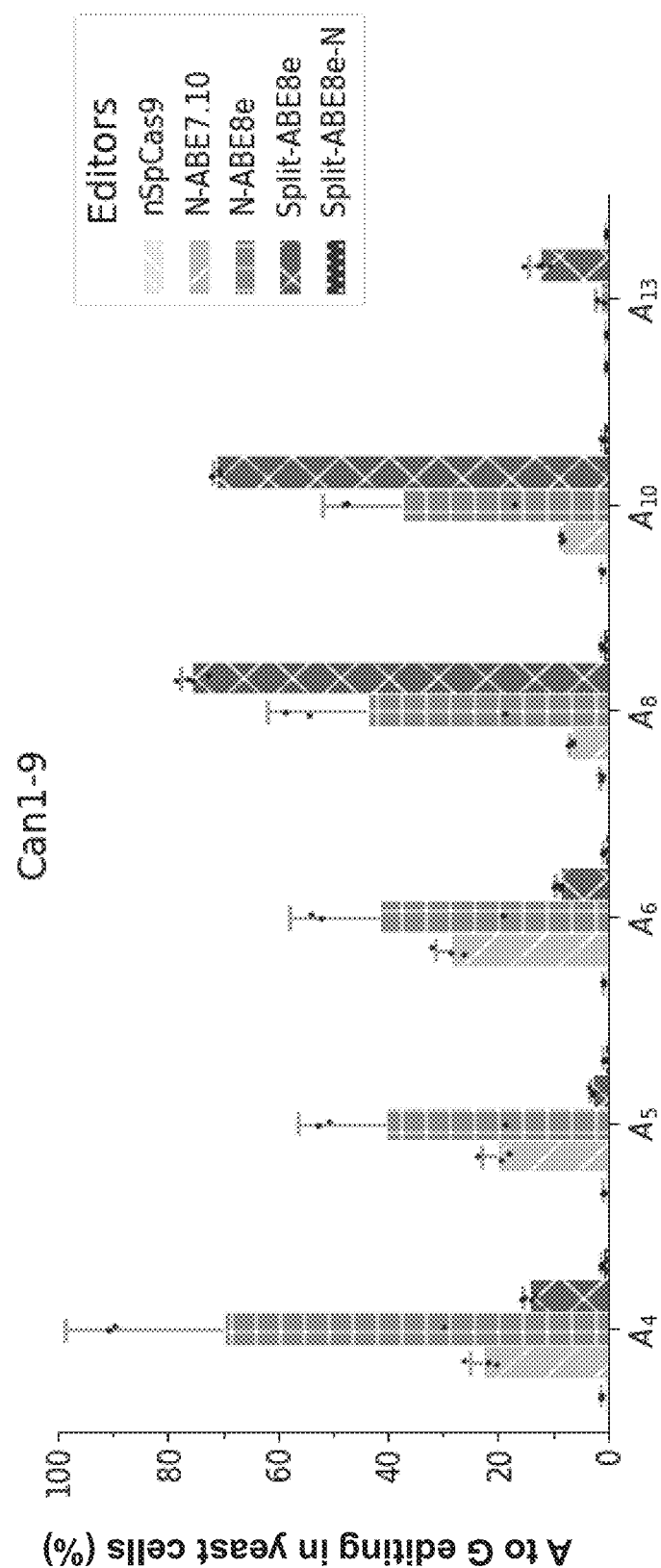
Figure 10C:
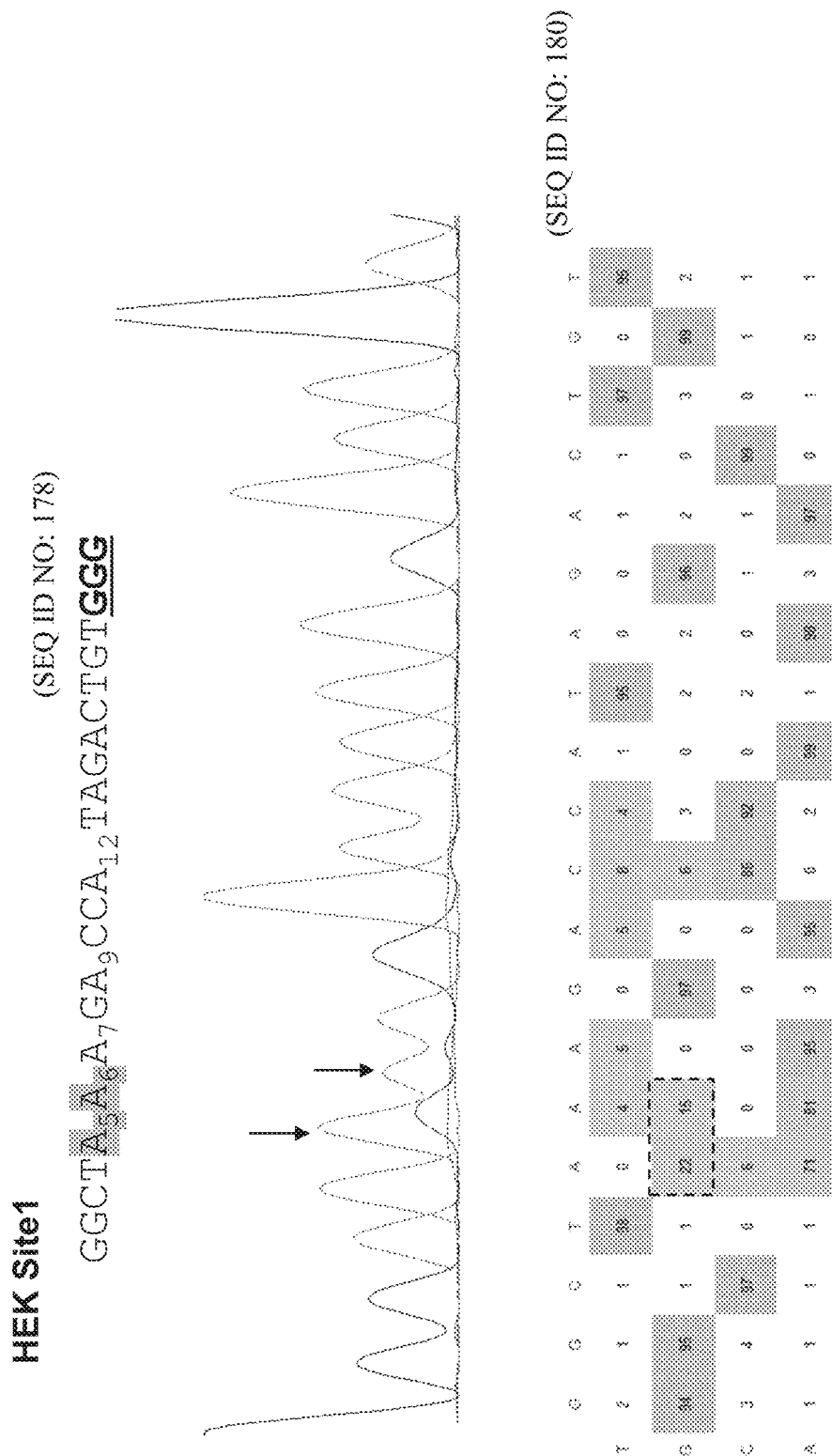
FIG. 10C and FIG. 10D show adenine base editing conditions for targets site 1 and site 2 in a human embryonic kidney cell line HEK293T, respectively.
Figure 10D:
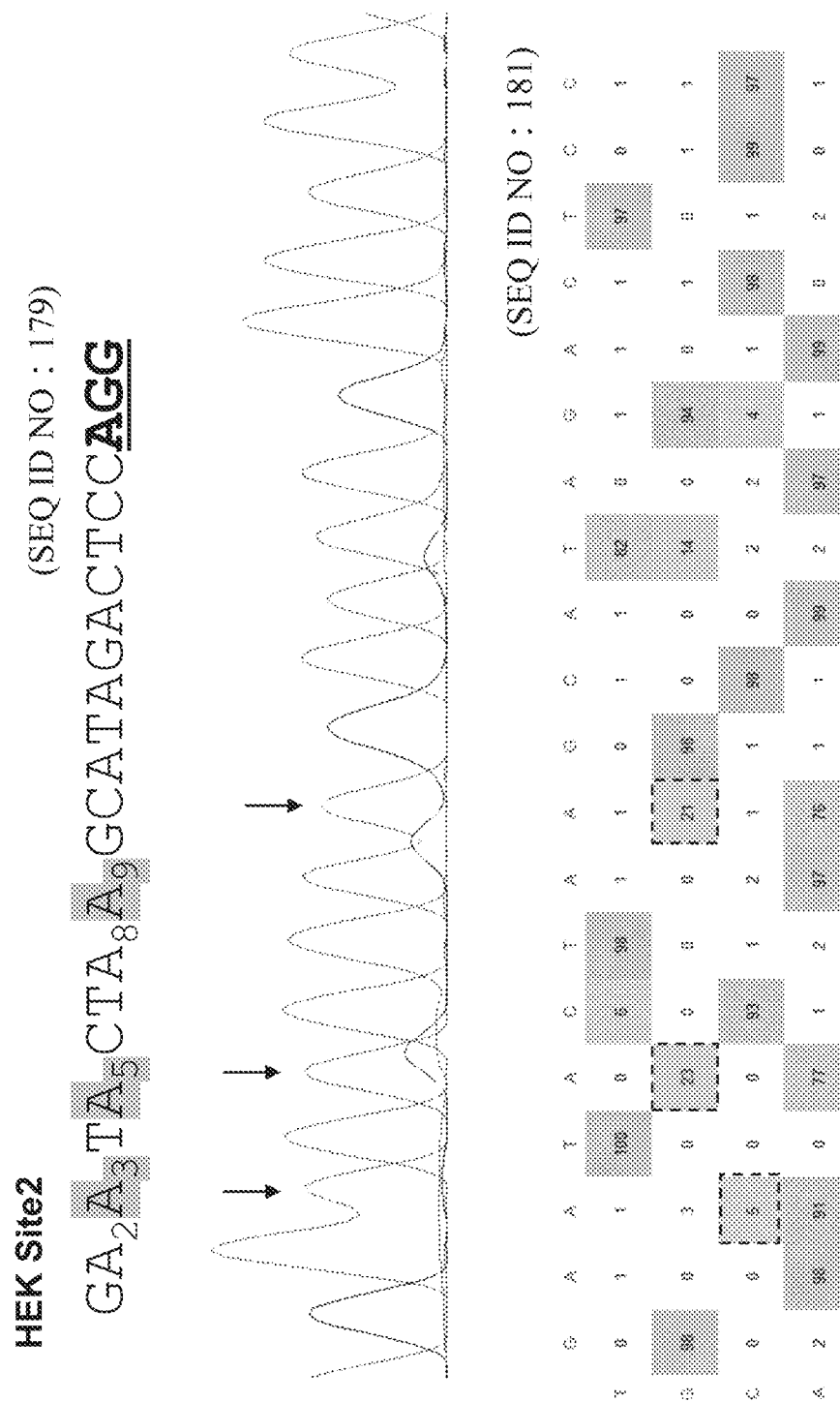

Split-ABE8e was co-transformed into yeast cells with a gRNA targeting the yeast endogenous site Can1-8, and deep sequencing was conducted. As shown in FIG. 10A, Split-ABE8e successfully allowed adenine base editing at the Can1-8 site in yeast cells, where the editing window was from $A_4$ to $A_{13}$ and A to G base editing efficiencies were from 25% to 82%. FIG. 10B shows the editing details at the endogenous site Can1-9 in yeast cells by Split-ABE8e. Then, Split-ABE8e was co-transfected into HEK293T cells with a gRNA targeting the endogenous HEK Site 1, and after 3 d of expression, and the genome DNA was extracted. The HEK Site 1 was subjected to simple PCR reactions with primers F and R, and the PCR products were subjected to Sanger sequencing. As shown in FIG. 10C, Split-ABE8e successfully allowed adenine base editing in HEK293T cells at the endogenous target site HEK Site 1 with the $A_5>G_5$ substitution. FIG. 10D shows the successful adenine base editing at the endogenous site HEK Site 2 in HEK293T cells by Split-ABE8e.

Experimental results demonstrated in this example indicate that Split-ABE8e can allow efficient A-to-G base substitutions for the endogenous target sites in representative unicellular organisms such as yeasts and mammalian cells such as human embryonic kidney 293T cells, which further confirms the extensive adaptability of split complementary base editing systems.

Finally, it should be noted that the above examples are only intended to illustrate the technical solutions of the present application, rather than to limit the protection scope of the present application. Although the present application is described in detail with reference to preferred examples, those of ordinary skill in the art should understand that various modifications or equivalent substitutions may be made to the technical solutions of the present application without departing from the essence and scope of the technical solutions of the present application.

REFERENCES

[1] WU J, ZENG Q, WANG Q, et al. SNP-based pool genotyping and haplotype analysis accelerate fine-mapping of the wheat genomic region containing stripe rust resistance gene Yr26 [J]. *Theor Appl Genet*, 2018, 131 (7): 1481-1496.

[2] LANDRUM M J, LEE J M, BENSON M, et al. ClinVar: public archive of interpretations of clinically relevant variants [J]. *Nucleic Acids Res*, 2016, 44 (D1): D862-868.

[3] ANZALONE A V, KOBLAN L W, LIU D R. Genome editing with CRISPR-Cas nucleases, base editors, transposases and prime editors [J]. *Nat Biotechnol*, 2020, 38 (7): 824-844.

[4] KOMOR A C, KIM Y B, PACKER M S, et al. Programmable editing of a target base in genomic DNA without double-stranded DNA cleavage [J]. *Nature*, 2016, 533 (7603): 420-424.

[5] JIN S, ZONG Y, GAO Q, et al. Cytosine, but not adenine, base editors induce genome-wide off-target mutations in rice [J]. *Science*, 2019, 364 (6437): 292-295.

[6] ZUO E, SUN Y, WEI W, et al. Cytosine base editor generates substantial off-target single-nucleotide variants in mouse embryos [J]. *Science*, 2019, 364 (6437): 289-292.

[7] STEINERT J, SCHIML S, FAUSER F, et al. Highly efficient heritable plant genome engineering using Cas9 orthologues from *Streptococcus thermophilus* and *Staphylococcus aureus* [J]. *Plant J*, 2015, 84 (6): 1295-1305.

[8] LI J F, NORVILLE J E, AACH J, et al. Multiplex and homologous recombination-mediated genome editing in *Arabidopsis* and *Nicotiana benthamiana* using guide RNA and Cas9 [J]. *Nat Biotechnol*, 2013, 31 (8): 688-691.

[9] LI Z, WANG F, LI J F. Targeted Transcriptional Activation in Plants Using a Potent Dead Cas9-Derived Synthetic Gene Activator [J]. *Curr Protoc Mol Biol*, 2019, 127 (1): e89.

[10] AFGAN E, BAKER D, BATUT B, et al. The Galaxy platform for accessible, reproducible and collaborative biomedical analyses: 2018 update [J]. *Nucleic Acids Res,* 2018, 46 (W1): W537-W544.
[11] CLEMENT K, REES H, CANVER M C, et al. CRISPResso2 provides accurate and rapid genome editing sequence analysis [J]. *Nat Biotechnol,* 2019, 37 (3): 224-226.
[12] HWANG G H, PARK J, LIM K, et al. Web-based design and analysis tools for CRISPR base editing [J]. *BMC Bioinformatics,* 2018, 19 (1): 542.
[13] JIN S, FEI H, ZHU Z, et al. Rationally designed APOBEC3B cytosine base editors with improved specificity [J]. *Mol Cell,* 2020, 79 (5): 728-740 e6.
[14] XIONG X, LI Z, LIANG J, et al. A cytosine base editor toolkit with varying activity windows and target scopes for versatile gene manipulation in plants [J]. *Nucleic Acids Res,* 2022, 50 (6): 3565-3580.
[15] LIU K, DENG S, YE C, et al. Mapping single-cell-resolution cell phylogeny reveals cell population dynamics during organ development [J]. *Nat Methods,* 2021, 18 (12): 1506-1514.
[16] CHEN P, WANG D, CHEN H, et al. The nonessentiality of essential genes in yeast provides therapeutic insights into a human disease [J]. *Genome Res,* 2016, 26 (10): 1355-1362.
[17] TAN J, ZHANG F, KARCHER D, et al. Engineering of high-precision base editors for site-specific single nucleotide replacement [J]. *Nat Commun,* 2019, 10 (1): 439.
[18] CONG L, RAN F A, COX D, et al. Multiplex genome engineering using CRISPR/Cas systems [J]. *Science,* 2013, 339 (6121): 819-823.

The invention claimed is:

1. A complementary base editing system based on bimolecular deaminases, comprising any one selected from the group consisting of the following (1) to (5):
   (1) a base editing fusion protein A, a base editing fusion protein B, and a guide RNA (gRNA);
   (2) an expression construct comprising nucleotide sequences encoding the base editing fusion protein A and the base editing fusion protein B, and the gRNA;
   (3) the base editing fusion protein A, the base editing fusion protein B, and an expression construct comprising the nucleotide sequence encoding the gRNA;
   (4) the expression construct comprising the nucleotide sequences encoding the base editing fusion protein A and the base editing fusion protein B, and the expression construct comprising the nucleotide sequence encoding the gRNA; and
   (5) an expression construct comprising the nucleotide sequences encoding the base editing fusion protein A and the base editing fusion protein B and the nucleotide sequence encoding the gRNA,
   wherein the base editing fusion protein A comprises a first nCas9 polypeptide fragment, a flexible peptide linker, and a first nucleobase deaminase polypeptide fragment sequentially from N-terminus to C-terminus; the base editing fusion protein B comprises a second nucleobase deaminase polypeptide fragment, the flexible peptide linker, and a second nCas9 polypeptide fragment sequentially from N-terminus to C-terminus; the first nucleobase deaminase polypeptide fragment and the second nucleobase deaminase polypeptide fragment are derived from the same nucleobase deaminase; and
   a combination of the base editing fusion protein A and the base editing fusion protein B in the base editing system is any one selected from the group consisting of the following (a) to (g):
   (a) the base editing fusion protein A having an amino acid sequence shown in SEQ ID NO: 15 (Split-AID10-N), and the base editing fusion protein B having an amino acid sequence shown in SEQ ID NO: 16 (Split-AID10-C);
   (b) the base editing fusion protein A having an amino acid sequence shown in SEQ ID NO: 17 (Split-AID10-N5), and the base editing fusion protein B having an amino acid sequence shown in SEQ ID NO: 18 (Split-AID10-C4);
   (c) the base editing fusion protein A having an amino acid sequence shown in SEQ ID NO: 19 (Split-BE3-N), and the base editing fusion protein B having an amino acid sequence shown in SEQ ID NO: 20 (Split-BE3-C);
   (d) the base editing fusion protein A having an amino acid sequence shown in SEQ ID NO: 21 (Split-A3A-N), and the base editing fusion protein B having an amino acid sequence shown in SEQ ID NO: 22 (Split-A3A-C);
   (e) the base editing fusion protein A having an amino acid sequence shown in SEQ ID NO: 23 (Split-A3B-N), and the base editing fusion protein B having an amino acid sequence shown in SEQ ID NO: 24 (Split-A3B-C);
   (f) the base editing fusion protein A having an amino acid sequence shown in SEQ ID NO: 29 (Split-ABE8e-N), and the base editing fusion protein B having an amino acid sequence shown in SEQ ID NO: 30 (Split-ABE8e-C); and
   (g) the base editing fusion protein A having an amino acid sequence shown in SEQ ID NO: 31 (Split-ABE8e-N7), and the base editing fusion protein B having an amino acid sequence shown in SEQ ID NO: 32 (Split-ABE8e-C2).

2. The complementary base editing system according to claim 1, wherein the nucleotide sequences encoding the base editing fusion protein A and the base editing fusion protein B and/or the nucleotide sequence encoding the gRNA are/is operably linked to an expression regulatory element.

3. The complementary base editing system according to claim 2, wherein the expression regulatory element is a promoter; and the promoter is selected from the group consisting of a viral 35S promoter, a maize Ubi-1 promoter, a rice Ubi promoter, a cytomegalovirus (CMV) promoter, a yeast TDH3 promoter, a yeast GAL1 promoter, an *Arabidopsis thaliana* egg cell-specific EC1.2en+EC1.1 chimeric promoter, a rice U6 promoter, an *Arabidopsis thaliana* U6 promoter, a yeast U6 promoter, and a human U6 promoter.

* * * * *

SEQUENCE LISTING

```
Sequence total quantity: 183
SEQ ID NO: 1            moltype = AA  length = 1246
FEATURE                 Location/Qualifiers
source                  1..1246
                        mol_type = protein
                        organism = synthetic construct
REGION                  1..1246
                        note = synthetic
SEQUENCE: 1
DKKYSIGLAI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLKDDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKG                1246

SEQ ID NO: 2            moltype = AA  length = 121
FEATURE                 Location/Qualifiers
source                  1..121
                        mol_type = protein
                        organism = synthetic construct
REGION                  1..121
                        note = synthetic
SEQUENCE: 2
SPEDNEQKQL FVEQHKHYLD EIIEQISEFS KRVILADANL DKVLSAYNKH RDKPIREQAE    60
NIIHLFTLTN LGAPAAFKYF DTTIDRKRYT STKEVLDATL IHQSITGLYE TRIDLSQLGG   120
D                                                                  121

SEQ ID NO: 3            moltype = AA  length = 32
FEATURE                 Location/Qualifiers
source                  1..32
                        mol_type = protein
                        organism = synthetic construct
REGION                  1..32
                        note = synthetic
SEQUENCE: 3
SGGSSGGSSG SETPGTSESA TPESSGGSSG GS                                 32

SEQ ID NO: 4            moltype = AA  length = 155
FEATURE                 Location/Qualifiers
source                  1..155
                        mol_type = protein
                        organism = synthetic construct
```

```
REGION                          1..155
                                note = synthetic
SEQUENCE: 4
DSLLMNRREF LYQFKNVRWA KGRRETYLCY VVERRDCATS FSLDFGYLRN KNGCHVELLF       60
LRYISDWDLD PGRCYRVTWF ISWSPCYDCA RHVADFLRGN PNLSLRIFAA RLYFCEDRKA      120
EPEGLRRLRR AGVQIAIMTF KDYFYCWNTF AENHG                                 155

SEQ ID NO: 5                    moltype = AA  length = 132
FEATURE                         Location/Qualifiers
source                          1..132
                                mol_type = protein
                                organism = synthetic construct
REGION                          1..132
                                note = synthetic
SEQUENCE: 5
DSLLMNRREF LYQFKNVRWA KGRRETYLCY VVERRDCATS FSLDFGYLRN KNGCHVELLF       60
LRYISDWDLD PGRCYRVTWF ISWSPCYDCA RHVADFLRGN PNLSLRIFAA RLYFCEDRKA      120
EPEGLRRLRR AG                                                          132

SEQ ID NO: 6                    moltype = AA  length = 159
FEATURE                         Location/Qualifiers
source                          1..159
                                mol_type = protein
                                organism = synthetic construct
REGION                          1..159
                                note = synthetic
SEQUENCE: 6
SSETGPVAVD PTLRRRIEPH EFEVFFDPRE LRKETCLLYE INWGGRHSIW RHTSQNTNKH       60
VEVNFIEKFT TERYFCPNTR CSITWFLSWS PCGECSRAIT EFLSRYPHVT LFIYIARLYH      120
HADPRNRQGL RDLISSGVTI QIMTEQESGY CWRNFVNYS                             159

SEQ ID NO: 7                    moltype = AA  length = 169
FEATURE                         Location/Qualifiers
source                          1..169
                                mol_type = protein
                                organism = synthetic construct
REGION                          1..169
                                note = synthetic
SEQUENCE: 7
EASPASGPRH LMDPHIFTSN FNNGIGRHKT YLCYEVERLD NGTSVKMDQH RGFLHNQAKN       60
LLCGFYGRHA ELRFLDLVPS LQLDPAQIYR VTWFISWSPC FSWGCAGEVR AFLQENTHVR      120
LRIFAARIYD YDPLYKEALQ MLRDAGAQVS IMTYDEFKHC WDTFVDHQG                  169

SEQ ID NO: 8                    moltype = AA  length = 160
FEATURE                         Location/Qualifiers
source                          1..160
                                mol_type = protein
                                organism = synthetic construct
REGION                          1..160
                                note = synthetic
SEQUENCE: 8
DPDTFTFNFN NDPLVLRRRQ TYLCYEVERL DNGTWVLMDQ HMGFLCNEAK NLLCGFYGRH       60
AELRFLDLVP SLQLDPAQIY RVTWFISWSP CFSWGCAGEV RAFLQENTHV RLRIFAARIY      120
DYDPLYKEAL QMLRDAGAQV SIMTYDEFEY CWDTFVYRQG                            160

SEQ ID NO: 9                    moltype = AA  length = 24
FEATURE                         Location/Qualifiers
source                          1..24
                                mol_type = protein
                                organism = synthetic construct
REGION                          1..24
                                note = synthetic
SEQUENCE: 9
RTFKAWEGLH ENSVRLSGQL RRIL                                              24

SEQ ID NO: 10                   moltype = AA  length = 69
FEATURE                         Location/Qualifiers
source                          1..69
                                mol_type = protein
                                organism = synthetic construct
REGION                          1..69
                                note = synthetic
SEQUENCE: 10
RLYFCEDRKA EPEGLRRLRR AGVQIAIMTF KDYFYCWNTF AENHGRTFKA WEGLHENSVR       60
LSGQLRRIL                                                               69

SEQ ID NO: 11                   moltype = AA  length = 69
FEATURE                         Location/Qualifiers
```

```
source                      1..69
                            mol_type = protein
                            organism = synthetic construct
REGION                      1..69
                            note = synthetic
SEQUENCE: 11
PSNEAHWPRY PHLWVRLYVL ELYCIILGLP PCLNILRRKQ PQLTFFTIAL QSCHYQRLPP      60
HILWATGLK                                                              69

SEQ ID NO: 12               moltype = AA  length = 29
FEATURE                     Location/Qualifiers
source                      1..29
                            mol_type = protein
                            organism = synthetic construct
REGION                      1..29
                            note = synthetic
SEQUENCE: 12
CPFQPWDGLD EHSQALSGRL RAILQNQGN                                        29

SEQ ID NO: 13               moltype = AA  length = 29
FEATURE                     Location/Qualifiers
source                      1..29
                            mol_type = protein
                            organism = synthetic construct
REGION                      1..29
                            note = synthetic
SEQUENCE: 13
CPFQPWDGLE EHSQALSGRL RAILQNQGN                                        29

SEQ ID NO: 14               moltype = AA  length = 83
FEATURE                     Location/Qualifiers
source                      1..83
                            mol_type = protein
                            organism = synthetic construct
REGION                      1..83
                            note = synthetic
SEQUENCE: 14
TNLSDIIEKE TGKQLVIQES ILMLPEEVEE VIGNKPESDI LVHTAYDEST DENVMLLTSD      60
APEYKPWALV IQDSNGENKI KML                                              83

SEQ ID NO: 15               moltype = AA  length = 1450
FEATURE                     Location/Qualifiers
source                      1..1450
                            mol_type = protein
                            organism = synthetic construct
REGION                      1..1450
                            note = synthetic
SEQUENCE: 15
MAPKKKRKVG IHGVPAADKK YSIGLAIGTN SVGWAVITDE YKVPSKKFKV LGNTDRHSIK       60
KNLIGALLFD SGETAEATRL KRTARRRYTR RKNRICYLQE IFSNEMAKVD DSFFHRLEES      120
FLVEEDKKHE RHPIFGNIVD EVAYHEKYPT IYHLRKKLVD STDKADLRLI YLALAHMIKF      180
RGHFLIEGDL NPDNSDVDKL FIQLVQTYNQ LFEENPINAS GVDAKAILSA RLSKSRRLEN      240
LIAQLPGEKK NGLFGNLIAL SLGLTPNFKS NFDLAEDAKL QLSKDTYDDD LDNLLAQIGD      300
QYADLFLAAK NLSDAILLSD ILRVNTEITK APLSASMIKR YDEHHQDLTL LKALVRQQLP      360
EKYKEIFFDQ SKNGYAGYID GGASQEEFYK FIKPILEKMD GTEELLVKLN REDLLRKQRT      420
FDNGSIPHQI HLGELHAILR RQEDFYPFLK DNREKIEKIL TFRIPYYVGP LARGNSRFAW      480
MTRKSEETIT PWNFEEVVDK GASAQSFIER MTNFDKNLPN EKVLPKHSLL YEYFTVYNEL      540
TKVKYVTEGM RKPAFLSGEQ KKAIVDLLFK TNRKVTVKQL KEDYFKKIEC FDSVEISGVE      600
DRFNASLGTY HDLLKIIKDK DFLDNEENED ILEDIVLTLT LFEDREMIEE RLKTYAHLFD      660
DKVMKQLKRR RYTGWGRLSR KLINGIRDKQ SGKTILDFLK SDGFANRNFM QLIHDDSLTF      720
KEDIQKAQVS GQGDSLHEHI ANLAGSPAIK KGILQTVKVV DELVKVMGRH KPENIVIEMA      780
RENQTTQKGQ KNSRERMKRI EEGIKELGSQ ILKEHPVENT QLQNEKLYLY YLQNGRDMYV      840
DQELDINRLS DYDVDHIVPQ SFLKDDSIDN KVLTRSDKNR GKSDNVPSEE VVKKMKNYWR      900
QLLNAKLITQ RKFDNLTKAE RGGLSELDKA GFIKRQLVET RQITKHVAQI LDSRMNTKYD      960
ENDKLIREVK VITLKSKLVS DFRKDFQFYK VREINNYHHA HDAYLNAVVG TALIKKYPKL     1020
ESEFVYGDYK VYDVRKMIAK SEQEIGKATA KYFFYSNIMN FFKTEITLAN GEIRKRPLIE     1080
TNGETGEIVW DKGRDFATVR KVLSMPQVNI VKKTEVQTGG FSKESILPKR NSDKLIARKK     1140
DWDPKKYGGF DSPTVAYSVL VVAKVEKGKS KKLKSVKELL GITIMERSSF EKNPIDFLEA     1200
KGYKEVKKDL IIKLPKYSLF ELENGRKRML ASAGELQKGN ELALPSKYVN FLYLASHYEK     1260
LKGSPGGSSGG SSGSETPGTS ESATPESSGG SSGGSDSLLM NREFLYQFK NVRWAKGRRE     1320
TYLCYVVERR DCATSFSLDF GYLRNKNGCH VELLFLRYIS DWDLDPGRCY RVTWFISWSP     1380
CYDCARHVAD FLRGNPNLSL RIFAARLYFC EDRKAEPEGL RRLRRAGVQI AIMTFKDYFY     1440
CWNTFAENHG                                                           1450

SEQ ID NO: 16               moltype = AA  length = 311
FEATURE                     Location/Qualifiers
source                      1..311
                            mol_type = protein
                            organism = synthetic construct
```

```
REGION                          1..311
                                note = synthetic
SEQUENCE: 16
MRTFKAWEGL HENSVRLSGQ LRRILSGGSS GGSSGSETPG TSESATPESS GGSSGGSSPE   60
DNEQKQLFVE QHKHYLDEII EQISEFSKRV ILADANLDKV LSAYNKHRDK PIREQAENII  120
HLFTLTNLGA PAAFKYFDTT IDRKYTSTK EVLDATLIHQ SITGLYETRI DLSQLGGDGG   180
GGSGGGGSGG GGSGGGGSGG GGSGGGGSTN LSDIIEKETG KQLVIQESIL MLPEEVEEVI  240
GNKPESDILV HTAYDESTDE NVMLLTSDAP EYKPWALVIQ DSNGENKIKM LSGGSKRPAA  300
TKKAGQAKKK K                                                      311

SEQ ID NO: 17                   moltype = AA   length = 1427
FEATURE                         Location/Qualifiers
source                          1..1427
                                mol_type = protein
                                organism = synthetic construct
REGION                          1..1427
                                note = synthetic
SEQUENCE: 17
MAPKKKRKVG IHGVPAADKK YSIGLAIGTN SVGWAVITDE YKVPSKKFKV LGNTDRHSIK   60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY YLQNGRDMYV  840
DQELDINRLS DYDVDHIVPQ SFLKDDSIDN KVLTRSDKNR GKSDNVPSEE VVKKMKNYWR  900
QLLNAKLITQ RKFDNLTKAE RGGLSELDKA GFIKRQLVET RQITKHVAQI LDSRMNTKYD  960
ENDKLIREVK VITLKSKLVS DFRKDFQFYK VREINNYHHA HDAYLNAVVG TALIKKYPKL  1020
ESEFVYGDYK VYDVRKMIAK SEQEIGKATA KYFFYSNIMN FFKTEITLAN GEIRKRPLIE  1080
TNGETGEIVW DKGRDFATVR KVLSMPQVNI VKKTEVQTGG FSKESILPKR NSDKLIARKK  1140
DWDPKKYGGF DSPTVAYSVL VVAKVEKGKS KKLKSVKELL GITIMERSSF EKNPIDFLEA  1200
KGYKEVKKDL IIKLPKYSLF ELENGRKRML ASAGELQKGN ELALPSKYVN FLYLASHYEK  1260
LKGSGGGSSGG SSGSETPGTS ESATPESSGG SSGGSDSLLM NRREFLYQFK NVRWAKGRRE  1320
TYLCYVVERR DCATSFSLDF GYLRNKNGCH VELLFLRYIS DWDLDPGRCY RVTWFISWSP  1380
CYDCARHVAD FLRGNPNLSL RIFAARLYFC EDRKAEPEGL RRLRRAG                1427

SEQ ID NO: 18                   moltype = AA   length = 356
FEATURE                         Location/Qualifiers
source                          1..356
                                mol_type = protein
                                organism = synthetic construct
REGION                          1..356
                                note = synthetic
SEQUENCE: 18
MRLYFCEDRK AEPEGLRRLR RAGVQIAIMT FKDYFYCWNT FAENHGRTFK AWEGLHENSV   60
RLSGQLRRIL SGGSSGGSSG SETPGTSESA TPESSGGSSG GSSPEDNEQK QLFVEQHKHY  120
LDEIIEQISE FSKRVILADA NLDKVLSAYN KHRDKPIREQ AENIIHLFTL TNLGAPAAFK  180
YFDTTIDRKR YTSTKEVLDA TLIHQSITGL YETRIDLSQL GGDGGGGSGG GGSGGGGSGG  240
GGSGGGGSGG GGSTNLSDII EKETGKQLVI QESILMLPEE VEEVIGNKPE SDILVHTAYD  300
ESTDENVMLL TSDAPEYKPW ALVIQDSNGE NKIKMLSGGS KRPAATKKAG QAKKKK      356

SEQ ID NO: 19                   moltype = AA   length = 1454
FEATURE                         Location/Qualifiers
source                          1..1454
                                mol_type = protein
                                organism = synthetic construct
REGION                          1..1454
                                note = synthetic
SEQUENCE: 19
MAPKKKRKVG IHGVPAADKK YSIGLAIGTN SVGWAVITDE YKVPSKKFKV LGNTDRHSIK   60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
```

```
RENQTTQKGQ  KNSRERMKRI  EEGIKELGSQ  ILKEHPVENT  QLQNEKLYLY  YLQNGRDMYV   840
DQELDINRLS  DYDVDHIVPQ  SFLKDDSIDN  KVLTRSDKNR  GKSDNVPSEE  VVKKMKNYWR   900
QLLNAKLITQ  RKFDNLTKAE  RGGLSELDKA  GFIKRQLVET  RQITKHVAQI  LDSRMNTKYD   960
ENDKLIREVK  VITLKSKLVS  DFRKDFQFYK  VREINNYHHA  HDAYLNAVVG  TALIKKYPKL  1020
ESEFVYGDYK  VYDVRKMIAK  SEQEIGKATA  KYFFYSNIMN  FFKTEITLAN  GEIRKRPLIE  1080
TNGETGEIVW  DKGRDFATVR  KVLSMPQVNI  VKKTEVQTGG  FSKESILPKR  NSDKLIARKK  1140
DWDPKKYGGF  DSPTVAYSVL  VVAKVEKGKS  KKLKSVKELL  GITIMERSSF  EKNPIDFLEA  1200
KGYKEVKKDL  IIKLPKYSLF  ELENGRKRML  ASAGELQKGN  ELALPSKYVN  FLYLASHYEK  1260
LKGSGGSSGG  SSGSETPGTS  ESATPESSGG  SSSGSSSETG  PVAVDPTLRR  RIEPHEFEVF  1320
FDPRELRKET  CLLYEINWGG  RHSIWRHTSQ  NTNKHVEVNF  IEKFTTERYF  CPNTRCSITW  1380
FLSWSPCGEC  SRAITEFLSR  YPHVTLFIYI  ARLYHHADPR  NRQGLRDLIS  SGVTIQIMTE  1440
QESGYCWRNF  VNYS                                                       1454

SEQ ID NO: 20            moltype = AA  length = 356
FEATURE                  Location/Qualifiers
source                   1..356
                         mol_type = protein
                         organism = synthetic construct
REGION                   1..356
                         note = synthetic
SEQUENCE: 20
MPSNEAHWPR  YPHLWVRLYV  LELYCIILGL  PPCLNILRRK  QPQLTFFTIA  LQSCHYQRLP   60
PHILWATGLK  SGGSSGGSSG  SETPGTSESA  TPESSGGSSG  GSSPEDNEQK  QLFVEQHKHY  120
LDEIIEQISE  FSKRVILADA  NLDKVLSAYN  KHRDKPIREQ  AENIIHLFTL  TNLGAPAAFK  180
YFDTTIDRKR  YTSTKEVLDA  TLIHQSITGL  YETRIDLSQL  GGDGGGGSGG  GGSGGGGSGG  240
GGSGGGGSGG  GGSTNLSDII  EKETGKQLVI  QESILMLPEE  VEEVIGNKPE  SDILVHTAYD  300
ESTDENVMLL  TSDAPEYKPW  ALVIQDSNGE  NKIKMLSGGS  KRPAATKKAG  QAKKKK      356

SEQ ID NO: 21            moltype = AA  length = 1411
FEATURE                  Location/Qualifiers
source                   1..1411
                         mol_type = protein
                         organism = synthetic construct
REGION                   1..1411
                         note = synthetic
SEQUENCE: 21
TDRHSIKKNL  IGALLFDSGE  TAEATRLKRT  ARRRYTRRKN  RICYLQEIFS  NEMAKVDDSF   60
FHRLEESFLV  EEDKKHERHP  IFGNIVDEVA  YHEKYPTIYH  LRKKLVDSTD  KADLRLIYLA  120
LAHMIKFRGH  FLIEGDLNPD  NSDVDKLFIQ  LVQTYNQLFE  ENPINASGVD  AKAILSARLS  180
KSRRLENLIA  QLPGEKKNGL  FGNLIALSLG  LTPNFKSNFD  LAEDAKLQLS  KDTYDDDLDN  240
LLAQIGDQYA  DLFLAAKNLS  DAILLSDILR  VNTEITKAPL  SASMIKRYDE  HHQDLTLLKA  300
LVRQQLPEKY  KEIFFDQSKN  GYAGYIDGGA  SQEEFYKFIK  PILEKMDGTE  ELLVKLNRED  360
LLRKQRTFDN  GSIPHQIHLG  ELHAILRRQE  DFYPFLKDNR  EKIEKILTFR  IPYYVGPLAR  420
GNSRFAWMTR  KSEETITPWN  FEEVVDKGAS  AQSFIERMTN  FDKNLPNEKV  LPKHSLLYEY  480
FTVYNELTKV  KYVTEGMRKP  AFLSGEQKKA  IVDLLFKTNR  KVTVKQLKED  YFKKIECFDS  540
VEISGVEDRF  NASLGTYHDL  LKIIKDKDFL  DNEENEDILE  DIVLTLTLFE  DREMIEERLK  600
TYAHLFDDKV  MKQLKRRRYT  GWGRLSRKLI  NGIRDKQSGK  TILDFLKSDG  FANRNFMQLI  660
HDDSLTFKED  IQKAQVSGQG  DSLHEHIANL  AGSPAIKKGI  LQTVKVVDEL  VKVMGRHKPE  720
NIVIEMAREN  QTTQKGQKNS  RERMKRIEEG  IKELGSQILK  EHPVENTQLQ  NEKLYLYYLQ  780
NGRDMYVDQE  LDINRLSDYD  VDHIVPQSFL  KDDSIDNKVL  TRSDKNRGKS  DNVPSEEVVK  840
KMKNYWRQLL  NAKLITQRKF  DNLTKAERGG  LSELDKAGFI  KRQLVETRQI  TKHVAQILDS  900
RMNTKYDEND  KLIREVKVIT  LKSKLVSDFR  KDFQFYKVRE  INNYHHAHDA  YLNAVVGTAL  960
IKKYPKLESE  FVYGDYKVYD  VRKMIAKSEQ  EIGKATAKYF  FYSNIMNFFK  TEITLANGEI  1020
RKRPLIETNG  ETGEIVWDKG  RDFATVRKVL  SMPQVNIVKK  TEVQTGGFSK  ESILPKRNSD  1080
KLIARKKDWD  PKKYGGFDSP  TVAYSVLVVA  KVEKGKSKKL  KSVKELLGIT  IMERSSFEKN  1140
PIDFLEAKGY  KEVKKDLIIK  LPKYSLFELE  NGRKRMLASA  GELQKGNELA  LPSKYVNFLY  1200
LASHYEKLKG  SGGSSGGSSG  SETPGTSESA  TPESSGGSSG  GSEASPASGP  RHLMDPHIFT  1260
SNFNNGIGRH  KTYLCYEVER  LDNGTSVKMD  QHRGFLHNQA  KNLLCGFYGR  HAELRFLDLV  1320
PSLQLDPAQI  YRVTWFISWS  PCFSWGCAGE  VRAFLQENTH  VRLRIFAARI  YDYDPLYKEA  1380
LQMLRDAGAQ  VSIMTYDEFK  HCWDTFVDHQ  G                                  1411

SEQ ID NO: 22            moltype = AA  length = 316
FEATURE                  Location/Qualifiers
source                   1..316
                         mol_type = protein
                         organism = synthetic construct
REGION                   1..316
                         note = synthetic
SEQUENCE: 22
MCPFQPWDGL  DEHSQALSGR  LRAILQNQGN  SGGSSGGSSG  SETPGTSESA  TPESSGGSSG   60
GSSPEDNEQK  QLFVEQHKHY  LDEIIEQISE  FSKRVILADA  NLDKVLSAYN  KHRDKPIREQ  120
AENIIHLFTL  TNLGAPAAFK  YFDTTIDRKR  YTSTKEVLDA  TLIHQSITGL  YETRIDLSQL  180
GGDGGGGSGG  GGSGGGGSGG  GGSGGGGSGG  GGSTNLSDII  EKETGKQLVI  QESILMLPEE  240
VEEVIGNKPE  SDILVHTAYD  ESTDENVMLL  TSDAPEYKPW  ALVIQDSNGE  NKIKMLSGGS  300
KRPAATKKAG  QAKKKK                                                      316
```

```
SEQ ID NO: 23              moltype = AA  length = 1455
FEATURE                    Location/Qualifiers
source                     1..1455
                           mol_type = protein
                           organism = synthetic construct
REGION                     1..1455
                           note = synthetic
SEQUENCE: 23
MAPKKKRKVG IHGVPAADKK YSIGLAIGTN SVGWAVITDE YKVPSKKFKV LGNTDRHSIK   60
KNLIGALLFD SGETAEATRL KRTARRRYTR RKNRICYLQE IFSNEMAKVD DSFFHRLEES  120
FLVEEDKKHE RHPIFGNIVD EVAYHEKYPT IYHLRKKLVD STDKADLRLI YLALAHMIKF  180
RGHFLIEGDL NPDNSDVDKL FIQLVQTYNQ LFEENPINAS GVDAKAILSA RLSKSRRLEN  240
LIAQLPGEKK NGLFGNLIAL SLGLTPNFKS NFDLAEDAKL QLSKDTYDDD LDNLLAQIGD  300
QYADLFLAAK NLSDAILLSD ILRVNTEITK APLSASMIKR YDEHHQDLTL LKALVRQQLP  360
EKYKEIFFDQ SKNGYAGYID GGASQEEFYK FIKPILEKMD GTEELLVKLN REDLLRKQRT  420
FDNGSIPHQI HLGELHAILR RQEDFYPFLK DNREKIEKIL TFRIPYYVGP LARGNSRFAW  480
MTRKSEETIT PWNFEEVVDK GASAQSFIER MTNFDKNLPN EKVLPKHSLL YEYFTVYNEL  540
TKVKYVTEGM RKPAFLSGEQ KKAIVDLLFK TNRKVTVKQL KEDYFKKIEC FDSVEISGVE  600
DRFNASLGTY HDLLKIIKDK DFLDNEENED ILEDIVLTLT LFEDREMIEE RLKTYAHLFD  660
DKVMKQLKRR RYTGWGRLSR KLINGIRDKQ SGKTILDFLK SDGFANRNFM QLIHDDSLTF  720
KEDIQKAQVS GQGDSLHEHI ANLAGSPAIK KGILQTVKVV DELVKVMGRH KPENIVIEMA  780
RENQTTQKGQ KNSRERMKRI EEGIKELGSQ ILKEHPVENT QLQNEKLYLY YLQNGRDMYV  840
DQELDINRLS DYDVDHIVPQ SFLKDDSIDN KVLTRSDKNR GKSDNVPSEE VVKKMKNYWR  900
QLLNAKLITQ RKFDNLTKAE RGGLSELDKA GFIKRQLVET RQITKHVAQI LDSRMNTKYD  960
ENDKLIREVK VITLKSKLVS DFRKDFQFYK VREINNYHHA HDAYLNAVVG TALIKKYPKL 1020
ESEFVYGDYK VYDVRKMIAK SEQEIGKATA KYFFYSNIMN FFKTEITLAN GEIRKRPLIE 1080
TNGETGEIVW DKGRDFATVR KVLSMPQVNI VKKTEVQTGG FSKESILPKR NSDKLIARKK 1140
DWDPKKYGGF DSPTVAYSVL VVAKVEKGKS KKLKSVKELL GITIMERSSF EKNPIDFLEA 1200
KGYKEVKKDL IIKLPKYSLF ELENGRKRML ASAGELQKGN EALPSKYVN FLYLASHYEK 1260
LKGSGGSSGG SSGSETPGTS ESATPESSGG SSGGSDPDTF TFNFNNDPLV LRRRQTYLCY 1320
EVERLDNGTW VLMDQHMGFL CNEAKNLLCG FYGRHAELRF LDLVPSLQLD PAQIYRVTWF 1380
ISWSPCFSWG CAGEVRAFLQ ENTHVRLRIF AARIYDYDPL YKEALQMLRD AGAQVSIMTY 1440
DEFEYCWDTF VYRQG                                                 1455

SEQ ID NO: 24              moltype = AA  length = 316
FEATURE                    Location/Qualifiers
source                     1..316
                           mol_type = protein
                           organism = synthetic construct
REGION                     1..316
                           note = synthetic
SEQUENCE: 24
MCPFQPWDGL EEHSQALSGR LRAILQNQGN SGGSSGGSSG SETPGTSESA TPESSGGSSG   60
GSSPEDNEQK QLFVEQHKHY LDEIIEQISE FSKRVILADA NLDKVLSAYN KHRDKPIREQ  120
AENIIHLFTL TNLGAPAAFK YFDTTIDRKR YTSTKEVLDA TLIHQSITGL YETRIDLSQL  180
GGDGGGSGSG GGSGGGGSGG GGSGGGGSGG GGSTNLSDII EKETGKQLVI QESILMLPEE  240
VEEVIGNKPE SDILVHTAYD ESTDENVMLL TSDAPEYKPW ALVIQDSNGE NKIKMLSGGS  300
KRPAATKKAG QAKKKK                                                 316

SEQ ID NO: 25              moltype = AA  length = 124
FEATURE                    Location/Qualifiers
source                     1..124
                           mol_type = protein
                           organism = synthetic construct
REGION                     1..124
                           note = synthetic
SEQUENCE: 25
SEVEFSHEYW MRHALTLAKR ARDEREVPVG AVLVLNNRVI GEGWNRAIGL HDPTAHAEIM   60
ALRQGGLVMQ NYRLIDATLY VTFEPCVMCA GAMIHSRIGR VVFGVRNSKR GAAGSLMNVL  120
NYPG                                                              124

SEQ ID NO: 26              moltype = AA  length = 134
FEATURE                    Location/Qualifiers
source                     1..134
                           mol_type = protein
                           organism = synthetic construct
REGION                     1..134
                           note = synthetic
SEQUENCE: 26
SEVEFSHEYW MRHALTLAKR ARDEREVPVG AVLVLNNRVI GEGWNRAIGL HDPTAHAEIM   60
ALRQGGLVMQ NYRLIDATLY VTFEPCVMCA GAMIHSRIGR VVFGVRNSKR GAAGSLMNVL  120
NYPGMNHRVE ITEG                                                   134

SEQ ID NO: 27              moltype = AA  length = 41
FEATURE                    Location/Qualifiers
source                     1..41
                           mol_type = protein
                           organism = synthetic construct
```

```
REGION                       1..41
                             note = synthetic
SEQUENCE: 27
NHRVEITEGI LADECAALLC DFYRMPRQVF NAQKKAQSSI N                          41

SEQ ID NO: 28                moltype = AA   length = 67
FEATURE                      Location/Qualifiers
source                       1..67
                             mol_type = protein
                             organism = synthetic construct
REGION                       1..67
                             note = synthetic
SEQUENCE: 28
RVVFGVRNSK RGAAGSLMNV LNYPGMNHRV EITEGILADE CAALLCDFYR MPRQVFNAQK      60
KAQSSIN                                                                67

SEQ ID NO: 29                moltype = AA   length = 1419
FEATURE                      Location/Qualifiers
source                       1..1419
                             mol_type = protein
                             organism = synthetic construct
REGION                       1..1419
                             note = synthetic
SEQUENCE: 29
MAPKKKRKVG IHGVPAADKK YSIGLAIGTN SVGWAVITDE YKVPSKKFKV LGNTDRHSIK      60
KNLIGALLFD SGETAEATRL KRTARRRYTR RKNRICYLQE IFSNEMAKVD DSFFHRLEES     120
FLVEEDKKHE RHPIFGNIVD EVAYHEKYPT IYHLRKKLVD STDKADLRLI YLALAHMIKF     180
RGHFLIEGDL NPDNSDVDKL FIQLVQTYNQ LFEENPINAS GVDAKAILSA RLSKSRRLEN     240
LIAQLPGEKK NGLFGNLIAL SLGLTPNFKS NFDLAEDAKL QLSKDTYDDD LDNLLAQIGD     300
QYADLFLAAK NLSDAILLSD ILRVNTEITK APLSASMIKR YDEHHQDLTL LKALVRQQLP     360
EKYKEIFFDQ SKNGYAGYID GGASQEEFYK FIKPILEKMD GTEELLVKLN REDLLRKQRT     420
FDNGSIPHQI HLGELHAILR RQEDFYPFLK DNREKIEKIL TFRIPYYVGP LARGNSRFAW     480
MTRKSEETIT PWNFEEVVDK GASAQSFIER MTNFDKNLPN EKVLPKHSLL YEYFTVYNEL     540
TKVKYVTEGM RKPAFLSGEQ KKAIVDLLFK TNRKVTVKQL KEDYFKKIEC FDSVEISGVE     600
DRFNASLGTY HDLLKIIKDK DFLDNEENED ILEDIVLTLT LFEDREMIEE RLKTYAHLFD     660
DKVMKQLKRR RYTGWGRLSR KLINGIRDKQ SGKTILDFLK SDGFANRNFM QLIHDDSLTF     720
KEDIQKAQVS GQGDSLHEHI ANLAGSPAIK KGILQTVKVV DELVKVMGRH KPENIVIEMA     780
RENQTTQKGQ KNSRERMKRI EEGIKELGSQ ILKEHPVENT QLQNEKLYLY YLQNGRDMYV     840
DQELDINRLS DYDVDHIVPQ SFLKDDSIDN KVLTRSDKNR GKSDNVPSEE VVKKMKNYWR     900
QLLNAKLITQ RKFDNLTKAE RGGLSELDKA GFIKRQLVET RQITKHVAQI LDSRMNTKYD     960
ENDKLIREVK VITLKSKLVS DFRKDFQFYK VREINNYHHA HDAYLNAVVG TALIKKYPKL    1020
ESEFVYGDYK VYDVRKMIAK SEQEIGKATA KYFFYSNIMN FFKTEITLAN GEIRKRPLIE    1080
TNGETGEIVW DKGRDFATVR KVLSMPQVNI VKKTEVQTGG FSKESILPKR NSDKLIARKK    1140
DWDPKKYGGF DSPTVAYSVL VVAKVEKGKS KKLKSVKELL GITIMERSSF EKNPIDFLEA    1200
KGYKEVKKDL IIKLPKYSLF ELENGRKRML ASAGELQKGN ELALPSKYVN FLYLASHYEK    1260
LKGSGGSSGG SSGSETPGTS ESATPESSGG SSGGSSEVEF SHEYWMRHAL TLAKRARDER    1320
EVPVGAVLVL NNRVIGEGWN RAIGLHDPTA HAEIMALRQG GLVMQNYRLI DATLYVTFEP    1380
CVMCAGAMIH SRIGRVVFGV RNSKRGAAGS LMNVLNYPG                          1419

SEQ ID NO: 30                moltype = AA   length = 222
FEATURE                      Location/Qualifiers
source                       1..222
                             mol_type = protein
                             organism = synthetic construct
REGION                       1..222
                             note = synthetic
SEQUENCE: 30
MNHRVEITEG ILADECAALL CDFYRMPRQV FNAQKKAQSS INSGGSSGGS SGSETPGTSE      60
SATPESSGGS SGGSSPEDNE QKQLFVEQHK HYLDEIIEQI SEFSKRVILA DANLDKVLSA     120
YNKHRDKPIR EQAENIIHLF TLTNLGAPAA FKYFDTTIDR KRYTSTKEVL DATLIHQSIT     180
GLYETRIDLS QLGGDKRPAA TKKAGQAKKK KSGGSPKKKR KV                       222

SEQ ID NO: 31                moltype = AA   length = 1429
FEATURE                      Location/Qualifiers
source                       1..1429
                             mol_type = protein
                             organism = synthetic construct
REGION                       1..1429
                             note = synthetic
SEQUENCE: 31
MAPKKKRKVG IHGVPAADKK YSIGLAIGTN SVGWAVITDE YKVPSKKFKV LGNTDRHSIK      60
KNLIGALLFD SGETAEATRL KRTARRRYTR RKNRICYLQE IFSNEMAKVD DSFFHRLEES     120
FLVEEDKKHE RHPIFGNIVD EVAYHEKYPT IYHLRKKLVD STDKADLRLI YLALAHMIKF     180
RGHFLIEGDL NPDNSDVDKL FIQLVQTYNQ LFEENPINAS GVDAKAILSA RLSKSRRLEN     240
LIAQLPGEKK NGLFGNLIAL SLGLTPNFKS NFDLAEDAKL QLSKDTYDDD LDNLLAQIGD     300
QYADLFLAAK NLSDAILLSD ILRVNTEITK APLSASMIKR YDEHHQDLTL LKALVRQQLP     360
EKYKEIFFDQ SKNGYAGYID GGASQEEFYK FIKPILEKMD GTEELLVKLN REDLLRKQRT     420
FDNGSIPHQI HLGELHAILR RQEDFYPFLK DNREKIEKIL TFRIPYYVGP LARGNSRFAW     480
MTRKSEETIT PWNFEEVVDK GASAQSFIER MTNFDKNLPN EKVLPKHSLL YEYFTVYNEL     540
```

```
TKVKYVTEGM RKPAFLSGEQ KKAIVDLLFK TNRKVTVKQL KEDYFKKIEC FDSVEISGVE    600
DRFNASLGTY HDLLKIIKDK DFLDNEENED ILEDIVLTLT LFEDREMIEE RLKTYAHLFD    660
DKVMKQLKRR RYTGWGRLSR KLINGIRDKQ SGKTILDFLK SDGFANRNFM QLIHDDSLTF    720
KEDIQKAQVS GQGDSLHEHI ANLAGSPAIK KGILQTVKVV DELVKVMGRH KPENIVIEMA    780
RENQTTQKGQ KNSRERMKRI EEGIKELGSQ ILKEHPVENT QLQNEKLYLY YLQNGRDMYV    840
DQELDINRLS DYDVDHIVPQ SFLKDDSIDN KVLTRSDKNR GKSDNVPSEE VVKKMKNYWR    900
QLLNAKLITQ RKFDNLTKAE RGGLSELDKA GFIKRQLVET RQITKHVAQI LDSRMNTKYD    960
ENDKLIREVK VITLKSKLVS DFRKDFQFYK VREINNYHHA HDAYLNAVVG TALIKKYPKL   1020
ESEFVYGDYK VYDVRKMIAK SEQEIGKATA KYFFYSNIMN FFKTEITLAN GEIRKRPLIE   1080
TNGETGEIVW DKGRDFATVR KVLSMPQVNI VKKTEVQTGG FSKESILPKR NSDKLIARKK   1140
DWDPKKYGGF DSPTVAYSVL VVAKVEKGKS KKLKSVKELL GITIMERSSF EKNPIDFLEA   1200
KGYKEVKKDL IIKLPKYSLF ELENGRKRML ASAGELQKGN ELALPSKYVN FLYLASHYEK   1260
LKGSGGSSGG SSGSETPGTS ESATPESSGG SSGGSSEVEF SHEYWMRHAL TLAKRARDER   1320
EVPVGAVLVL NNRVIGEGWN RAIGLHDPTA HAEIMALRQG GLVMQNYRLI DATLYVTFEP   1380
CVMCAGAMIH SRIGRVVFGV RNSKRGAAGS LMNVLNYPGM NHRVEITEG              1429

SEQ ID NO: 32            moltype = AA   length = 248
FEATURE                  Location/Qualifiers
source                   1..248
                         mol_type = protein
                         organism = synthetic construct
REGION                   1..248
                         note = synthetic
SEQUENCE: 32
MRVVFGVRNS KRGAAGSLMN VLNYPGMNHR VEITEGILAD ECAALLCDFY RMPRQVFNAQ    60
KKAQSSINSG GSSGGSSGSE TPGTSESATP ESSGGSSGGS SPEDNEQKQL FVEQHKHYLD   120
EIIEQISEFS KRVILADANL DKVLSAYNKH RDKPIREQAE NIIHLFTLTN LGAPAAFKYF   180
DTTIDRKRYT STKEVLDATL IHQSITGLYE TRIDLSQLGG DKRPAATKKA GQAKKKKSGG   240
SPKKKRKV                                                            248

SEQ ID NO: 33            moltype = AA   length = 5
FEATURE                  Location/Qualifiers
source                   1..5
                         mol_type = protein
                         organism = synthetic construct
REGION                   1..5
                         note = synthetic
SEQUENCE: 33
GGGGS                                                                 5

SEQ ID NO: 34            moltype = AA   length = 7
FEATURE                  Location/Qualifiers
source                   1..7
                         mol_type = protein
                         organism = synthetic construct
REGION                   1..7
                         note = synthetic
SEQUENCE: 34
PRGGSGG                                                               7

SEQ ID NO: 35            moltype = AA   length = 7
FEATURE                  Location/Qualifiers
source                   1..7
                         mol_type = protein
                         organism = synthetic construct
REGION                   1..7
                         note = synthetic
SEQUENCE: 35
ARGGSGG                                                               7

SEQ ID NO: 36            moltype = AA   length = 7
FEATURE                  Location/Qualifiers
source                   1..7
                         mol_type = protein
                         organism = synthetic construct
REGION                   1..7
                         note = synthetic
SEQUENCE: 36
PKKKRKV                                                               7

SEQ ID NO: 37            moltype = AA   length = 16
FEATURE                  Location/Qualifiers
source                   1..16
                         mol_type = protein
                         organism = Xenopus laevis
SEQUENCE: 37
KRPAATKKAG QAKKKK                                                    16

SEQ ID NO: 38            moltype = DNA   length = 23
```

-continued

```
FEATURE                 Location/Qualifiers
source                  1..23
                        mol_type = genomic DNA
                        organism = Oryza sativa
SEQUENCE: 38
caaggatccc agccccgtga agg                                              23

SEQ ID NO: 39           moltype = DNA   length = 23
FEATURE                 Location/Qualifiers
source                  1..23
                        mol_type = genomic DNA
                        organism = Oryza sativa
SEQUENCE: 39
accgtcacga ctgtagttag ggg                                              23

SEQ ID NO: 40           moltype = DNA   length = 23
FEATURE                 Location/Qualifiers
source                  1..23
                        mol_type = genomic DNA
                        organism = Oryza sativa
SEQUENCE: 40
tagcacccat gacaatgaca tgg                                              23

SEQ ID NO: 41           moltype = DNA   length = 23
FEATURE                 Location/Qualifiers
source                  1..23
                        mol_type = genomic DNA
                        organism = Oryza sativa
SEQUENCE: 41
gttggtcttt gctcctgcag agg                                              23

SEQ ID NO: 42           moltype = DNA   length = 23
FEATURE                 Location/Qualifiers
source                  1..23
                        mol_type = genomic DNA
                        organism = Oryza sativa
SEQUENCE: 42
tgtacaccac caaaagtgga ggg                                              23

SEQ ID NO: 43           moltype = DNA   length = 23
FEATURE                 Location/Qualifiers
source                  1..23
                        mol_type = genomic DNA
                        organism = Oryza sativa
SEQUENCE: 43
ggagttgtgg tgctttatat agg                                              23

SEQ ID NO: 44           moltype = DNA   length = 23
FEATURE                 Location/Qualifiers
source                  1..23
                        mol_type = genomic DNA
                        organism = Oryza sativa
SEQUENCE: 44
gcttagcacc tggttggagg ggg                                              23

SEQ ID NO: 45           moltype = DNA   length = 23
FEATURE                 Location/Qualifiers
source                  1..23
                        mol_type = genomic DNA
                        organism = Oryza sativa
SEQUENCE: 45
cccctcggac ctctcctcct ggg                                              23

SEQ ID NO: 46           moltype = DNA   length = 23
FEATURE                 Location/Qualifiers
source                  1..23
                        mol_type = genomic DNA
                        organism = Oryza sativa
SEQUENCE: 46
catagcactc aatgcggtct ggg                                              23

SEQ ID NO: 47           moltype = DNA   length = 23
FEATURE                 Location/Qualifiers
source                  1..23
                        mol_type = genomic DNA
                        organism = Oryza sativa
SEQUENCE: 47
agacaagctt ggccctcttt ggg                                              23
```

```
SEQ ID NO: 48              moltype = DNA   length = 23
FEATURE                    Location/Qualifiers
source                     1..23
                           mol_type = genomic DNA
                           organism = Oryza sativa
SEQUENCE: 48
actagatatc taaaccatta agg                                                 23

SEQ ID NO: 49              moltype = DNA   length = 23
FEATURE                    Location/Qualifiers
source                     1..23
                           mol_type = genomic DNA
                           organism = Oryza sativa
SEQUENCE: 49
tctccattga tgcacctcca ggg                                                 23

SEQ ID NO: 50              moltype = DNA   length = 23
FEATURE                    Location/Qualifiers
source                     1..23
                           mol_type = genomic DNA
                           organism = Oryza sativa
SEQUENCE: 50
tccccattta gcgtcatcaa tgg                                                 23

SEQ ID NO: 51              moltype = DNA   length = 23
FEATURE                    Location/Qualifiers
source                     1..23
                           mol_type = genomic DNA
                           organism = Oryza sativa
SEQUENCE: 51
ggaatcacct gcgatagtac cgg                                                 23

SEQ ID NO: 52              moltype = DNA   length = 23
FEATURE                    Location/Qualifiers
source                     1..23
                           mol_type = genomic DNA
                           organism = Oryza sativa
SEQUENCE: 52
tgcacgagaa gtggcacact cgg                                                 23

SEQ ID NO: 53              moltype = DNA   length = 23
FEATURE                    Location/Qualifiers
source                     1..23
                           mol_type = genomic DNA
                           organism = Oryza sativa
SEQUENCE: 53
acgggtggat acgcgttgag agg                                                 23

SEQ ID NO: 54              moltype = DNA   length = 23
FEATURE                    Location/Qualifiers
source                     1..23
                           mol_type = genomic DNA
                           organism = Oryza sativa
SEQUENCE: 54
cctccagata gctgcatgga agg                                                 23

SEQ ID NO: 55              moltype = DNA   length = 26
FEATURE                    Location/Qualifiers
source                     1..26
                           mol_type = genomic DNA
                           organism = Oryza sativa
SEQUENCE: 55
ctcgttccca tgtcattgtc atgggt                                              26

SEQ ID NO: 56              moltype = DNA   length = 26
FEATURE                    Location/Qualifiers
source                     1..26
                           mol_type = genomic DNA
                           organism = Oryza sativa
SEQUENCE: 56
tggtcactca gcctgcagta ctgaat                                              26

SEQ ID NO: 57              moltype = DNA   length = 26
FEATURE                    Location/Qualifiers
source                     1..26
                           mol_type = genomic DNA
                           organism = Oryza sativa
SEQUENCE: 57
gatcatcgac aggtcggcgg cggagt                                              26
```

| | |
|---|---|
| SEQ ID NO: 58 | moltype = DNA   length = 26 |
| FEATURE | Location/Qualifiers |
| source | 1..26 |
| | mol_type = genomic DNA |
| | organism = Oryza sativa |

SEQUENCE: 58
aggtgacggt cgcgtacaac aaggat                                                26

| | |
|---|---|
| SEQ ID NO: 59 | moltype = DNA   length = 67 |
| FEATURE | Location/Qualifiers |
| source | 1..67 |
| | mol_type = other DNA |
| | organism = synthetic construct |
| misc_feature | 1..67 |
| | note = Synthetic |

SEQUENCE: 59
aatgatacgg cgaccaccga gatctacact atagcctaca ctctttccct acacgacgct           60
cttccga                                                                    67

| | |
|---|---|
| SEQ ID NO: 60 | moltype = DNA   length = 64 |
| FEATURE | Location/Qualifiers |
| source | 1..64 |
| | mol_type = other DNA |
| | organism = synthetic construct |
| misc_feature | 1..64 |
| | note = Synthetic |

SEQUENCE: 60
caagcagaag acggcatacg agatcgagta atgtgactgg agttcagacg tgtgctcttc           60
cgat                                                                       64

| | |
|---|---|
| SEQ ID NO: 61 | moltype = DNA   length = 53 |
| FEATURE | Location/Qualifiers |
| source | 1..53 |
| | mol_type = other DNA |
| | organism = synthetic construct |
| misc_feature | 1..53 |
| | note = Synthetic |

SEQUENCE: 61
ggagttcaga cgtgtgctct tccgatctgt caaatccacc accaatccaa tcc                  53

| | |
|---|---|
| SEQ ID NO: 62 | moltype = DNA   length = 53 |
| FEATURE | Location/Qualifiers |
| source | 1..53 |
| | mol_type = other DNA |
| | organism = synthetic construct |
| misc_difference | 28..33 |
| | note = n is a, t, c, or g |

SEQUENCE: 62
tttccctaca cgacgctctt ccgatctnnn nnngctcgac ctgatcggtg ctc                  53

| | |
|---|---|
| SEQ ID NO: 63 | moltype = DNA   length = 54 |
| FEATURE | Location/Qualifiers |
| source | 1..54 |
| | mol_type = other DNA |
| | organism = synthetic construct |
| misc_difference | 28..33 |
| | note = n is a, t, c, or g |

SEQUENCE: 63
tttccctaca cgacgctctt ccgatctnnn nnnccatgga gaagttgaga ggcg                 54

| | |
|---|---|
| SEQ ID NO: 64 | moltype = DNA   length = 52 |
| FEATURE | Location/Qualifiers |
| source | 1..52 |
| | mol_type = other DNA |
| | organism = synthetic construct |
| misc_feature | 1..52 |
| | note = Synthetic |

SEQUENCE: 64
ggagttcaga cgtgtgctct tccgatctca ggaacaccaa tgtcaatctc cc                   52

| | |
|---|---|
| SEQ ID NO: 65 | moltype = DNA   length = 59 |
| FEATURE | Location/Qualifiers |
| source | 1..59 |
| | mol_type = other DNA |
| | organism = synthetic construct |
| misc_difference | 28..33 |
| | note = n is a, t, c, or g |

```
SEQUENCE: 65
tttccctaca cgacgctctt ccgatctnnn nnnaaggtaa taatcattga cgtgtttgg      59

SEQ ID NO: 66           moltype = DNA   length = 48
FEATURE                 Location/Qualifiers
source                  1..48
                        mol_type = other DNA
                        organism = synthetic construct
misc_feature            1..48
                        note = Synthetic
SEQUENCE: 66
ggagttcaga cgtgtgctct tccgatctca gaacatgatg gtggtcgc                  48

SEQ ID NO: 67           moltype = DNA   length = 56
FEATURE                 Location/Qualifiers
source                  1..56
                        mol_type = other DNA
                        organism = synthetic construct
misc_difference         28..33
                        note = n is a, t, c, or g
SEQUENCE: 67
tttccctaca cgacgctctt ccgatctnnn nnngcctact gaacggtttt ctttcc          56

SEQ ID NO: 68           moltype = DNA   length = 51
FEATURE                 Location/Qualifiers
source                  1..51
                        mol_type = other DNA
                        organism = synthetic construct
misc_feature            1..51
                        note = Synthetic
SEQUENCE: 68
ggagttcaga cgtgtgctct tccgatcttg atcagcagca atttcatcag g               51

SEQ ID NO: 69           moltype = DNA   length = 58
FEATURE                 Location/Qualifiers
source                  1..58
                        mol_type = other DNA
                        organism = synthetic construct
misc_difference         28..33
                        note = n is a, t, c, or g
SEQUENCE: 69
tttccctaca cgacgctctt ccgatctnnn nnntctgcaa ctgtgtcttt taacatga        58

SEQ ID NO: 70           moltype = DNA   length = 56
FEATURE                 Location/Qualifiers
source                  1..56
                        mol_type = other DNA
                        organism = synthetic construct
misc_feature            1..56
                        note = Synthetic
SEQUENCE: 70
ggagttcaga cgtgtgctct tccgatctct acctgttgaa gtaaaataga ctatgc          56

SEQ ID NO: 71           moltype = DNA   length = 53
FEATURE                 Location/Qualifiers
source                  1..53
                        mol_type = other DNA
                        organism = synthetic construct
misc_difference         28..33
                        note = n is a, t, c, or g
SEQUENCE: 71
tttccctaca cgacgctctt ccgatctnnn nnntatgccg ccccattatg gat             53

SEQ ID NO: 72           moltype = DNA   length = 49
FEATURE                 Location/Qualifiers
source                  1..49
                        mol_type = other DNA
                        organism = synthetic construct
misc_feature            1..49
                        note = Synthetic
SEQUENCE: 72
ggagttcaga cgtgtgctct tccgatctcc ctatgaggct attgagcgg                  49

SEQ ID NO: 73           moltype = DNA   length = 56
FEATURE                 Location/Qualifiers
source                  1..56
                        mol_type = other DNA
                        organism = synthetic construct
misc_difference         28..33
                        note = n is a, t, c, or g
```

```
SEQUENCE: 73
tttccctaca cgacgctctt ccgatctnnn nnnagaatgg tatttccaac gaccct          56

SEQ ID NO: 74           moltype = DNA  length = 50
FEATURE                 Location/Qualifiers
source                  1..50
                        mol_type = other DNA
                        organism = synthetic construct
misc_feature            1..50
                        note = Synthetic
SEQUENCE: 74
ggagttcaga cgtgtgctct tccgatctga agtgagatca agaacctgga              50

SEQ ID NO: 75           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 75
tgattgcaca cgaactactc tg                                            22

SEQ ID NO: 76           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 76
gcaatggtgc agacaacaac ta                                            22

SEQ ID NO: 77           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 77
tcgatctcta ctgacaatgc ac                                            22

SEQ ID NO: 78           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 78
agtaccatcc atattgcctt cg                                            22

SEQ ID NO: 79           moltype = DNA  length = 20
FEATURE                 Location/Qualifiers
source                  1..20
                        mol_type = other DNA
                        organism = synthetic construct
misc_feature            1..20
                        note = Synthetic
SEQUENCE: 79
atggtgacga aatcgaaccg                                               20

SEQ ID NO: 80           moltype = DNA  length = 20
FEATURE                 Location/Qualifiers
source                  1..20
                        mol_type = other DNA
                        organism = synthetic construct
misc_feature            1..20
                        note = Synthetic
SEQUENCE: 80
acgaccgatt taccaacagg                                               20

SEQ ID NO: 81           moltype = DNA  length = 22
FEATURE                 Location/Qualifiers
source                  1..22
                        mol_type = other DNA
                        organism = synthetic construct
```

```
misc_feature            1..22
                        note = Synthetic
SEQUENCE: 81
gttatctcgt gcagataggc tg                                                22

SEQ ID NO: 82           moltype = DNA  length = 21
FEATURE                 Location/Qualifiers
source                  1..21
                        mol_type = other DNA
                        organism = synthetic construct
misc_feature            1..21
                        note = Synthetic
SEQUENCE: 82
ctcgagccga gcctataacg a                                                 21

SEQ ID NO: 83           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 83
gcccaactct agatccctta ac                                                22

SEQ ID NO: 84           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 84
ccactcacaa ttgcatccaa aa                                                22

SEQ ID NO: 85           moltype = DNA  length = 22
FEATURE                 Location/Qualifiers
source                  1..22
                        mol_type = other DNA
                        organism = synthetic construct
misc_feature            1..22
                        note = Synthetic
SEQUENCE: 85
agctaggtag gtttggggga gg                                                22

SEQ ID NO: 86           moltype = DNA  length = 15
FEATURE                 Location/Qualifiers
source                  1..15
                        mol_type = other DNA
                        organism = synthetic construct
misc_feature            1..15
                        note = Synthetic
SEQUENCE: 86
tggaagcatg gcggg                                                        15

SEQ ID NO: 87           moltype = DNA  length = 23
FEATURE                 Location/Qualifiers
source                  1..23
                        mol_type = other DNA
                        organism = synthetic construct
misc_feature            1..23
                        note = Synthetic
SEQUENCE: 87
agactcagac catgatgcaa act                                               23

SEQ ID NO: 88           moltype = DNA  length = 23
FEATURE                 Location/Qualifiers
source                  1..23
                        mol_type = other DNA
                        organism = synthetic construct
misc_feature            1..23
                        note = Synthetic
SEQUENCE: 88
aagcaacaaa agcatcgtca tca                                               23

SEQ ID NO: 89           moltype = DNA  length = 23
FEATURE                 Location/Qualifiers
```

```
source                     1..23
                           mol_type = other DNA
                           organism = synthetic construct
misc_feature               1..23
                           note = Synthetic
SEQUENCE: 89
tcgtcttcct ttgactttac cga                                              23

SEQ ID NO: 90              moltype = DNA  length = 23
FEATURE                    Location/Qualifiers
source                     1..23
                           mol_type = other DNA
                           organism = synthetic construct
misc_feature               1..23
                           note = Synthetic
SEQUENCE: 90
taaaagcaca gcacagtgtc aag                                              23

SEQ ID NO: 91              moltype = DNA  length = 23
FEATURE                    Location/Qualifiers
source                     1..23
                           mol_type = other DNA
                           organism = synthetic construct
misc_feature               1..23
                           note = Synthetic
SEQUENCE: 91
tagcaagcca ggttgtagga aaa                                              23

SEQ ID NO: 92              moltype = DNA  length = 23
FEATURE                    Location/Qualifiers
source                     1..23
                           mol_type = other DNA
                           organism = synthetic construct
misc_feature               1..23
                           note = Synthetic
SEQUENCE: 92
tagcaactcc tactctgctt tgg                                              23

SEQ ID NO: 93              moltype = DNA  length = 20
FEATURE                    Location/Qualifiers
source                     1..20
                           mol_type = other DNA
                           organism = synthetic construct
misc_feature               1..20
                           note = Synthetic
SEQUENCE: 93
tttctcctga accatggcgg                                                  20

SEQ ID NO: 94              moltype = DNA  length = 20
FEATURE                    Location/Qualifiers
source                     1..20
                           mol_type = other DNA
                           organism = synthetic construct
misc_feature               1..20
                           note = Synthetic
SEQUENCE: 94
gacgagggac ttgtcctgtg                                                  20

SEQ ID NO: 95              moltype = DNA  length = 24
FEATURE                    Location/Qualifiers
source                     1..24
                           mol_type = other DNA
                           organism = synthetic construct
misc_feature               1..24
                           note = Synthetic
SEQUENCE: 95
agtctccaca tgagaccttt agtg                                             24

SEQ ID NO: 96              moltype = DNA  length = 20
FEATURE                    Location/Qualifiers
source                     1..20
                           mol_type = other DNA
                           organism = synthetic construct
misc_feature               1..20
                           note = Synthetic
SEQUENCE: 96
cacctttatc ccacacccca                                                  20

SEQ ID NO: 97              moltype = DNA  length = 25
```

```
FEATURE              Location/Qualifiers
source               1..25
                     mol_type = other DNA
                     organism = synthetic construct
misc_feature         1..25
                     note = Synthetic
SEQUENCE: 97
ttgatacgag gggttaaagt aagac                                           25

SEQ ID NO: 98        moltype = DNA   length = 22
FEATURE              Location/Qualifiers
source               1..22
                     mol_type = other DNA
                     organism = synthetic construct
misc_feature         1..22
                     note = Synthetic
SEQUENCE: 98
aaacgatatg taagctcgac tc                                              22

SEQ ID NO: 99        moltype = DNA   length = 23
FEATURE              Location/Qualifiers
source               1..23
                     mol_type = other DNA
                     organism = synthetic construct
misc_feature         1..23
                     note = Synthetic
SEQUENCE: 99
tcttcagtct tgtgctacac acc                                             23

SEQ ID NO: 100       moltype = DNA   length = 23
FEATURE              Location/Qualifiers
source               1..23
                     mol_type = other DNA
                     organism = synthetic construct
misc_feature         1..23
                     note = Synthetic
SEQUENCE: 100
acattcggat aagcaccgac ttc                                             23

SEQ ID NO: 101       moltype = DNA   length = 20
FEATURE              Location/Qualifiers
source               1..20
                     mol_type = other DNA
                     organism = synthetic construct
misc_feature         1..20
                     note = Synthetic
SEQUENCE: 101
ccttgctctc ggcgataact                                                 20

SEQ ID NO: 102       moltype = DNA   length = 20
FEATURE              Location/Qualifiers
source               1..20
                     mol_type = other DNA
                     organism = synthetic construct
misc_feature         1..20
                     note = Synthetic
SEQUENCE: 102
agaaagggga aaccttcggc                                                 20

SEQ ID NO: 103       moltype = DNA   length = 55
FEATURE              Location/Qualifiers
source               1..55
                     mol_type = other DNA
                     organism = synthetic construct
misc_feature         1..55
                     note = Synthetic
SEQUENCE: 103
tcgtcggcag cgtcagatgt gtataagaga caggaggtag acgctggtac gttgc          55

SEQ ID NO: 104       moltype = DNA   length = 56
FEATURE              Location/Qualifiers
source               1..56
                     mol_type = other DNA
                     organism = synthetic construct
misc_feature         1..56
                     note = Synthetic
SEQUENCE: 104
gtctcgtggg ctcggagatg tgtataagag acaggtctta cctggggcga tgtcga         56
```

| SEQ ID NO: 105 | moltype = DNA length = 56 |
| --- | --- |
| FEATURE | Location/Qualifiers |
| source | 1..56 |
| | mol_type = other DNA |
| | organism = synthetic construct |
| misc_feature | 1..56 |
| | note = Synthetic |

SEQUENCE: 105
tcgtcggcag cgtcagatgt gtataagaga cagctcaaga gttcccagaa ccaatc       56

| SEQ ID NO: 106 | moltype = DNA length = 55 |
| --- | --- |
| FEATURE | Location/Qualifiers |
| source | 1..55 |
| | mol_type = other DNA |
| | organism = synthetic construct |
| misc_feature | 1..55 |
| | note = Synthetic |

SEQUENCE: 106
gtctcgtggg ctcggagatg tgtataagag acagagtgtc tgcgatgatg atgcc        55

| SEQ ID NO: 107 | moltype = DNA length = 53 |
| --- | --- |
| FEATURE | Location/Qualifiers |
| source | 1..53 |
| | mol_type = other DNA |
| | organism = synthetic construct |
| misc_feature | 1..53 |
| | note = Synthetic |

SEQUENCE: 107
tcgtcggcag cgtcagatgt gtataagaga caggcatttg gtgcggccaa tgg          53

| SEQ ID NO: 108 | moltype = DNA length = 54 |
| --- | --- |
| FEATURE | Location/Qualifiers |
| source | 1..54 |
| | mol_type = other DNA |
| | organism = synthetic construct |
| misc_feature | 1..54 |
| | note = Synthetic |

SEQUENCE: 108
gtctcgtggg ctcggagatg tgtataagag acagggaagc gacccagaac tcga         54

| SEQ ID NO: 109 | moltype = DNA length = 53 |
| --- | --- |
| FEATURE | Location/Qualifiers |
| source | 1..53 |
| | mol_type = other DNA |
| | organism = synthetic construct |
| misc_feature | 1..53 |
| | note = Synthetic |

SEQUENCE: 109
tcgtcggcag cgtcagatgt gtataagaga cagtcgagtt ctgggtcgct tcc          53

| SEQ ID NO: 110 | moltype = DNA length = 55 |
| --- | --- |
| FEATURE | Location/Qualifiers |
| source | 1..55 |
| | mol_type = other DNA |
| | organism = synthetic construct |
| misc_feature | 1..55 |
| | note = Synthetic |

SEQUENCE: 110
gtctcgtggg ctcggagatg tgtataagag acagccttga aatgtgaagg cagcg        55

| SEQ ID NO: 111 | moltype = DNA length = 57 |
| --- | --- |
| FEATURE | Location/Qualifiers |
| source | 1..57 |
| | mol_type = other DNA |
| | organism = synthetic construct |
| misc_feature | 1..57 |
| | note = Synthetic |

SEQUENCE: 111
tcgtcggcag cgtcagatgt gtataagaga caggaagacg ccgacataga ggagaag      57

| SEQ ID NO: 112 | moltype = DNA length = 58 |
| --- | --- |
| FEATURE | Location/Qualifiers |
| source | 1..58 |
| | mol_type = other DNA |
| | organism = synthetic construct |
| misc_feature | 1..58 |
| | note = Synthetic |

SEQUENCE: 112
gtctcgtggg ctcggagatg tgtataagag acagcaccta tgccatcctc catagaga     58

```
SEQ ID NO: 113           moltype = DNA  length = 53
FEATURE                  Location/Qualifiers
source                   1..53
                         mol_type = other DNA
                         organism = synthetic construct
misc_feature             1..53
                         note = Synthetic
SEQUENCE: 113
tcgtcggcag cgtcagatgt gtataagaga cagcttccgc tattagggga ctg        53

SEQ ID NO: 114           moltype = DNA  length = 54
FEATURE                  Location/Qualifiers
source                   1..54
                         mol_type = other DNA
                         organism = synthetic construct
misc_feature             1..54
                         note = Synthetic
SEQUENCE: 114
gtctcgtggg ctcggagatg tgtataagag acagccgtgc gcgtaatcct tctc       54

SEQ ID NO: 115           moltype = DNA  length = 55
FEATURE                  Location/Qualifiers
source                   1..55
                         mol_type = other DNA
                         organism = synthetic construct
misc_feature             1..55
                         note = Synthetic
SEQUENCE: 115
tcgtcggcag cgtcagatgt gtataagaga cagcagtcag caatatgctc cacca      55

SEQ ID NO: 116           moltype = DNA  length = 56
FEATURE                  Location/Qualifiers
source                   1..56
                         mol_type = other DNA
                         organism = synthetic construct
misc_feature             1..56
                         note = Synthetic
SEQUENCE: 116
gtctcgtggg ctcggagatg tgtataagag acagctgggg tggaccgtac atattg     56

SEQ ID NO: 117           moltype = DNA  length = 56
FEATURE                  Location/Qualifiers
source                   1..56
                         mol_type = other DNA
                         organism = synthetic construct
misc_feature             1..56
                         note = Synthetic
SEQUENCE: 117
tcgtcggcag cgtcagatgt gtataagaga cagattatca tcgccacttg gcattg     56

SEQ ID NO: 118           moltype = DNA  length = 57
FEATURE                  Location/Qualifiers
source                   1..57
                         mol_type = other DNA
                         organism = synthetic construct
misc_feature             1..57
                         note = Synthetic
SEQUENCE: 118
gtctcgtggg ctcggagatg tgtataagag acagcaattg aatcgtgcca acctgac    57

SEQ ID NO: 119           moltype = DNA  length = 57
FEATURE                  Location/Qualifiers
source                   1..57
                         mol_type = other DNA
                         organism = synthetic construct
misc_feature             1..57
                         note = Synthetic
SEQUENCE: 119
tcgtcggcag cgtcagatgt gtataagaga cagaagcggt gcaccttaca acagtgc    57

SEQ ID NO: 120           moltype = DNA  length = 58
FEATURE                  Location/Qualifiers
source                   1..58
                         mol_type = other DNA
                         organism = synthetic construct
misc_feature             1..58
                         note = Synthetic
```

```
SEQUENCE: 120
gtctcgtggg ctcggagatg tgtataagag acagcggtat gagttgagga ggagactc        58

SEQ ID NO: 121              moltype = DNA   length = 53
FEATURE                     Location/Qualifiers
source                      1..53
                            mol_type = other DNA
                            organism = synthetic construct
misc_feature                1..53
                            note = Synthetic
SEQUENCE: 121
tcgtcggcag cgtcagatgt gtataagaga cagccgcatg ctaaccagtt cgt             53

SEQ ID NO: 122              moltype = DNA   length = 54
FEATURE                     Location/Qualifiers
source                      1..54
                            mol_type = other DNA
                            organism = synthetic construct
misc_feature                1..54
                            note = Synthetic
SEQUENCE: 122
gtctcgtggg ctcggagatg tgtataagag acaggcggat agtaccttct gccg            54

SEQ ID NO: 123              moltype = DNA   length = 57
FEATURE                     Location/Qualifiers
source                      1..57
                            mol_type = other DNA
                            organism = synthetic construct
misc_feature                1..57
                            note = Synthetic
SEQUENCE: 123
tcgtcggcag cgtcagatgt gtataagaga caggaagacg ccgacataga ggagaag         57

SEQ ID NO: 124              moltype = DNA   length = 58
FEATURE                     Location/Qualifiers
source                      1..58
                            mol_type = other DNA
                            organism = synthetic construct
misc_feature                1..58
                            note = Synthetic
SEQUENCE: 124
gtctcgtggg ctcggagatg tgtataagag acagcaccta tgccatcctc catagaga       58

SEQ ID NO: 125              moltype = DNA   length = 59
FEATURE                     Location/Qualifiers
source                      1..59
                            mol_type = other DNA
                            organism = synthetic construct
misc_feature                1..59
                            note = Synthetic
SEQUENCE: 125
tcgtcggcag cgtcagatgt gtataagaga cagcttgtct gtccaaggag aatgaggtc      59

SEQ ID NO: 126              moltype = DNA   length = 57
FEATURE                     Location/Qualifiers
source                      1..57
                            mol_type = other DNA
                            organism = synthetic construct
misc_feature                1..57
                            note = Synthetic
SEQUENCE: 126
gtctcgtggg ctcggagatg tgtataagag acagagaacc cgctgctaga gactcca         57

SEQ ID NO: 127              moltype = DNA   length = 55
FEATURE                     Location/Qualifiers
source                      1..55
                            mol_type = other DNA
                            organism = synthetic construct
misc_feature                1..55
                            note = Synthetic
SEQUENCE: 127
tcgtcggcag cgtcagatgt gtataagaga cagcggctgc tctcacatgc tctag           55

SEQ ID NO: 128              moltype = DNA   length = 56
FEATURE                     Location/Qualifiers
source                      1..56
                            mol_type = other DNA
                            organism = synthetic construct
```

```
misc_feature            1..56
                        note = Synthetic
SEQUENCE: 128
gtctcgtggg ctcggagatg tgtataagag acagggcatg gtttgcctcg tccagg          56

SEQ ID NO: 129          moltype = DNA  length = 57
FEATURE                 Location/Qualifiers
source                  1..57
                        mol_type = other DNA
                        organism = synthetic construct
misc_feature            1..57
                        note = Synthetic
SEQUENCE: 129
tcgtcggcag cgtcagatgt gtataagaga caggggctat caaacctcat gattggc         57

SEQ ID NO: 130          moltype = DNA  length = 60
FEATURE                 Location/Qualifiers
source                  1..60
                        mol_type = other DNA
                        organism = synthetic construct
misc_feature            1..60
                        note = Synthetic
SEQUENCE: 130
gtctcgtggg ctcggagatg tgtataagag acagacacac agacactgca gagaataaca     60

SEQ ID NO: 131          moltype = DNA  length = 53
FEATURE                 Location/Qualifiers
source                  1..53
                        mol_type = other DNA
                        organism = synthetic construct
misc_feature            1..53
                        note = Synthetic
SEQUENCE: 131
tcgtcggcag cgtcagatgt gtataagaga caggctgctg gaataccgag gac             53

SEQ ID NO: 132          moltype = DNA  length = 55
FEATURE                 Location/Qualifiers
source                  1..55
                        mol_type = other DNA
                        organism = synthetic construct
misc_feature            1..55
                        note = Synthetic
SEQUENCE: 132
gtctcgtggg ctcggagatg tgtataagag acaggcaact ctcttttctc cggga           55

SEQ ID NO: 133          moltype = DNA  length = 53
FEATURE                 Location/Qualifiers
source                  1..53
                        mol_type = other DNA
                        organism = synthetic construct
misc_feature            1..53
                        note = Synthetic
SEQUENCE: 133
tcgtcggcag cgtcagatgt gtataagaga caggggtcca aagcaggatg aca             53

SEQ ID NO: 134          moltype = DNA  length = 54
FEATURE                 Location/Qualifiers
source                  1..54
                        mol_type = other DNA
                        organism = synthetic construct
misc_feature            1..54
                        note = Synthetic
SEQUENCE: 134
gtctcgtggg ctcggagatg tgtataagag acagcctttc aacccgaacg gaga            54

SEQ ID NO: 135          moltype = DNA  length = 55
FEATURE                 Location/Qualifiers
source                  1..55
                        mol_type = other DNA
                        organism = synthetic construct
misc_feature            1..55
                        note = Synthetic
SEQUENCE: 135
tcgtcggcag cgtcagatgt gtataagaga cagccaggct cttactgaga aggcc           55

SEQ ID NO: 136          moltype = DNA  length = 55
FEATURE                 Location/Qualifiers
```

```
source                    1..55
                          mol_type = other DNA
                          organism = synthetic construct
misc_feature              1..55
                          note = Synthetic
SEQUENCE: 136
gtctcgtggg ctcggagatg tgtataagag acagtcctgc tcacctgctg ctctg        55

SEQ ID NO: 137            moltype = DNA   length = 53
FEATURE                   Location/Qualifiers
source                    1..53
                          mol_type = other DNA
                          organism = synthetic construct
misc_feature              1..53
                          note = Synthetic
SEQUENCE: 137
tcgtcggcag cgtcagatgt gtataagaga cagcaggcag gcaggctctc cga          53

SEQ ID NO: 138            moltype = DNA   length = 55
FEATURE                   Location/Qualifiers
source                    1..55
                          mol_type = other DNA
                          organism = synthetic construct
misc_feature              1..55
                          note = Synthetic
SEQUENCE: 138
gtctcgtggg ctcggagatg tgtataagag acagcagagt gctgcttgct gctgg        55

SEQ ID NO: 139            moltype = DNA   length = 54
FEATURE                   Location/Qualifiers
source                    1..54
                          mol_type = other DNA
                          organism = synthetic construct
misc_feature              1..54
                          note = Synthetic
SEQUENCE: 139
tcgtcggcag cgtcagatgt gtataagaga cagggactgc cttgctctca ccag         54

SEQ ID NO: 140            moltype = DNA   length = 54
FEATURE                   Location/Qualifiers
source                    1..54
                          mol_type = other DNA
                          organism = synthetic construct
misc_feature              1..54
                          note = Synthetic
SEQUENCE: 140
gtctcgtggg ctcggagatg tgtataagag acagggccct gccacatgcc tctg         54

SEQ ID NO: 141            moltype = DNA   length = 56
FEATURE                   Location/Qualifiers
source                    1..56
                          mol_type = other DNA
                          organism = synthetic construct
misc_feature              1..56
                          note = Synthetic
SEQUENCE: 141
tcgtcggcag cgtcagatgt gtataagaga cagcaaacct gacaagggga ttgcgg       56

SEQ ID NO: 142            moltype = DNA   length = 56
FEATURE                   Location/Qualifiers
source                    1..56
                          mol_type = other DNA
                          organism = synthetic construct
misc_feature              1..56
                          note = Synthetic
SEQUENCE: 142
gtctcgtggg ctcggagatg tgtataagag acaggtcacc aactgggtgt ccaaca       56

SEQ ID NO: 143            moltype = DNA   length = 57
FEATURE                   Location/Qualifiers
source                    1..57
                          mol_type = other DNA
                          organism = synthetic construct
misc_feature              1..57
                          note = Synthetic
SEQUENCE: 143
tcgtcggcag cgtcagatgt gtataagaga caggaagaag ctgtgagagt tcccaac      57

SEQ ID NO: 144            moltype = DNA   length = 57
```

| | |
|---|---|
| FEATURE | Location/Qualifiers |
| source | 1..57 |
| | mol_type = other DNA |
| | organism = synthetic construct |
| misc_feature | 1..57 |
| | note = Synthetic |

SEQUENCE: 144
gtctcgtggg ctcggagatg tgtataagag acaggtccca caccaaccaa ttctcca     57

| | |
|---|---|
| SEQ ID NO: 145 | moltype = DNA  length = 22 |
| FEATURE | Location/Qualifiers |
| source | 1..22 |
| | mol_type = other DNA |
| | organism = synthetic construct |
| misc_feature | 1..22 |
| | note = Synthetic |

SEQUENCE: 145
ccaactggta acccacaaag cc                                           22

| | |
|---|---|
| SEQ ID NO: 146 | moltype = DNA  length = 22 |
| FEATURE | Location/Qualifiers |
| source | 1..22 |
| | mol_type = other DNA |
| | organism = synthetic construct |
| misc_feature | 1..22 |
| | note = Synthetic |

SEQUENCE: 146
gattacagcc tgagccaccg tg                                           22

| | |
|---|---|
| SEQ ID NO: 147 | moltype = DNA  length = 22 |
| FEATURE | Location/Qualifiers |
| source | 1..22 |
| | mol_type = other DNA |
| | organism = synthetic construct |
| misc_feature | 1..22 |
| | note = Synthetic |

SEQUENCE: 147
cctccatctt ctccgcagac ag                                           22

| | |
|---|---|
| SEQ ID NO: 148 | moltype = DNA  length = 22 |
| FEATURE | Location/Qualifiers |
| source | 1..22 |
| | mol_type = other DNA |
| | organism = synthetic construct |
| misc_feature | 1..22 |
| | note = Synthetic |

SEQUENCE: 148
cctcatgcca cctgagacac at                                           22

| | |
|---|---|
| SEQ ID NO: 149 | moltype = DNA  length = 60 |
| FEATURE | Location/Qualifiers |
| source | 1..60 |
| | mol_type = other DNA |
| | organism = synthetic construct |
| misc_difference | 30..37 |
| | note = n is a, t, c, or g |

SEQUENCE: 149
aatgatacgg cgaccaccga gatctacacn nnnnnnntcg tcggcagcgt cagatgtgta  60

| | |
|---|---|
| SEQ ID NO: 150 | moltype = DNA  length = 60 |
| FEATURE | Location/Qualifiers |
| source | 1..60 |
| | mol_type = other DNA |
| | organism = synthetic construct |
| misc_difference | 25..32 |
| | note = n is a, t, c, or g |

SEQUENCE: 150
caagcagaag acggcatacg agatnnnnnn nngtctcgtg ggctcggaga tgtgtataag  60

| | |
|---|---|
| SEQ ID NO: 151 | moltype = DNA  length = 23 |
| FEATURE | Location/Qualifiers |
| source | 1..23 |
| | mol_type = genomic DNA |
| | organism = Saccharomyces cerevisiae |

SEQUENCE: 151
cccccccat gttccgagat cgg                                           23

| | |
|---|---|
| SEQ ID NO: 152 | moltype = DNA  length = 23 |
| FEATURE | Location/Qualifiers |

```
source                  1..23
                        mol_type = genomic DNA
                        organism = Saccharomyces cerevisiae
SEQUENCE: 152
tccccccct caattccagc agg                                         23

SEQ ID NO: 153          moltype = DNA   length = 23
FEATURE                 Location/Qualifiers
source                  1..23
                        mol_type = genomic DNA
                        organism = Saccharomyces cerevisiae
SEQUENCE: 153
atcagccccc cccaaggaa agg                                         23

SEQ ID NO: 154          moltype = DNA   length = 23
FEATURE                 Location/Qualifiers
source                  1..23
                        mol_type = other DNA
                        organism = Saccharomyces cerevisiae
SEQUENCE: 154
gaacagctga acccccccaa tgg                                        23

SEQ ID NO: 155          moltype = DNA   length = 23
FEATURE                 Location/Qualifiers
source                  1..23
                        mol_type = genomic DNA
                        organism = Saccharomyces cerevisiae
SEQUENCE: 155
cattaaagca accccccata ggg                                        23

SEQ ID NO: 156          moltype = DNA   length = 23
FEATURE                 Location/Qualifiers
source                  1..23
                        mol_type = genomic DNA
                        organism = Saccharomyces cerevisiae
SEQUENCE: 156
tccaataacg gaatccaact ggg                                        23

SEQ ID NO: 157          moltype = DNA   length = 23
FEATURE                 Location/Qualifiers
source                  1..23
                        mol_type = genomic DNA
                        organism = Saccharomyces cerevisiae
SEQUENCE: 157
cacaaacaca ccacagacgt ggg                                        23

SEQ ID NO: 158          moltype = DNA   length = 23
FEATURE                 Location/Qualifiers
source                  1..23
                        mol_type = genomic DNA
                        organism = Homo sapiens
SEQUENCE: 158
cccagctcca gcctctgatg agg                                        23

SEQ ID NO: 159          moltype = DNA   length = 23
FEATURE                 Location/Qualifiers
source                  1..23
                        mol_type = genomic DNA
                        organism = Homo sapiens
SEQUENCE: 159
cctccgtatc actctctgac tgg                                        23

SEQ ID NO: 160          moltype = DNA   length = 23
FEATURE                 Location/Qualifiers
source                  1..23
                        mol_type = genomic DNA
                        organism = Homo sapiens
SEQUENCE: 160
gtcgtagcca gtccgaaccc cgg                                        23

SEQ ID NO: 161          moltype = DNA   length = 23
FEATURE                 Location/Qualifiers
source                  1..23
                        mol_type = genomic DNA
                        organism = Homo sapiens
SEQUENCE: 161
gtggcactgc ggctggaggt ggg                                        23

SEQ ID NO: 162          moltype = DNA   length = 23
```

```
FEATURE                 Location/Qualifiers
source                  1..23
                        mol_type = genomic DNA
                        organism = Homo sapiens
SEQUENCE: 162
gcctccccaa agcctggcca ggg                                          23

SEQ ID NO: 163          moltype = DNA   length = 23
FEATURE                 Location/Qualifiers
source                  1..23
                        mol_type = genomic DNA
                        organism = Homo sapiens
SEQUENCE: 163
gggactgatc ccttaatgtg tgg                                          23

SEQ ID NO: 164          moltype = DNA   length = 27
FEATURE                 Location/Qualifiers
source                  1..27
                        mol_type = genomic DNA
                        organism = Homo sapiens
SEQUENCE: 164
gcccagctcc agcctctgat gagggt                                       27

SEQ ID NO: 165          moltype = DNA   length = 28
FEATURE                 Location/Qualifiers
source                  1..28
                        mol_type = genomic DNA
                        organism = Homo sapiens
SEQUENCE: 165
ggcctccgta tcactctctg actggggt                                     28

SEQ ID NO: 166          moltype = DNA   length = 27
FEATURE                 Location/Qualifiers
source                  1..27
                        mol_type = genomic DNA
                        organism = Homo sapiens
SEQUENCE: 166
ggtcgtagcc agtccgaacc ccggagt                                      27

SEQ ID NO: 167          moltype = DNA   length = 26
FEATURE                 Location/Qualifiers
source                  1..26
                        mol_type = genomic DNA
                        organism = Homo sapiens
SEQUENCE: 167
gtggcactgc ggctggaggt ggggt                                        26

SEQ ID NO: 168          moltype = DNA   length = 27
FEATURE                 Location/Qualifiers
source                  1..27
                        mol_type = genomic DNA
                        organism = Homo sapiens
SEQUENCE: 168
ggcctcccca aagcctggcc agggagt                                      27

SEQ ID NO: 169          moltype = DNA   length = 28
FEATURE                 Location/Qualifiers
source                  1..28
                        mol_type = genomic DNA
                        organism = Homo sapiens
SEQUENCE: 169
gtgggactga tcccttaatg tgtggggt                                     28

SEQ ID NO: 170          moltype = DNA   length = 23
FEATURE                 Location/Qualifiers
source                  1..23
                        mol_type = genomic DNA
                        organism = Oryza sativa
SEQUENCE: 170
ggagtcaagg tgctttatat agg                                          23

SEQ ID NO: 171          moltype = DNA   length = 27
FEATURE                 Location/Qualifiers
source                  1..27
                        mol_type = genomic DNA
                        organism = Arabidopsis thaliana
SEQUENCE: 171
taccctggag gtgcatcaat ggagatt                                      27
```

-continued

```
SEQ ID NO: 172            moltype = DNA  length = 27
FEATURE                   Location/Qualifiers
source                    1..27
                          mol_type = genomic DNA
                          organism = Arabidopsis thaliana
SEQUENCE: 172
aatctccatt gatgcacctc cagggta                                           27

SEQ ID NO: 173            moltype = AA  length = 9
FEATURE                   Location/Qualifiers
source                    1..9
                          mol_type = protein
                          organism = Arabidopsis thaliana
SEQUENCE: 173
IEMSAGGPY                                                                9

SEQ ID NO: 174            moltype = DNA  length = 27
FEATURE                   Location/Qualifiers
source                    1..27
                          mol_type = other DNA
                          organism = synthetic construct
misc_feature              1..27
                          note = Synthetic
SEQUENCE: 174
taccctggag gtacatcaat ggagatt                                           27

SEQ ID NO: 175            moltype = DNA  length = 27
FEATURE                   Location/Qualifiers
source                    1..27
                          mol_type = other DNA
                          organism = synthetic construct
misc_feature              1..27
                          note = Synthetic
SEQUENCE: 175
aatctccatt gatgtacctc cagggta                                           27

SEQ ID NO: 176            moltype = AA  length = 9
FEATURE                   Location/Qualifiers
source                    1..9
                          mol_type = protein
                          organism = synthetic construct
REGION                    1..9
                          note = synthetic
SEQUENCE: 176
IEMSTGGPY                                                                9

SEQ ID NO: 177            moltype = DNA  length = 23
FEATURE                   Location/Qualifiers
source                    1..23
                          mol_type = other DNA
                          organism = synthetic construct
misc_feature              1..23
                          note = Synthetic
SEQUENCE: 177
ccctggaggt acatcaatgg aga                                               23

SEQ ID NO: 178            moltype = DNA  length = 23
FEATURE                   Location/Qualifiers
source                    1..23
                          mol_type = genomic DNA
                          organism = Homo sapiens
SEQUENCE: 178
ggctaaagac catagactgt ggg                                               23

SEQ ID NO: 179            moltype = DNA  length = 23
FEATURE                   Location/Qualifiers
source                    1..23
                          mol_type = genomic DNA
                          organism = Homo sapiens
SEQUENCE: 179
gaatactaag catagactcc agg                                               23

SEQ ID NO: 180            moltype = AA  length = 15
FEATURE                   Location/Qualifiers
source                    1..15
                          mol_type = protein
                          organism = synthetic construct
```

```
REGION              1..15
                    note = synthetic
SEQUENCE: 180
GGGGSGGGGS GGGGS                                              15

SEQ ID NO: 181      moltype = AA  length = 21
FEATURE             Location/Qualifiers
source              1..21
                    mol_type = protein
                    organism = synthetic construct
REGION              1..21
                    note = synthetic
SEQUENCE: 181
GGSGGSGGSG GSGGSGGSGG S                                       21

SEQ ID NO: 182      moltype = DNA  length = 20
FEATURE             Location/Qualifiers
source              1..20
                    mol_type = genomic DNA
                    organism = Homo sapiens
SEQUENCE: 182
ggctaaagac catagactgt                                         20

SEQ ID NO: 183      moltype = DNA  length = 20
FEATURE             Location/Qualifiers
source              1..20
                    mol_type = genomic DNA
                    organism = Homo sapiens
SEQUENCE: 183
gaatactaag catagactcc                                         20
```